(12) United States Patent
Duggan

(10) Patent No.: US 9,630,935 B2
(45) Date of Patent: *Apr. 25, 2017

(54) COMPOSITIONS FOR THE TREATMENT OF HYPERTENSION AND/OR FIBROSIS

(71) Applicant: Vectus Biosystems Limited, Rosebery, New South Wales (AU)

(72) Inventor: Karen Annette Duggan, Clovelly (AU)

(73) Assignee: VECTUS BIOSYSTEMS LIMITED, Rosebery (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/022,264

(22) PCT Filed: Sep. 17, 2014

(86) PCT No.: PCT/AU2014/000922
§ 371 (c)(1),
(2) Date: Mar. 16, 2016

(87) PCT Pub. No.: WO2015/039172
PCT Pub. Date: Mar. 26, 2015

(65) Prior Publication Data
US 2016/0280671 A1    Sep. 29, 2016

(30) Foreign Application Priority Data

Sep. 17, 2013  (AU) ................. 2013903571
Sep. 17, 2013  (AU) ................. 2013903572

(51) Int. Cl.
| C07D 263/58 | (2006.01) |
| C07C 311/08 | (2006.01) |
| C07C 275/42 | (2006.01) |
| C07C 237/20 | (2006.01) |
| C07D 213/89 | (2006.01) |
| C07C 255/61 | (2006.01) |
| C07D 213/74 | (2006.01) |
| C07D 215/02 | (2006.01) |
| C07C 271/28 | (2006.01) |
| C07D 231/56 | (2006.01) |
| C07C 307/10 | (2006.01) |
| C07C 311/03 | (2006.01) |
| C07D 235/04 | (2006.01) |
| C07D 249/18 | (2006.01) |
| C07C 235/34 | (2006.01) |
| C07D 263/54 | (2006.01) |
| C07D 209/18 | (2006.01) |
| C07D 277/62 | (2006.01) |
| C07C 261/04 | (2006.01) |
| C07D 209/08 | (2006.01) |
| C07D 209/34 | (2006.01) |
| C07D 215/227 | (2006.01) |
| C07D 235/08 | (2006.01) |
| C07D 235/10 | (2006.01) |
| C07D 235/26 | (2006.01) |
| C07D 277/68 | (2006.01) |

(52) U.S. Cl.
CPC .......... *C07D 263/58* (2013.01); *C07C 235/34* (2013.01); *C07C 237/20* (2013.01); *C07C 255/61* (2013.01); *C07C 261/04* (2013.01); *C07C 271/28* (2013.01); *C07C 275/42* (2013.01); *C07C 307/10* (2013.01); *C07C 311/03* (2013.01); *C07C 311/08* (2013.01); *C07D 209/08* (2013.01); *C07D 209/18* (2013.01); *C07D 209/34* (2013.01); *C07D 213/74* (2013.01); *C07D 213/89* (2013.01); *C07D 215/02* (2013.01); *C07D 215/227* (2013.01); *C07D 231/56* (2013.01); *C07D 235/04* (2013.01); *C07D 235/08* (2013.01); *C07D 235/10* (2013.01); *C07D 235/26* (2013.01); *C07D 249/18* (2013.01); *C07D 263/54* (2013.01); *C07D 277/62* (2013.01); *C07D 277/68* (2013.01)

(58) Field of Classification Search
IPC .............. C07D 263/58,213/89, 209/08, 231/56, 235/26, 235/08, 235/10, 249/18; C07C 275/42, 311/08, 237/20
See application file for complete search history.

(56) References Cited

U.S. PATENT DOCUMENTS

2011/0082109 A1* 4/2011 Miyanaga ............. C07C 279/22
514/64

FOREIGN PATENT DOCUMENTS

WO   WO 2005/120545 A1   12/2005
WO   WO 2006/018325 A1   2/2006

OTHER PUBLICATIONS

Peters et al., Chemistry Eur. J (2013) 19, 2442-2449.*
Huang et al., Synthesis and biological evaluation of ortho-aryl N-hydroxycinnamides as potent histone deacetylase (HDAC) 8 isoform-selective inhibitors. ChemMedChem. Oct. 2012;7(10):1815-24. doi: 10.1002/cmdc.201200300. Epub Aug. 20, 2012.
Peters et al., A modular synthesis of teraryl-based α-helix mimetics, part 1: Synthesis of core fragments with two electronically differentiated leaving groups. Chemistry. Feb. 11, 2013;19(7):2442-9. doi: 10.1002/chem.201203005. Epub Jan. 4, 2013.

* cited by examiner

*Primary Examiner* — Shirley V Gembeh
(74) *Attorney, Agent, or Firm* — John R. Van Amsterdam

(57) ABSTRACT

The present invention relates to novel compounds and their use in the prophylactic and/or therapeutic treatment of hypertension and/or fibrosis.

18 Claims, 16 Drawing Sheets

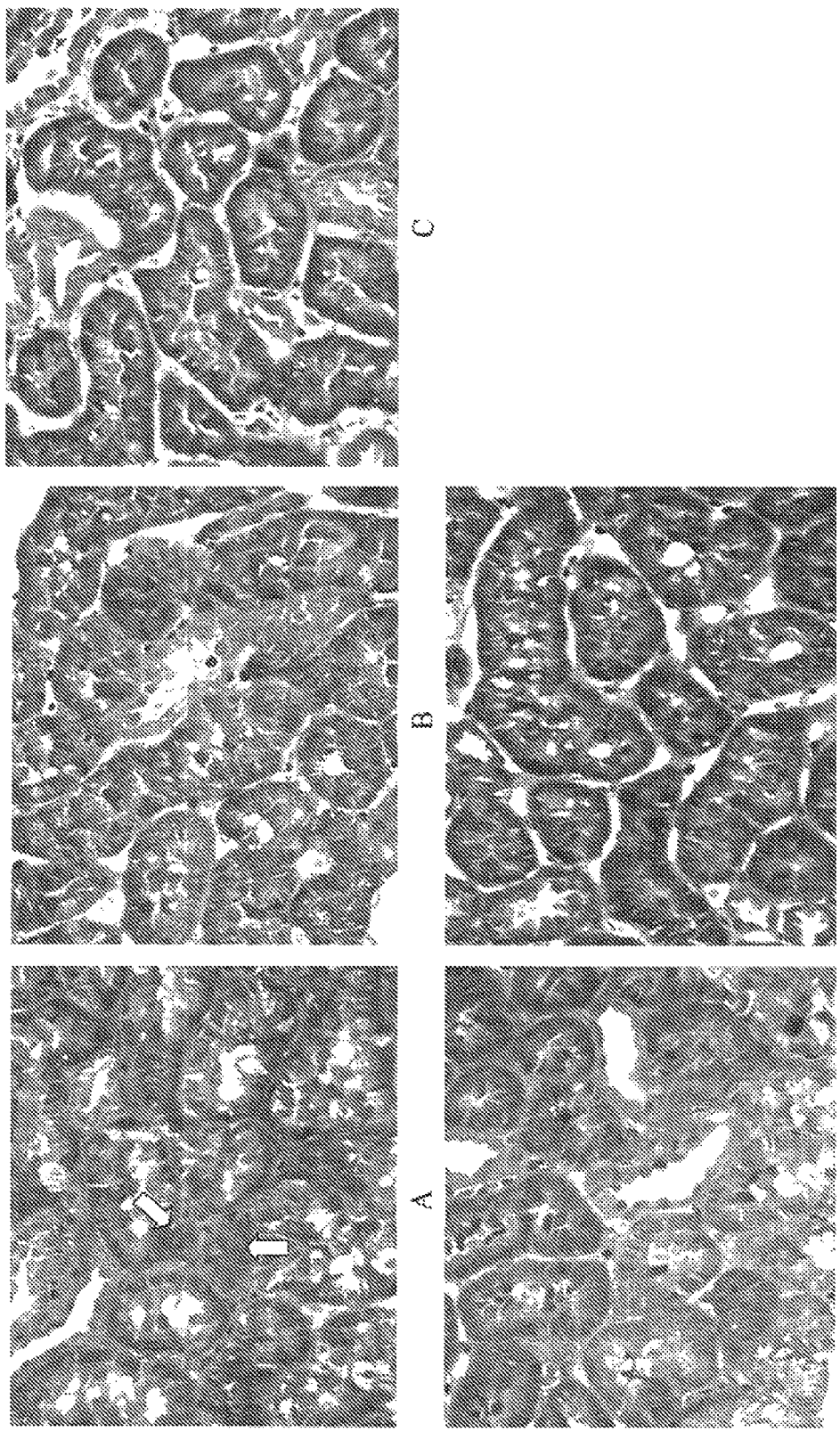

COMPOSITIONS FOR THE TREATMENT OF HYPERTENSION AND/OR FIBROSIS

RELATED APPLICATION

This application is a national stage filing under 35 U.S.C. §371 of international application PCT/AU2014/000922, filed Sep. 17, 2014, which was published under PCT Article 21(2) in English, the contents of which are incorporated by reference herein in its entirety.

FIELD OF THE INVENTION

The present invention relates to novel compounds and their use in the prophylactic and/or therapeutic treatment of cardiovascular disease, and in particular the treatment of prehypertension, hypertension and/or fibrotic conditions.

The invention has been developed primarily for the prophylactic and/or therapeutic treatment of cardiovascular disease and will be described hereinafter with reference to this application. However, it will be appreciated that the invention is not limited to this particular field of use.

BACKGROUND OF THE INVENTION

Any discussion of the prior art throughout the specification should in no way be considered as an admission that such prior art is widely known or forms part of the common general knowledge in the field.

Hypertension (high blood pressure) affects 26% of the adult population worldwide with an incidence of 30-33% in western countries. The world wide incidence of hypertension is expected to reach 29% by 2025 as a consequence of the westernisation of India and China. Current studies indicate that fewer than 20% of patients with hypertension attain their recommended blood pressure (BP) target and that to achieve these targets >75% of patients require therapy with multiple antihypertensive agents. Prehypertension (slightly elevated blood pressure) affects 31% of adults in the US and may develop into hypertension if not treated.

All currently available therapies have side effects:
Angiotensin Converting Enzyme Inhibitors (ACEI)—cough, angioneurotic oedema, hyperkalaemia;
Angiotensin Receptor Blockers (ARB's)—angioneurotic oedema, hyperkalaemia;
Calcium Channel Blockers (CCB)—flushing, leg/ankle oedema, constipation;
Thiazide diuretics—new onset diabetes, gout, hyponatraemia;
Beta (β) Blockers—new onset diabetes, inability to exercise, bradycardia, masking hypoglycaemia in diabetics; and
Aldosterone Antagonists—gynaecomastia, menorrhagia, hyperkalaemia.

The need to use combination therapy increases the likelihood that patients will experience side effects and as a consequence not attain their BP target.

Hypertension and prehypertension are a major factor in the development of heart, kidney and blood vessel damage, resulting in the replacement of normal functional tissue by scar tissue or fibrosis. Some of the current antihypertensive agents—ACE inhibitors, ARB's renin inhibitors and aldosterone antagonists are able to slow the progression of the replacement of functional tissue by fibrosis, none have been shown to reverse existing fibrosis and restore normal tissue architecture. There is thus a need for agents which have to the efficacy to reduce BP significantly and thus enable a larger proportion of patients to attain BP target with single agent therapy and/or to reverse existing fibrosis and/or restore normal tissue architecture.

It is an object of the present invention to overcome or ameliorate at least one of the disadvantages of the prior art, or to provide a useful alternative.

SUMMARY OF THE INVENTION

Surprisingly, the present inventors have found that certain novel terphenyl compounds have blood pressure lowering and/or anti-fibrotic effects. These effects may be seen in intravenous and/or oral dosing studies.

According to one aspect, the present invention provides a compound of the formula

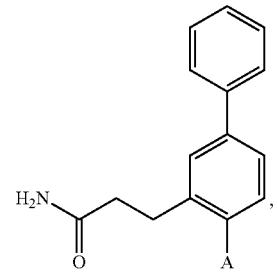

wherein:
A is selected from the group consisting of:

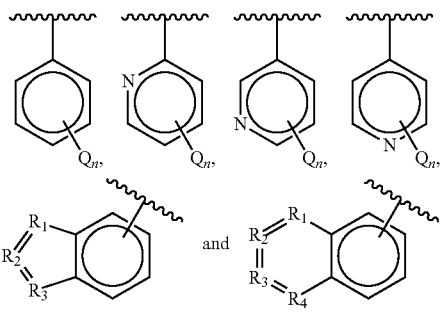

Q is independently selected from halo, alkyl, hydroxy, amino and substituted amino;
n is 0, 1, 2, 3, 4 or 5;
$R_1$, $R_3$ and $R_4$ are independently C, CH, $CH_2$, O, N, NH or S, and
$R_2$ is C, CH, $CH_2$, N, NH, C—$CF_3$, CH—$CF_3$ or C=O,
or a stereoisomer or pharmaceutically acceptable salt thereof,
wherein when n is 1, Q cannot be hydroxy.

In one embodiment, Q is halo selected from the group consisting of F, Cl, Br and I.

In one embodiment, Q is substituted amino of the formula —NHW and wherein:
W is selected from —CN, —$SO_2(X)_n$Y and —CO$(X)_n$Y,
a is 0 or 1,
X is selected from —NH— and —O—, and
Y is selected from —H, —$CH_3$, —$CH_2CH_3$, —$CH_2OH$ and —$CH_2CH_2OH$.

In one embodiment, Q is substituted amino selected from the group consisting of —$NHSO_2CH_3$, —NHCOH, —$NHCONHCH_3$, —$NHCONHCH_2CH_3$, —NHSO$_2$NHCH$_3$, —NHSO$_2$NHCH$_2$CH$_3$, —NHCOCH$_3$, —NHCOOCH$_3$, —NHCOOCH$_2$CH$_2$OH, —NHCONH$_2$ and —NHCN.

In one embodiment, Q is alkyl selected from the group consisting of methyl, ethyl, propyl, butyl and pentyl.

In one embodiment, A is selected from:

[Structures shown: various heterocyclic ring systems including indole, oxindole, benzoxazolone, benzothiazolone, benzimidazolone, dihydroquinolinone, difluoromethyl-benzimidazole, benzimidazole, indazole, and benzotriazole]

In one embodiment, A is

[Structure with R$_9$, R$_8$, R$_7$, R$_6$, R$_5$ substituents on a six-membered ring with X, Y, Z positions]

wherein:

X, Y or Z are C or N, wherein only one of X, Y or Z can be N,

R$_5$ to R$_9$ are independently selected from hydrogen, halo, alkyl, hydroxy, amino and substituted amino, with the proviso that when one of R$_5$ to R$_9$ is halo, then at least one of the remaining R$_5$ to R$_9$ cannot be hydrogen.

In one embodiment, A is

[Structure with R$_9$, R$_8$, R$_7$, R$_6$, R$_5$ substituents on a six-membered ring with X, Y, Z positions]

wherein:

X, Y or Z are C or N, wherein only one of X, Y or Z can be N,

R$_5$ to R$_9$ are independently selected from hydrogen, halo, alkyl, hydroxy, amino and substituted amino, with the proviso that when one of R$_5$ to R$_9$ is halo, then at least one of the remaining R$_5$ to R$_9$ must be halo, alkyl, hydroxy, amino or substituted amino.

In one embodiment, A is

[Structure with R$_9$, R$_8$, R$_7$, R$_6$, R$_5$ substituents on a six-membered ring with X, Y, Z positions]

wherein:

X, Y or Z are C or N, wherein only one of X, Y or Z can be N,

R$_5$ to R$_9$ are independently selected from hydrogen, halo, alkyl, hydroxy, amino and substituted amino, with the proviso that when one of R$_5$ to R$_9$ is halo, then at least one of the remaining R$_5$ to R$_9$ must be alkyl, hydroxy, amino or substituted amino.

In one embodiment, A is

[Structure with R$_9$, R$_8$, R$_7$, R$_6$, R$_5$ substituents on a six-membered ring with X, Y, Z positions]

wherein:

X, Y or Z are C or N, wherein only one of X, Y or Z can be N,

R$_5$ to R$_9$ are independently selected from hydrogen, halo, alkyl, hydroxy, amino and substituted amino, with the proviso that when one of R$_5$ to R$_9$ is alkyl, then at least one of the remaining R$_5$ to R$_9$ cannot be hydrogen.

In one embodiment, A is

[Structure with R$_9$, R$_8$, R$_7$, R$_6$, R$_5$ substituents on a six-membered ring with X, Y, Z positions]

wherein:

X, Y or Z are C or N, wherein only one of X, Y or Z can be N,

R$_5$ to R$_9$ are independently selected from hydrogen, halo, alkyl, hydroxy, amino and substituted amino, with the proviso that when one of R$_5$ to R$_9$ is alkyl, then at least one of the remaining R$_5$ to R$_9$ must be halo, alkyl, hydroxy, amino or substituted amino.

In one embodiment, A is

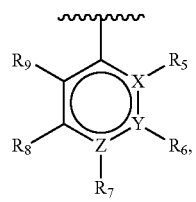

wherein:

X, Y or Z are C or N, wherein only one of X, Y or Z can be N, $R_5$ to $R_9$ are independently selected from hydrogen, halo, alkyl, hydroxy, amino and substituted amino, with the proviso that when one of $R_5$ to $R_9$ is alkyl, then at least one of the remaining $R_5$ to $R_9$ must be halo, hydroxy, amino or substituted amino.

In one embodiment, A is

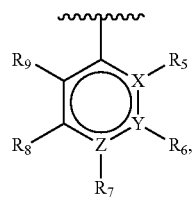

wherein:

X, Y or Z are C or N, wherein only one of X, Y or Z can be N, $R_5$ to $R_9$ are independently selected from hydrogen, halo, alkyl, hydroxy, amino and substituted amino, with the proviso that when one of $R_5$ to $R_9$ is hydroxy, then at least one of the remaining $R_5$ to $R_9$ cannot be hydrogen In one embodiment, A is

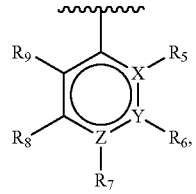

wherein:

X, Y or Z are C or N, wherein only one of X, Y or Z can be N, $R_5$ to $R_9$ are independently selected from hydrogen, halo, alkyl, hydroxy, amino and substituted amino, with the proviso that when one of $R_5$ to $R_9$ is hydroxy, then at least one of the remaining $R_5$ to $R_9$ must be halo, amino or substituted amino.

In one embodiment, A is

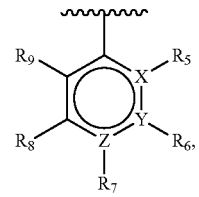

wherein:

X, Y or Z are C or N, wherein only one of X, Y or Z can be N, $R_5$ to $R_9$ are independently selected from hydrogen, halo, alkyl, hydroxy, amino and substituted amino, with the proviso that when one of $R_5$ to $R_9$ is hydroxy, then at least one of the remaining $R_5$ to $R_9$ must be halo, amino or substituted amino.

In one embodiment, A is

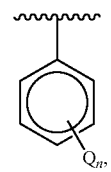

Q is substituted amino and n is 1.

In one embodiment, A is

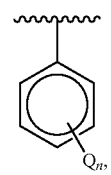

Q is substituted amino and n is 2.

In one embodiment, A is

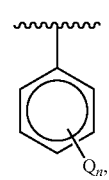

Q is amino and n is 1.

In one embodiment, A is

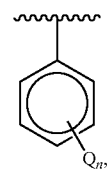

Q is amino and n is 2.

In one embodiment, A is

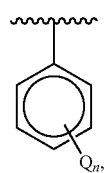

Q is hydroxy and n is 2.

In one embodiment, A is

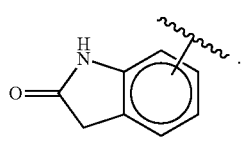

In one embodiment, A is

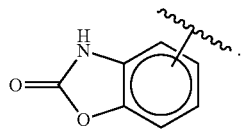

In one embodiment, A is

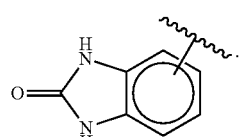

In one embodiment, A is

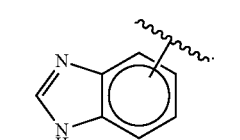

In one embodiment, A is

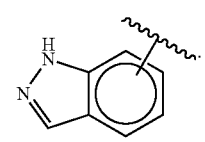

In one embodiment, A is

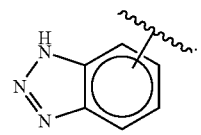

In one embodiment, A is

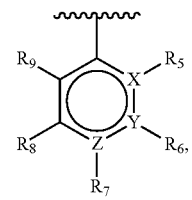

X and Y are C, Z is N and one of $R_5$ to $R_9$ is amino.

In one embodiment, A is

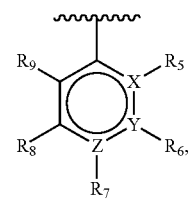

X, Y and Z are all C, one of $R_5$ to $R_9$ is hydroxy and at least one of the remaining $R_5$ to $R_9$ is halo.

In one embodiment, A is

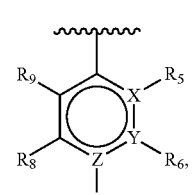

Z, Y and Z are all C, two of $R_5$ to $R_9$ are hydroxy and at least one of the remaining $R_5$ to $R_9$ is halo.

In one embodiment, A is

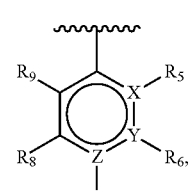

Z, Y and Z are all C, two of $R_5$ to $R_9$ are hydroxy and at least one of the remaining $R_5$ to $R_9$ is alkyl.

In one embodiment, A is

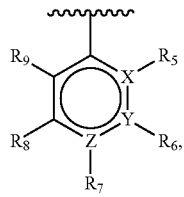

Z, Y and Z are all C, one of $R_5$ to $R_9$ is alkyl and at least one of the remaining $R_5$ to $R_9$ is hydroxy.

In one embodiment, A is

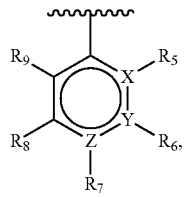

Z, Y and Z are all C, one of $R_5$ to $R_9$ is halo and at least one of the remaining $R_5$ to $R_9$ is hydroxy.

In one embodiment, A is

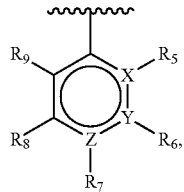

Z, Y and Z are all C, two of $R_5$ to $R_9$ is halo and at least one of the remaining $R_5$ to $R_9$ is hydroxy.

In one embodiment, the compound is selected from the group consisting of.

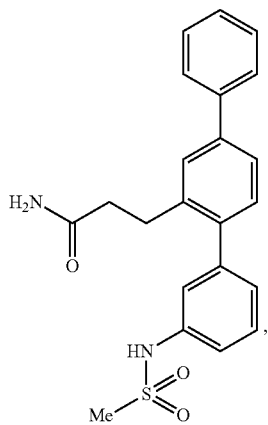
(T1)

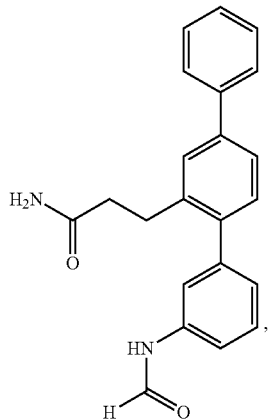
(T2)

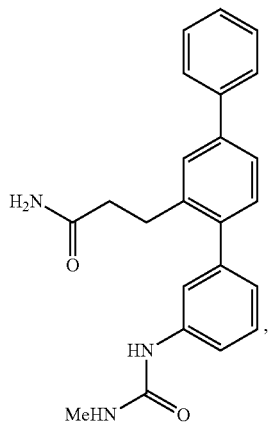
(T3)

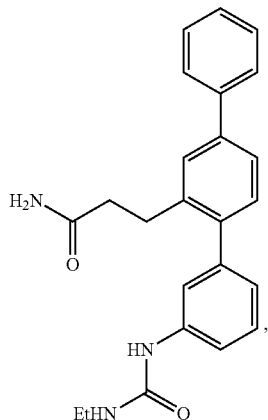
(T4)

(T5)
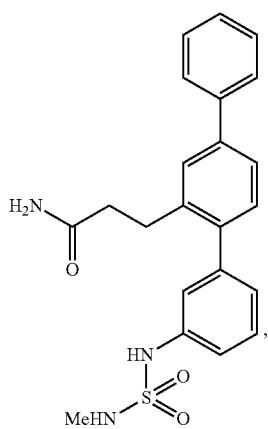
(T6)
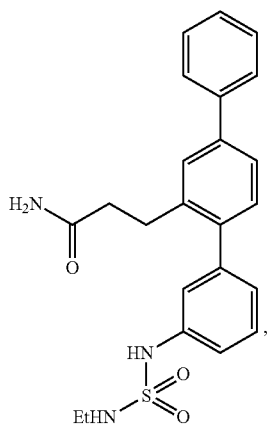
(T10)
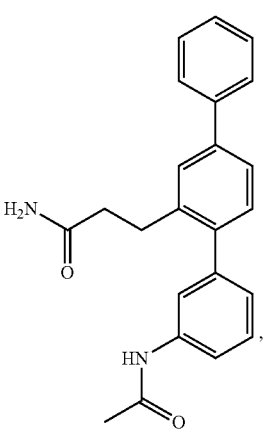
(T11)
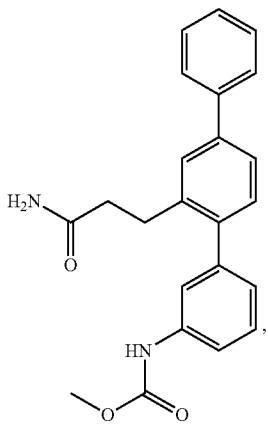
(T12)
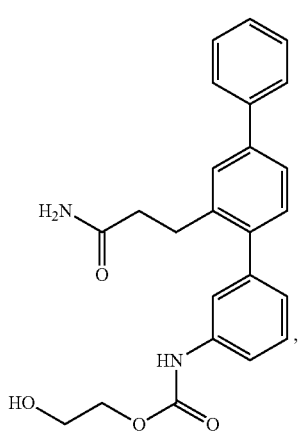
(T15)
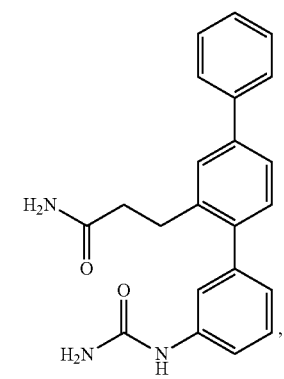
(T16)
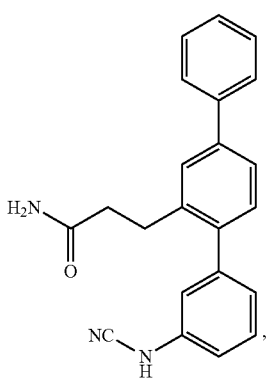

(T18)
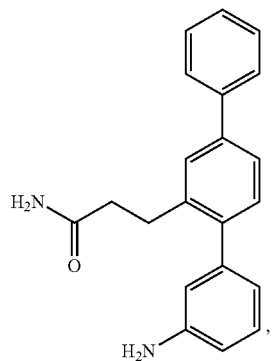
(T20)
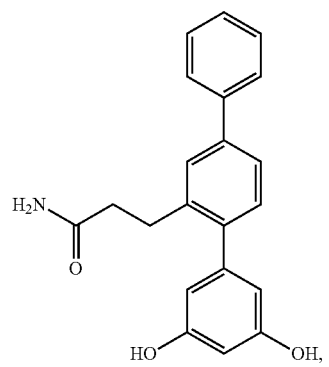
(T22)
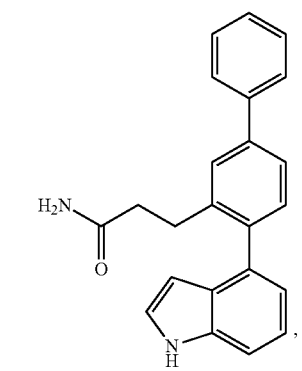
(T23)
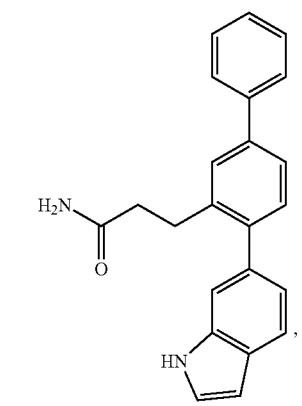
(T24)
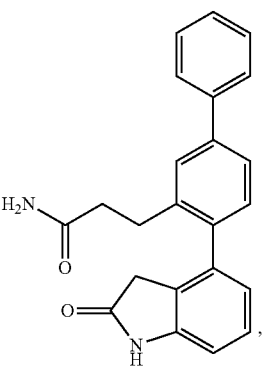
(T25)
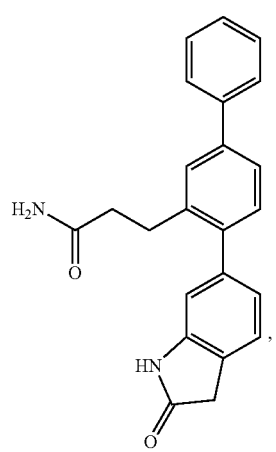
(T26)
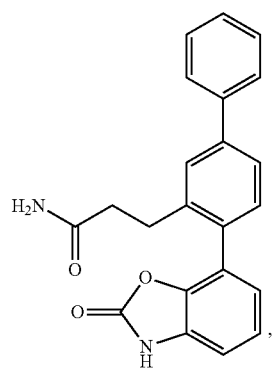
(T27)
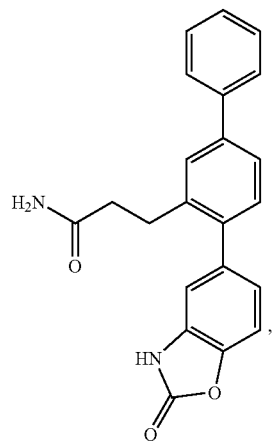

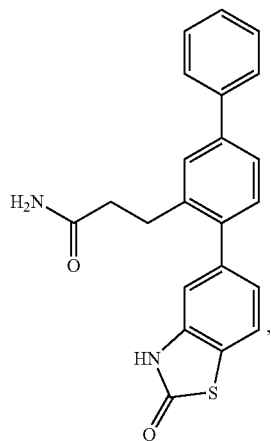
(T29)
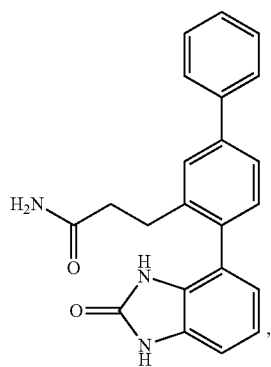
(T30)
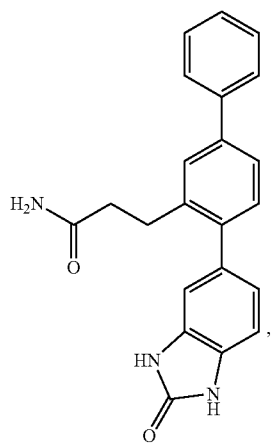
(T31)
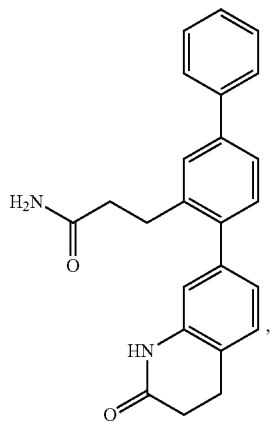
(T32)
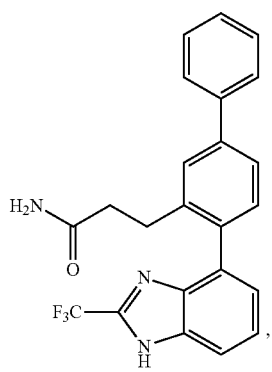
(T33)
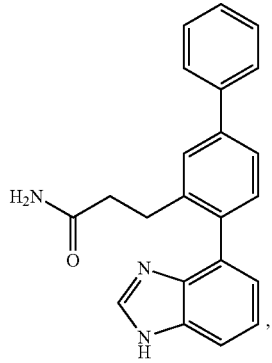
(T35)
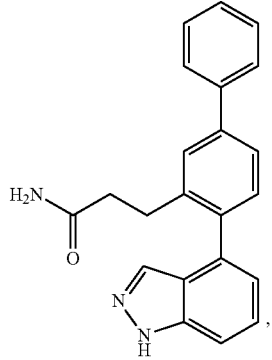
(T37)

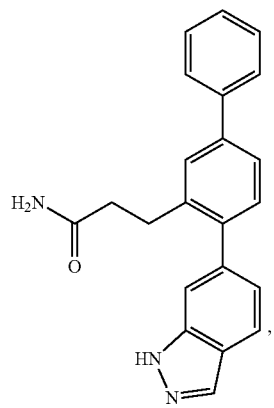
(T38)
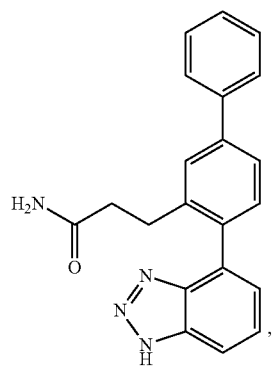
(T39)
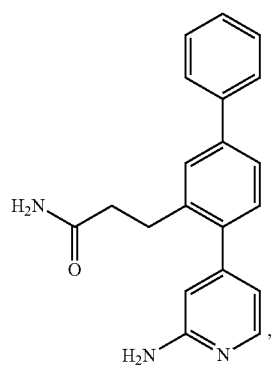
(T48)
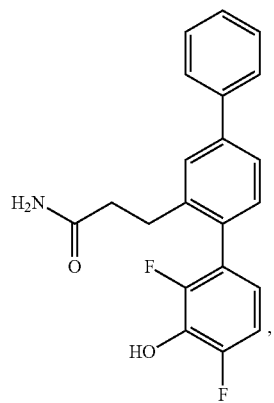
(T58)
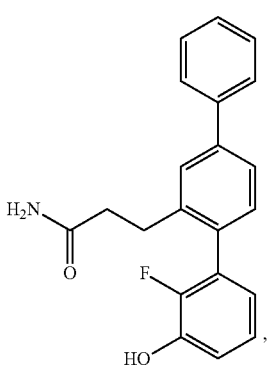
(T63)
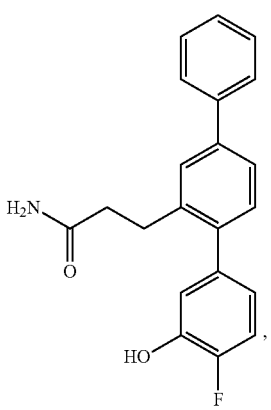
(T64)
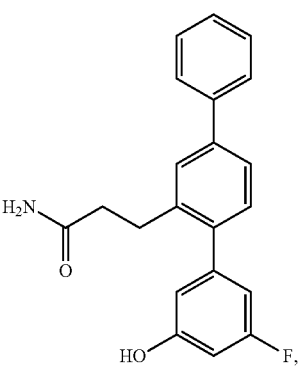
(T65)
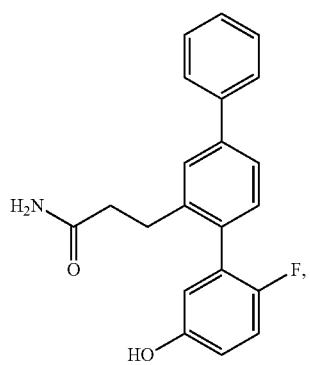
(T66)

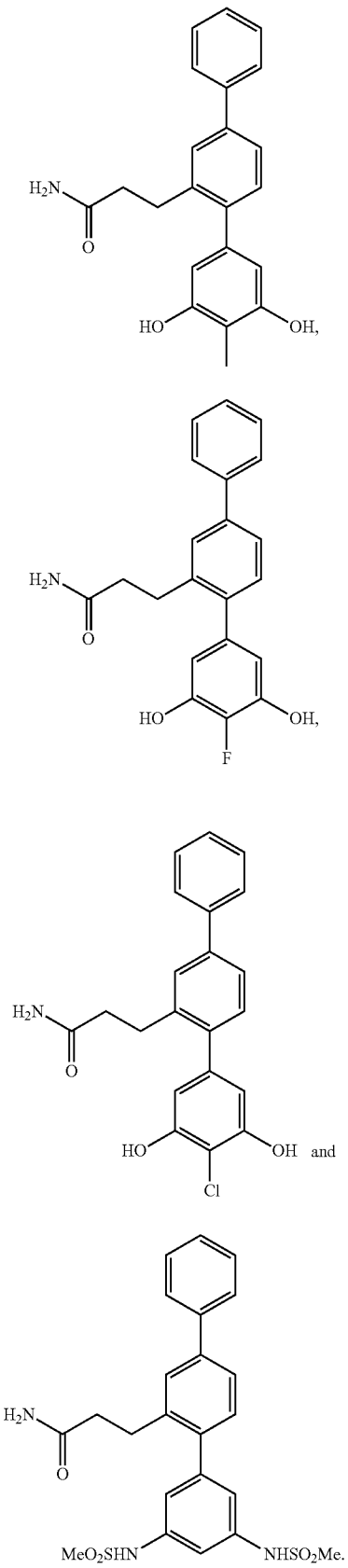

According to another aspect, the present invention relates to a pharmaceutical composition comprising a compound of the present invention and a pharmaceutically acceptable excipient.

According to another aspect, the present invention relates to a method for the therapeutic treatment of hypertension or prehypertension in a subject comprising administering to the subject a compound according to the present invention.

According to another aspect, the present invention relates to a method for the therapeutic treatment of fibrosis in a subject comprising administering to the subject a compound according to the present invention.

According to another aspect, the present invention relates to a method for the prophylactic treatment of fibrosis in a subject comprising administering to the subject a compound according to the present invention.

According to another aspect, the present invention relates to a method for the therapeutic treatment of hypertension and fibrosis in a subject comprising administering to the subject a compound according to the present invention.

According to another aspect, the present invention relates to a method for the therapeutic treatment of prehypertension and fibrosis in a subject comprising administering to the subject a compound according to the present invention.

In one embodiment, the fibrosis is myocardial fibrosis or kidney fibrosis.

In another embodiment, the fibrosis is myocardial fibrosis and kidney fibrosis.

According to another aspect, the present invention relates to a compound of the present invention for use in the therapeutic treatment of hypertension or prehypertension.

According to another aspect, the present invention relates to a compound of the present invention for use in the therapeutic treatment of fibrosis.

According to another aspect, the present invention relates to a compound of the present invention for use in the prophylactic treatment of fibrosis.

According to another aspect, the present invention relates to a compound of the present invention for use in the therapeutic treatment of hypertension and fibrosis.

According to another aspect, the present invention relates to a compound of the present invention for use in the therapeutic treatment of prehypertension and fibrosis.

According to another aspect, the present invention relates to use of a compound of the present invention for the manufacture of a medicament for the therapeutic treatment of hypertension or prehypertension.

According to another aspect, the present invention relates to use of a compound of the present invention for the manufacture of a medicament for the therapeutic treatment of fibrosis.

According to another aspect, the present invention relates to use of a compound of the present invention for the manufacture of a medicament for the prophylactic treatment of fibrosis.

According to another aspect, the present invention relates to use of a compound of the present invention for the manufacture of a medicament for the therapeutic treatment of hypertension and fibrosis.

According to another aspect, the present invention relates to use of a compound of the present invention for the manufacture of a medicament for the therapeutic treatment of prehypertension and fibrosis.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

BRIEF DESCRIPTION OF THE FIGURES

FIG. 21: Micrographs of kidney for control rats (A) and rats treated for four weeks with 500 pmol/kg/min of T1 (B), T2 (C), T20 (D) or T31 (E).

DETAILED DESCRIPTION OF THE INVENTION

Figure 1:
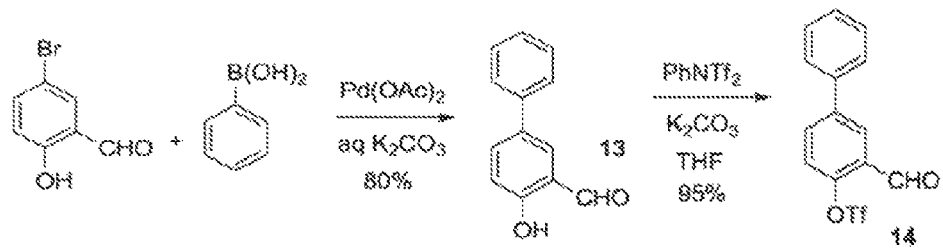
FIG. 1: Synthesis of 3-formylbiphenyl-4-yl trifluoromethanesulfonate.

The present invention relates to certain novel terphenyl compounds that show blood pressure lowering and anti-fibrotic effects in oral dosing studies in an experimental animal model. With respect to anti-fibrotic activity, the compounds of the present invention are effective in preventing fibrosis, slowing down progression of established fibrosis and/or reducing the degree (reversal) of established fibrosis. These are important findings with respect to the range and severity of conditions which can be treated with the compounds of the present invention.

The compounds of the present invention are represented by the formula:

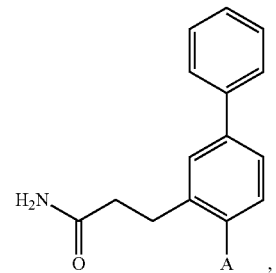

wherein:

A is selected from the group consisting of:

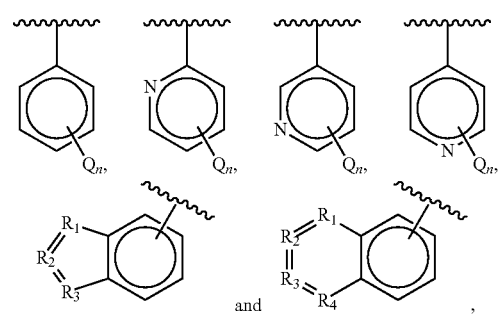

and

Q is independently selected from halo, alkyl, hydroxy, amino and substituted amino;

n is 0, 1, 2, 3, 4 or 5;

$R_1$, $R_3$ and $R_4$ are independently C, CH, $CH_2O$, N, NH or S, and $R_2$ is C, CH, $CH_2$, N, NH, C—$CF_3$, CH—$CF_3$ or C=O, or a stereoisomer or pharmaceutically acceptable salt thereof, wherein when n is 1, Q cannot be hydroxy.

The following compounds are specific, but non-limiting, examples of the compounds of the present invention:

(T1)
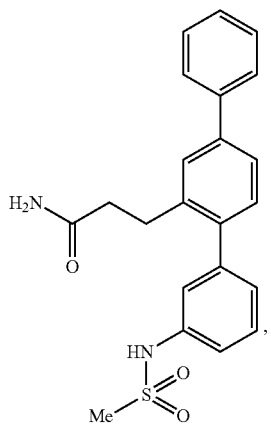
(T2)
(T3)
(T4)
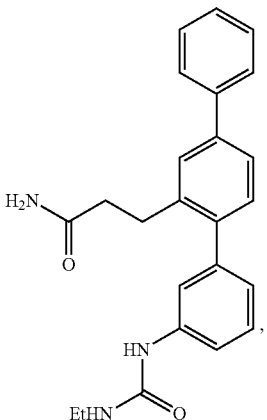
(T5)
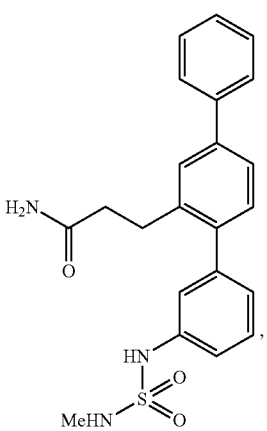
(T6)
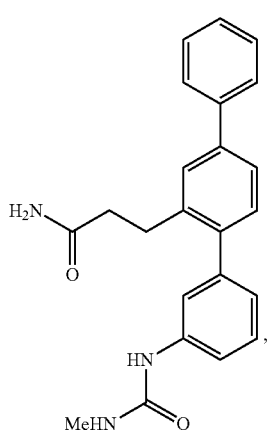

(T10)

(T11)

(T12)

(T15)

(T16)

(T18)

(T20)

(T22)

(T23) 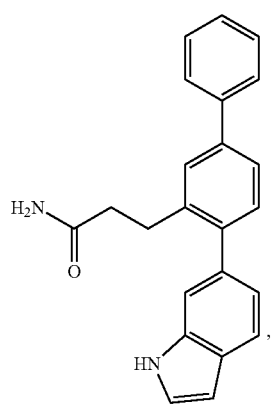
(T24) 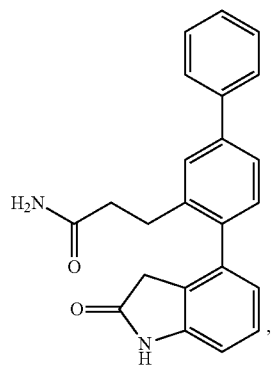
(T25) 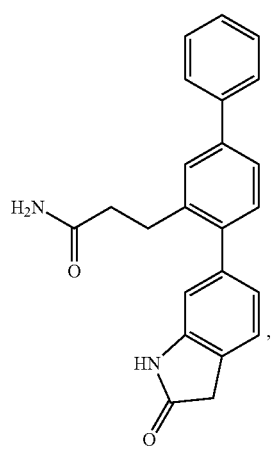
(T26) 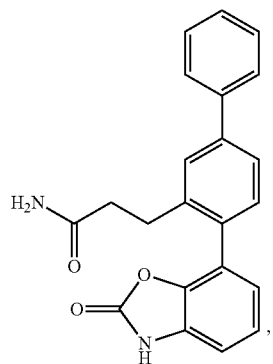
(T27) 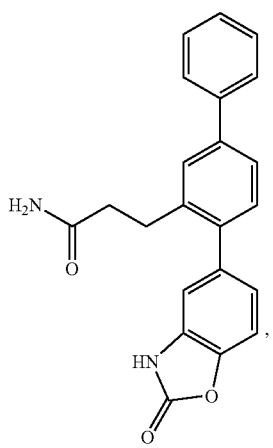
(T29) 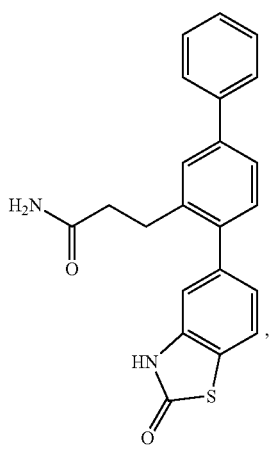
(T30) 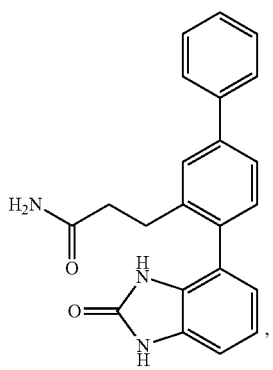

(T31) 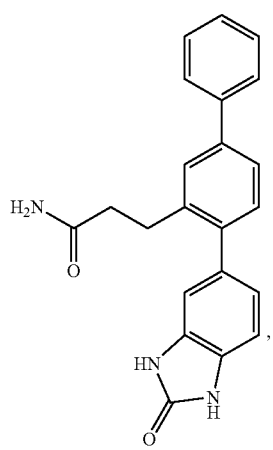
(T32) 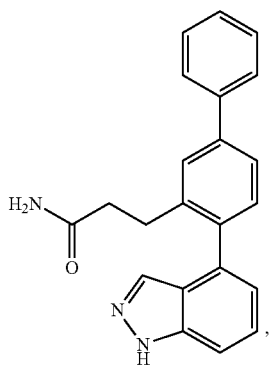
(T33) 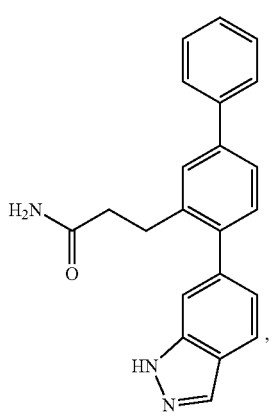
(T35) 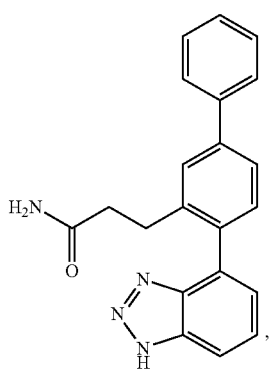
(T37) 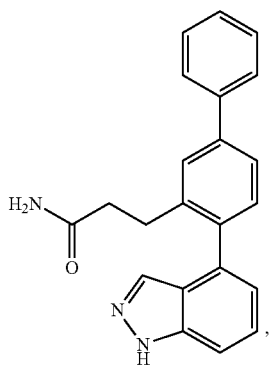
(T38) 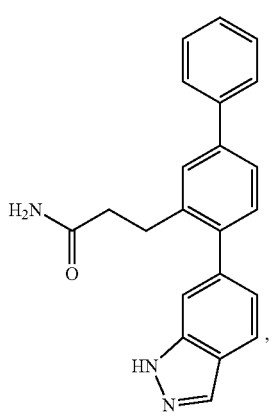
(T39) 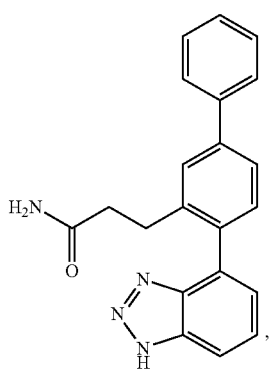
(T48) 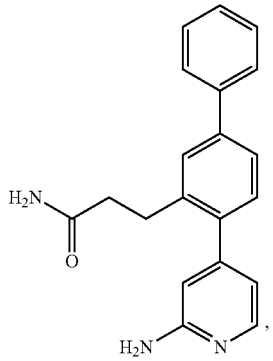

(T58)

(T66)

(T63)

(T67)

(T64)

(T68)

(T65)

(T69) and

-continued

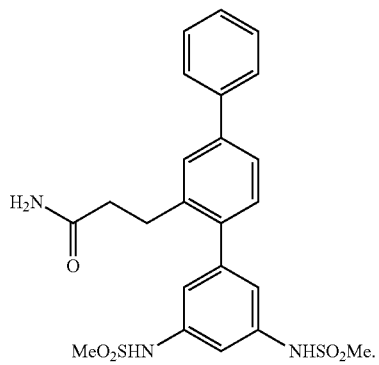

(T70)

As used herein, the term "halo" designates —F, —Cl, —Br or —I; the term "hydroxy" means —OH; the term "amino" means —NH$_2$; and the term "substituted amino" includes —NHW, wherein W is selected from —CN, —SO$_2$(X)$_a$Y and —CO(X)$_a$Y, a is 0 or 1, X is selected from —NH— and —O—, and Y is selected from —H, —CH$_3$, —CH$_2$CH$_3$, —CH$_2$OH and —CH$_2$CH$_2$OH.

As used herein, the abbreviations Me, Et, Ph, Ms represent methyl, ethyl, phenyl, and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Compounds of the present invention may exist in particular geometric or stereoisomeric forms. The present invention contemplates all such compounds, including cis- and trans-isomers, (R)- and (S)-enantiomers, diastereomers, (d)-isomers, (l)-isomers, the racemic mixtures thereof; and other mixtures thereof, as falling within the scope of the invention. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, diastereomeric salts may be formed with an appropriate optically active acid or base, followed by resolution of the diastereomers thus formed by fractional crystallization or chromatographic means well known in the art, and subsequent recovery of the pure enantiomers.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The present invention also contemplates pharmaceutically acceptable salts of the compounds. The term "pharmaceutically acceptable salt" includes both acid and base addition salts and refers to salts which retain the biological effectiveness and properties of the free bases or acids, and which are not biologically or otherwise undesirable. The to pharmaceutically acceptable salts are formed with inorganic or organic acids or bases, and can be prepared in situ during the final isolation and purification of the compounds, or by separately reacting a purified compound in its free base or acid form with a suitable organic or inorganic acid or base, and isolating the salt thus formed.

The term "fibrosis" as used in the context of the present invention includes, but is not limited to, myocardial fibrosis and/or kidney fibrosis.

In addition to treatment of established fibrosis, the compounds of the present invention may be used prophylactically in subjects at risk of developing fibrosis. As an example of subjects in the risk category for developing fibrosis are those having hypertension, diabetes, myocarditis, ischaemic heart disease, Conn's Syndrome, pheochromocytoma, genetic predisposition high salt diet and/or receiving drugs used in cancer chemotherapy (such as daunorubicin). The term "prophylactic" as used in the context of the present invention is intended inter alia to encompass treatments used to prevent or slow down the development of fibrosis in the at risk group. Subjects who may be given prophylactic treatment may already have signs of early heart failure on echocardiography.

The term "hypertension" as used in the context of the present invention indicates an adult blood pressure of above about 139 mmHg systolic and/or above about 89 mmHg diastolic.

The term "prehypertension" as used in the context of the present invention indicates an adult blood pressure in the range about 120-139 mmHg systolic and/or about 80-89 mmHg diastolic.

The present invention also contemplates pharmaceutical compositions which include the compounds of the present invention, in conjunction with acceptable pharmaceutical excipients. The term "pharmaceutically acceptable excipient" as used in the context of the present invention means any pharmaceutically acceptable inactive component of the composition. As is well known in the art, excipients include diluents, buffers, binders, lubricants, disintegrants, colorants, antioxidants/preservatives, pH-adjusters, etc. The excipients are selected based on the desired physical aspects of the final form: e.g. obtaining a tablet with desired hardness and friability being rapidly dispersible and easily swallowed etc. The desired release rate of the active substance from the composition after its ingestion also plays a role in the choice of excipients. Pharmaceutical compositions may include any type of dosage form such as tablets, capsules, powders, liquid formulations, delayed or sustained release, patches, snuffs, nasal sprays and the like. The physical form and content of the pharmaceutical compositions contemplated are conventional preparations that can be formulated by those skilled in the pharmaceutical formulation field and are based on well established principles and compositions described in, for example, Remington: The Science and Practice of Pharmacy, 19th Edition, 1995; British Pharmacopoeia 2000 and similar formulation texts and manuals.

For example, where the compounds or compositions are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means and, if desired, the active ingredient may be mixed with any conventional additive, such as an excipient, a binder, a disintegrating agent, a lubricant, a corrigent, a solubilizing agent, a suspension aid, an emulsifying agent or a coating agent.

When the compound(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The dosage of a compound and frequency of administration that should be used can also be easily determined by the practicing physician in order to produce the desired response.

Although the dosage will vary depending on the symptoms, age and body weight of the patient, the nature and severity of the disorder to be treated or prevented, the route of administration and the form of the drug, in general, a daily dosage of from 0.0001 mg to 200 mg of the compound of the present invention may be a suitable effective amount for an adult human patient, and this may be administered in a single dose or in divided doses.

A "patient" or "subject" to be treated by the subject method can mean either a human or non-human subject.

An "effective amount" of a subject compound, with respect to a method of treatment, refers to an amount of the therapeutic in a preparation which, when applied as part of a desired dosage regimen provides a benefit according to clinically acceptable standards for the treatment or prophylaxis of a particular disorder.

The present invention will now be described in more detail with reference to specific but non-limiting examples describing specific compositions and methods of use. It is to be understood, however, that the detailed description of specific procedures, compositions and methods is included solely for the purpose of exemplifying the present invention. It should not be understood in any way as a restriction on the broad description of the inventive concept as set out above.

EXAMPLES

Example 1

Synthesis of 3-formylbiphenyl-4-yl trifluoromethanesulfonate

The synthetic route used to prepare 3-formylbiphenyl-4-yl trifluoromethanesulfonate (14) is shown in FIG. 1. Briefly, a Suzuki cross-coupling reaction between 5-bromo-2-hydroxybenzaldehyde and phenylboronic acid was used to generate 2-hydroxy-5-phenyl benzaldehyde (13), which was subsequently reacted with N-phenyltriflamide to produce 3-formylbiphenyl-4-yl trifluoromethanesulfonate (14).

Production of 2-Hydroxy-5-phenylbenzaldehyde (13)

5-Bromosalicylaldehyde (2.49 g, 12.4 mmol), phenyl boronic acid (1.51 g, 12.4 mmol), palladium(II) acetate (14 mg, 0.5 mol %) and potassium carbonate (5.14 g, 37.2 mmol) were stirred in degassed water (75 mL) at ambient temperature for 2 h, under an argon atmosphere. The reaction was monitored by TLC (1:1 dichloromethane/pentane). Water (75 mL) was added and the reaction mixture acidified (pH 6) with 10% HCl, then extracted with ethyl acetate (3×). The combined organic extracts were washed with brine, then dried and concentrated. The crude material was passed through a short column of silca, eluting with 1:1 dichloromethane/pentane, then recrystallised from ethyl acetate/ pentane to afford 2-hydroxy-5-phenylbenzaldehyde (1.89 g, 77%) as dark yellow crystals (can be triturated with pentane instead recrystallised if desired); mp 100-101° C. $^1$H NMR (400 MHz, CDCl$_3$) δ 10.99 (s, 1H); 9.97 (s, 1H); 7.78-7.73 (m, 2H); 7.56-7.52 (m, 2H); 7.47-7.41 (m, 2H); 7.37-7.32 (m, 1H); 7.09-7.04 (m, 1H). $^{13}$C NMR (100 MHz, CDCl$_3$) δ 196.9, 161.2, 139.6, 136.0, 133.6, 132.1, 129.2, 127.6, 126.8, 121.0, 118.4. EIMS: m/z 198 [M]$^+$. HRMS calcd for C$_{13}$H$_{10}$O$_2$ 198.0675. Found 198.0677.

Production of 3-formylbiphenyl-4-yl trifluoromethanesulfonate (14)

2-Hydroxy-5-phenylbenzaldehyde (13) (100 mg, 0.50 mmol), N-phenyltriflimide (180.0 mg, 0.51 mmol) and potassium carbonate (209 mg, 1.51 mmol) were stirred in dry THF in a sealed tube, and heated at 120° C. for 6 min, using microwave irradiation. The solvent was removed under reduced pressure; water and dichloromethane were added and the layers separated. The aqueous layer was extracted further with dichloromethane (2×). The combined organic extracts were washed with brine (1×), then dried and concentrated. Purified by radial chromatography, eluting with 1:1 dichloromethane/pentane, to afford 3-formylbiphenyl-4-yl-trifluoromethanesulfonate (143 mg, 86%) as a clear, colourless oil. $^1$H NMR (200 MHz, CDCl$_3$) δ 10.32 (s, 1H); 8.17 (d, 1H, J=2.4 Hz); 7.89 (dd, 1H, J=8.6, 2.5 Hz); 7.63-7.36 (m, 6H). $^{13}$C NMR (125 MHz, CDCL$_3$) δ 186.5, 149.1, 142.3, 138.0, 134.1, 129.2, 129.1, 128.8, 128.6, 127.2, 122.9, 118.7 (q, J$_{CF}$=320.9 Hz). $^{19}$F NMR (188 MHz, CDCl$^3$) δ −73.2. EMS: m/z 330 [M]$^+$. HRMS calcd for C$_{14}$H$_9$F$_3$O$_2$S 330.0168. Found 330.0163.

Example 2

Synthesis of T1, T2, T10 and T18

Figure 2:
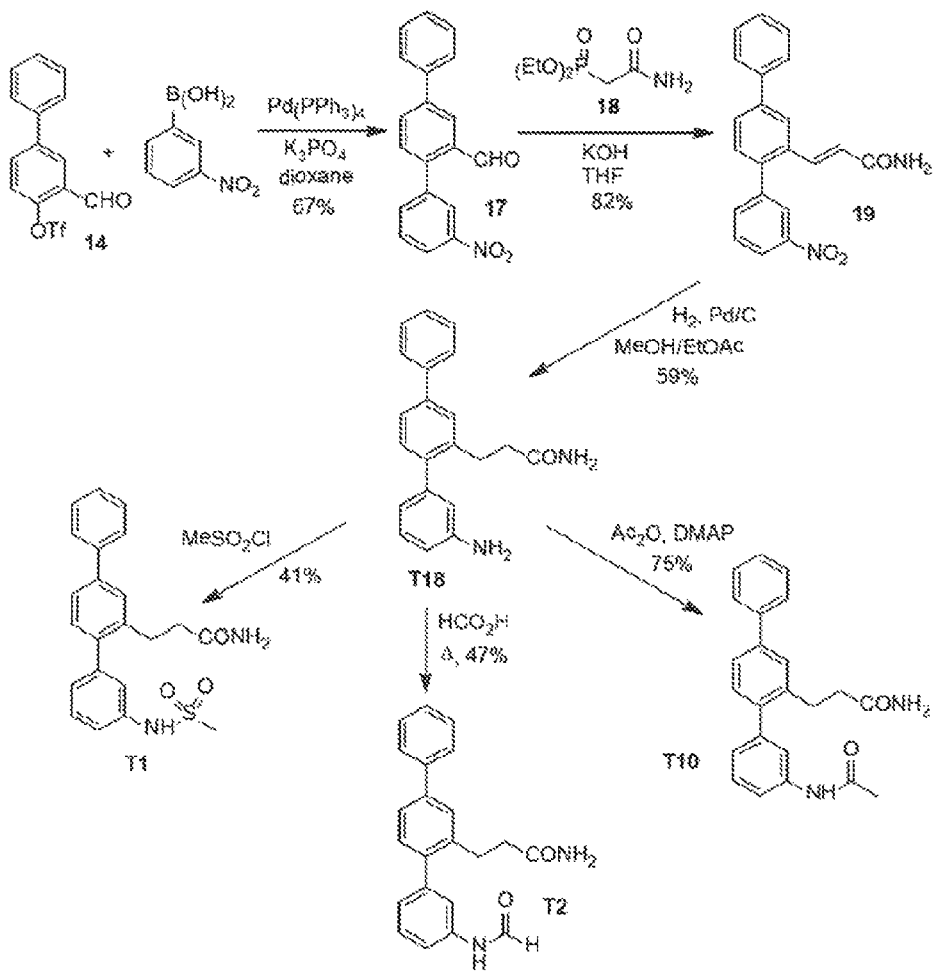
FIG. 2: Synthesis of T1, T2, T10 and T18.

The synthetic route used to prepare T1, T2, T10 and T18 is shown in FIG. 2. Briefly, 3-formylbiphenyl-4-yl trifluoromethanesulfonate (14) was cross-coupled with 3-nitrophenylboronic acid to produce nitro terphenyl (17), which then underwent a Horner-Wadsworth-Emmons reaction with diethyl(carbamoylmethyl)phosphonate (18) to produce terphenyl acrylamide (19). Hydrogenolysis of compound 19 simultaneously reduced the olefin and nitro groups to produce 3-(3-Amino-[1,1':4',1"-terphenyl]-2'-yl)propanamide (T18), which was then used to prepare 3-(3-(Methylsulfonamido)-[1,1':4',1"-terphenyl]-2'-yl)propanamide (T1) through reaction with methanesulfonyl chloride, 3-(3-Formamido-[1,1':4',1"-terphenyl]-2'-yl)propanamide (T2) through reaction with formic acid, and 3-(3-Acetamido-[1,1':4',1"-terphenyl]-2'-yl)propanamide (T10) through reaction with acetic anhydride.

Figure 3:
FIG. 3: Synthesis of diethyl(carbamoylmethyl)phosphonate.

Diethyl(carbamoylmethyl)phosphonate (18) was generated from an Arbuzov reaction between 2-chloroacetamide and triethyl phosphite (prepared as shown in FIG. 3)

Production of 3-Nitro-[1,1':4',1"-terphenyl]-2'-carbaldehyde (17)

3-formyl-[1,1'-biphenyl]-4-yl trifluoromethanesulfonate (14) (4.15 g, 12.60 mmol), 3-nitrophenylboronic acid (2.52 g, 15.10 mmol), potassium phosphate (4.01 g, 18.90 mmol) and tetrakis(triphenylphosphine)palladium(0) (0.33 g, 0.28 mmol) in dioxane (50 mL) were placed in a Schlenk flask, under an argon atmosphere. Degassed 1,4-dioxane (2 mL) was added and the mixture purged with argon. The reaction mixture was heated at 85° C. until complete conversion was observed (monitored by GCMS); generally required overnight reaction time. The crude material was purified by chromatography (DCVC) eluting with a gradient of ethyl acetate in heptane (0-25% ethyl acetate) to give 3-nitro-[1,1':4',1''-terphenyl]-2-carbaldehyde (17) as a pale tan solid (2.05 g, 67%) after recovery of un-reacted triflate (0.83 g); mp 113.6-116.3° C. (NB: Product was contaminated with ~25% by $^1$H NMR of 3,3'-dinitro-1,1'-biphenyl). $^1$H NMR (400 MHz, CDCl$_3$) δ 10.02 (s, 1H), 8.29 (m, 3H), 7.92 (dd, 1H, J 8.0, 2.1 Hz), 7.72 (m, 1H), 7.66 (m, 3H), 7.50 (m, 3H), 7.42 (m, 1H). $^{13}$C NMR (100 MHz, DMSO-d$_6$) δ 191.7, 147.8, 140.8, 140.5, 139.1, 138.4, 136.4, 133.8, 132.0, 131.9, 130.6, 129.9, 128.3, 127.0, 126.8, 124.2, 122.8. EIMS: m/z Found: M$^{+•}$ 303.0880, C$_{19}$H$_{13}$NO$_3$ requires 303.0890. EIMS: m/z 303 (M$^{+•}$, 100%), 256 (52).

Production of (E)-3-(3-Nitro-[1,1':4',1''-terphenyl]-2'-yl)acrylamide (19)

3-Nitro-[1,1':4',1''-terphenyl]-2-carbaldehyde (17) (2.35 g, 7.77 mmol) and diethyl(carbamoylmethyl)phosphonate (18) (1.51 g, 7.75 mmol) were dissolved in dry THF (100 mL), and added slowly to a vigorously stirred suspension of powdered potassium hydroxide (0.86 g, 15.40 mmol). Following stirring for 1 h at rt, the material was precipitated from the reaction mixture by addition of water and diethyl ether to give (E)-3-(3-nitro-[1,1':4',1''-terphenyl]-2'-yl)acrylamide (19) (1.8 g, 82%) as a pale lemon solid. A small portion was purified by chromatography (DCVC) eluting with a gradient of ethyl acetate in DCM (0-20% ethyl acetate) for characterisation to give (E)-3-(3-nitro-[1,1':4',1''-terphenyl]-2'-yl)acrylamide (19) as a colourless solid; mp 206-210° C. $^1$H NMR (400 MHz, DMSO-d$_6$) δ 8.35-8.28 (m, 1H), 8.18-8.15 (m, 1H), 8.02-7.98 (m, 1H), 7.85-7.76 (m, 5H), 7.56-7.41 (m, 4H), 7.49 (br s, 1H), 7.33 (d, 1H, J 15.7 Hz), 7.15 (br s, 1H), 6.78 (d, 1H, J 15.7 Hz). $^{13}$C NMR (100 MHz, DMSO-d$_6$) δ 166.2, 147.8, 140.9, 140.6, 139.1, 138.3, 136.5, 136.2, 133.4, 131.1, 130.0, 129.0, 128.0, 127.8, 126.8, 125.0, 124.8, 123.8, 122.5. EIMS: m/z Found: M$^{+•}$ 344.1153, C$_{21}$H$_{16}$N$_2$O$_3$ requires 344.1155. EIMS: m/z 344 (M$^{+•}$, 37%), 326 (50), 252 (100).

Production of 3-(3-Amino-[1,1':4',1''-terphenyl]-2'-yl)propanamide (T718)

To a solution of (E)-3-(3-nitro-[1,1':4',1''-terphenyl]-2'-yl)acrylamide (19) (1.70 g, 4.94 mmol) in methanol (50 mL) and ethyl acetate (25 mL) was added 10% palladium on carbon (50% wt water). The reaction mixture was stirred vigorously in an autoclave under hydrogen at 140 psi for 2 hours. The reaction mixture was filtered through Celite washing well with methanol and ethyl acetate. The filtrate was concentrated then pre-absorbed onto Celite and chromatographed (DCVC) eluting with a gradient of methanol in DCM (0-3% methanol). Fractions containing a single spot on TLC were combined to give 3-(3-amino-[1,1':4,1''-terphenyl]-2'-yl)propanamide (T18) as a colourless solid (0.92 g, 59%); mp 157.3-157.9° C. $^1$H NMR (400 MHz, DMSO-d$_6$) δ 7.69 (d, 2H, J 7.4 Hz), 7.59 (s, 1H), 7.51-7.46 (m, 3H), 7.37 (m, 1H), 7.23 (br s, 1H), 7.19 (d, 1H, J 7.9 Hz), 7.08 (m, 1H), 6.74 (br s, 1H), 6.57 (d, 1H, J 8.4 Hz), 6.52 (s, 1H), 6.46 (d, 1H, J 7.5 Hz), 5.13 (br s, 2H), 2.84 (m, 2H), 2.31 (m, 2H). $^{13}$C NMR (100 MHz, DMSO-d$_6$) δ 173.5, 148.5, 141.5, 141.3, 140.1, 139.1, 128.8, 130.1, 128.9, 128.7, 127.3, 127.1, 126.0, 116.5, 114.4, 112.6, 36.4, 28.3. EIMS: m/z Found: M$^{+•}$ 316.1566, C$_{21}$H$_{20}$N$_2$O requires 316.1570. EIMS: m/z 316 (M$^{+•}$, 100%). HPLC purity (40% ACN/H$_2$O, 258 nm): 100.0%.

Production of 3-(3-(Methylsulfonamido)-[1,1':4',1''-terphenyl]-2'-yl)propanamide (T1)

To a suspension of 3-(3-amino-[1,1':4,1''-terphenyl]-2'-yl)propanamide (T18) (0.50 g, 1.57 mmol) in DCM (7 mL), cooled to −5° C., was added triethylamine (0.33 mL, 2.36 mmol), followed by dropwise addition of methanesulfonyl chloride (0.21 g, 1.83 mmol) at such a rate as to maintain the temperature below 0° C. (~20 minutes). The reaction mixture was partitioned between 2M hydrochloric acid and ethyl acetate and the layers separated. The organic phase was washed again with 2M hydrochloric acid, saturated bicarbonate solution and brine. The crude material was pre-absorbed onto Celite and chromatographed (DCVC) eluting with a gradient of methanol in DCM (0-3% methanol). Like fractions were combined to give 3-(3-(methylsulfonamido){1,1':4',1''-terphenyl]-2'-yl)propanamide (T1) as colourless fine needles (0.25 g, 41%); mp 166.7-168.4° C. $^1$H NMR (400 MHz, CDCl$_3$) δ 8.12 (br s, 1H), 7.58 (m, 2H), 7.53 (m, 1H), 7.47-7.31 (m, 5H), 7.27-7.24 (m, 2H), 7.19 (m, 1H), 7.12 (m, 1H), 5.87 (br s, 1H), 5.78 (br s, 1H), 2.99, (s, 3H), 2.94 (m, 2H), 2.43 (m, 2H). $^{13}$C NMR (100 MHz. DMSO-d$_6$) δ 173.3, 141.8, 139.9 (two signals coincident), 139.5, 139.1, 138.4, 130.3, 129.3, 128.9, 127.8, 127.5, 127.4, 126.7, 124.4, 124.3, 119.9, 118.2, 39.3, 36.2, 28.3. EIMS: m/z Found: M$^{+•}$ 394.1341, C$_{22}$H$_{22}$N$_2$O$_3$S requires 394.1346. EIMS: m/z 394 (M$^{+•}$, 12%), 376 (22), 256 (100). HPLC purity (40% ACN/H$_2$O, 256 nm): 99.84%.

Production of 3-(3-Formamido-[1,1':4',1''-terphenyl]-2'-yl)propanamide (T2)

A solution of 3-(3-amino-[1,1':4,1''-terphenyl]-2'-yl)propanamide (T18) (0.41 g, 1.30 mmol) in formic acid (5 mL) was heated at reflux for 5 hours, then concentrated to dryness. The crude material was pre-absorbed onto Celite then chromatographed (DCVC) eluting with a gradient of methanol in DCM (0-5% methanol). Like fractions were combined to give 3-(3-formamido-[1,1':4,1''-terphenyl]-2'-yl)propanamide (T2) as colourless solid (0.21 g, 47%); mp 213° C. Existed as a mixture of E and Z amide isomers. $^1$H NMR (400 MHz, DMSO-d$_6$) δ 10.30 (s) and 10.22 (d, J 11.0 Hz; 1H), 8.88 (d, J 11.0 Hz) and 8.31 (d, J 1.8 Hz; 1H), 7.70 (m, 2H), 7.63-7.19 (m, 10H), 7.08 (m, 1H), 6.76 (br s, 1H), 2.83 (m, 2H), 2.32 (m, 2H). $^{13}$C NMR (50 MHz, DMSO-d$_6$) δ 173.4, 162.7, 159.7, 142.0, 141.4, 140.2, 140.0, 139.9, 139.4, 139.3, 139.1, 138.3, 138.2, 130.2, 129.3, 128.9, 128.8, 127.5, 127.3, 126.7, 124.3, 124.2, 119.6, 117.8, 117.7, 116.0, 36.2, 28.2 (a number of signals were coincident). EIMS: m/z Found: M$^{+•}$ 344.1518, C$_{22}$H$_{20}$N$_2$O$_2$ requires 344.1519. EIMS: m/z 344 (M$^{+•}$, 20%), 299 (34), 254 (100). HPLC purity (50% ACN/H$_2$O, 255 nm): 99.53%.

Production of 3-(3-Acetamido-[1,1':4',1''-terphenyl]-2'-yl)propanamide (T10)

A solution of 3-(3-amino-[1,1':4,1''-terphenyl]-2'-yl)propanamide (T18) (0.42 g, 1.33 mmol) and N,N-dimethylaminopyridine (0.04 g, cat.) in acetic anhydride (7 mL) was stirred at ambient temperature for 20 hours. The reaction mixture was partitioned between water and ethyl acetate. The layers were separated and the organic phase washed with water (2×) and brine and filtered through a plug of silica gel 60, washing well with ethyl acetate. The filtrate was concentrated to dryness and recrystallised from methanol and 1,2-dichloroethane to give 3-(3-acetamido-[1,1':4,1"-terphenyl]-2'-yl)propanamide (T10) as a beige solid (0.36 g, 75%); mp 208-209° C. $^1$H NMR (400 MHz, DMSO-$d_6$) δ 10.03 (br s, 1H), 7.70 (m, 2H), 7.62 (m, 2H), 7.58-7.47 (m, 4H), 7.40-7.35 (m, 2H), 7.23 (m, 2H), 7.02 (d, 1H, 7.7 Hz), 6.75 (br s, 1H), 2.83 (m, 2H), 2.31 (m, 2H), 2.06 (s, 3H). $^{13}$C NMR (100 MHz, DMSO-$d_6$) δ 173.4, 168.4, 141.2, 140.4, 139.9, 139.3, 139.2, 139.1, 130.2, 128.9, 128.6, 127.4, 127.3, 126.7, 124.2, 123.6, 119.4, 117.5, 36.2, 28.2, 24.1. EIMS: m/z Found: M$^{+\cdot}$ 358.1666, $C_{23}H_{22}N_2O_2$ requires 358.1676. EIMS: m/z 358 (M$^{+\cdot}$, 8%), 299 (33), 254 (100). HPLC purity (50% ACN/$H_2O$, 255 nm): 99.53%.

Example 3

Synthesis of T20

Figure 4:
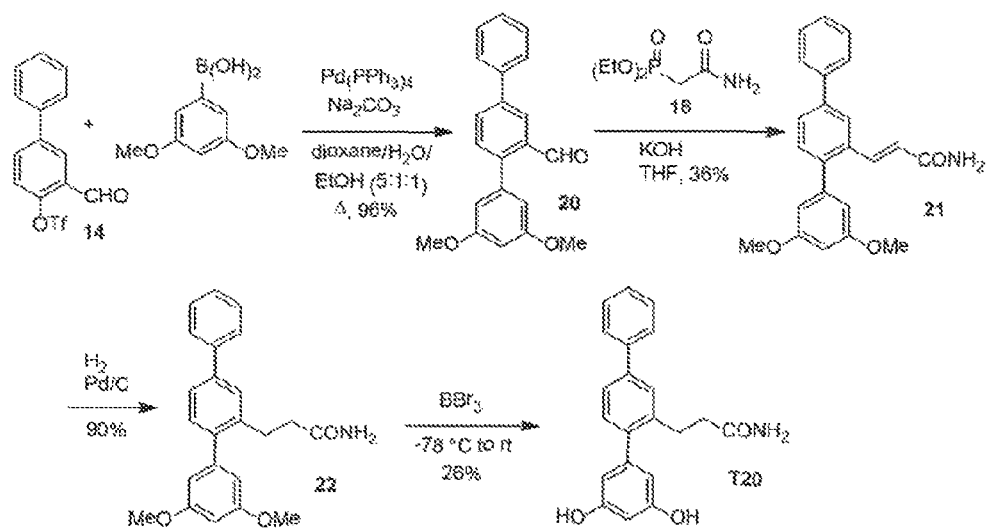
FIG. 4: Synthesis of T20.

The synthetic route used to prepare T20 is shown in FIG. 4. Briefly, 3-formylbiphenyl-4-yl trifluoromethanesulfonate (14) was cross-coupled with 3,5-dimethoxyphenylboronic acid to produce dimethoxy terphenyl (20), which then underwent a Horner-Wadsworth-Emmons reaction with diethyl (carbamoylmethyl)phosphonate (18) to afford terphenyl acrylamide (21). Hydrogenolysis of compound 21 yielded propanamide (22), which, subsequently, was demethylated using boron tribromide to afford T20.

Production of 3,5-Dimethoxy-[1,1':4',1"-terphenyl]-2'-carbaldehyde (20)

To a solution of 3,5-dimethoxyphenylboronic acid (4.0 g, 22.0 mmol), 3-formylbiphenyl-4-yl trifluoromethanesulfonate (14) (6.6 g, 20.0 mmol) and sodium carbonate (47.2 g, 40.0 mmol) in degassed dioxane/ethanol/$H_2O$ (5:1:1, 165 mL) was added tetrakis(triphenylphosphine)palladium(0) (1.16 g, 1.0 mmol). The reaction was heated at 110° C. for 2 hours in a sealed tube. Analysis by TLC (1:2 DCM/PE) indicated the triflate had been consumed. The reaction was concentrated, then taken up in water and extracted with ethyl acetate (3×). The combined organic extracts were washed with water and brine then dried (MgSO$_4$) and concentrated. The crude material was filtered through a short column of silica, eluting with 1:1 DCM:PE to afford 3,5-dimethoxy-[1,1':4',1"-terphenyl]-2'-carbaldehyde (20) (6.1 g, 96%) as a pale yellow solid. $^1$H NMR (200 MHz, CDCl$_3$) δ 10.09 (s, 1H), 8.26 (d, 1H, J 1.8 Hz), 7.87 (dd, 1H, J 2.1, 8.0 Hz), 7.68 (m, 2H), 7.58-7.35 (m, 4H), 6.56 (s, coincident, 3H), 3.84 (s, 6H). $^{13}$C NMR (50 MHz, CDCl$_3$) δ 192.4, 160.9, 144.8, 140.9, 139.6, 134.2, 132.0, 131.1, 129.1, 128.1, 127.2, 125.8, 108.6, 100.2, 55.6 (one signal not observed). EIMS: m/z Found: M$^{+\cdot}$ 318.1255, $C_{21}H_{18}O_3$ requires 318.1250. EIMS: m/z 318 (M$^{+\cdot}$, 55%).

Production of (E/Z)-3-(3,5-Dimethoxy-[1,1':4',1"-terphenyl]-2'-yl)acrylamide (21)

3,5-Dimethoxy-[1,1':4',1"-terphenyl]-2'-carbaldehyde (20) (6.1 g, 19.1 mmol) and diethyl (carbamoylmethyl) phosphonate (18) (3.7 g, 19.1 mmol) were dissolved in dry THF (180 mL), and added slowly to a vigorously stirred suspension of powdered KOH (2.1 g, 38.2 mmol) in THF (70 mL). The reaction was stirred at rt for 1 h under an argon atmosphere. Analysis by TLC (1:2 DCM:PE) indicated the carbaldehyde had been consumed. The THF was removed under reduced pressure, and the residue taken up in water and extracted with DCM (×3). The combined organic extracts were washed with brine (×1) then dried (MgSO$_4$) and concentrated to ~50 mL. The solution was filtered through a short column of silica eluting with DCM to afford (E/Z)-3-(3,5-dimethoxy-[1,1':4',1"-terphenyl]-2'-yl)acrylamide (21) (2.5 g, 36%) as an orange foam. $^1$H NMR (200 MHz, CDCl$_3$) δ 7.85 (d, 1H, J 1.7 Hz); 7.78-7.56 (m, 4H); 7.53-7.32 (m, 4H); 6.54-6.38 (m, 4H); 5.70 (brs, 2H); 3.81 (s, 6H). $^{13}$C NMR (50 MHz, CDCl$_3$) δ 167.9, 160.8, 141.8, 141.7, 141.4, 140.9, 140.5, 133.4, 130.9, 129.1, 128.4, 127.9, 127.3, 125.7, 121.5, 108.3, 100.1, 55.7. EIMS: m/z Found: M$^{+\cdot}$ 359.1504, $C_{23}H_{21}O_3N$ requires 359.1516. EIMS: m/z 359 (M$^{+\cdot}$, 3%).

Production of 3-(3,5-Dimethoxy-[1,1':4',1"-terphenyl]-2'-yl)propanamide (22)

(E/Z)-3-(3,5-Dimethoxy-[1,1':4',1"-terphenyl]-2'-yl)acrylamide (21) (2.5 g, 6.9 mmol) and 10% palladium on carbon (50% wt in $H_2O$, 1.0 g) in methanol (100 mL) were stirred at rt under a hydrogen atmosphere at 50 psi for 2 h. The reaction mixture was gravity filtered through GF paper washing thoroughly with methanol, then concentrated. The residue was then taken up in DCM and gravity filtered through GF paper, washing thoroughly with DCM, then concentrated. The crude material was then filtered through a short column of silica, washing thoroughly with DCM, then eluting the desired compound with 1:49 methanol:DCM to afford 3-(3,5-dimethoxy-[1,1':4',1"-terphenyl]-2'-yl)propanamide (22) (2.2 g, 90%) as a white solid. $^1$H NMR (200 MHz, CDCl$_3$) δ 7.70-7.24 (m, 8H); 6.50 (m, 3H); 5.78 (br s, 1H); 5.34 (br s, 1H); 3.82 (s, 6H); 3.05 (m, 2H); 2.39 (m, 2H). $^{13}$C NMR (50 MHz, CDCl$_3$) δ 174.8, 160.8, 143.3, 141.0, 140.8, 140.8, 138.6, 130.6, 129.0, 128.1, 127.6, 127.2, 125.1, 107.6, 99.2, 55.5, 37.2, 29.2. EIMS: m/z Found: M$^{+\cdot}$ 361.1672, $C_{23}H_{23}O_3N$ requires 361.1672. EIMS: m/z 361 (M$^{+\cdot}$, 100%).

Production of 3-(3,5-Dihydroxy-[1,1':4',1"-terphenyl]-2'-yl)propanamide (T20)

A solution of 3-(3,5-dimethoxy-[1,1':4',1"-terphenyl]-2'-yl)propanamide (22) (500 mg, 1.4 mmol) was dissolved in dry DCM (5 mL) and cooled to −78° C., under an argon atmosphere. Boron tribromide (2.9 mL, 2.9 mmol, 1.0 M solution in hexanes) was added and the reaction allowed to warm to rt overnight. The solution was cooled (ice/water bath) and water (5 mL) and methanol (2 mL) slowly added. The layers were separated and the aqueous phase extracted further with DCM (×2). The combined organic extracts were washed with 1.0 M sodium thiosulfate (×1), water (×1) and brine (×1), then dried (MgSO$_4$) and concentrated. Purified by radial chromatography using a gradient elution (DCM→4:96 methanol:DCM→6:94 methanol:DCM→8:92 methanol:DCM to afford 3-(3,5-dihydroxy-[1,1':4',1"-terphenyl]-2'-yl)propanamide (T20) (122 mg, 26%) as a white solid; mp 232-233° C. $^1$H NMR (200 MHz, DMSO-$d_6$) δ 9.32 (brs, 2H); 7.72-7.64 (m, 2H); 7.58 (d, 1H, J 1.8 Hz); 7.53-7.33 (m, 4H); 7.24 (overlap, brs, 1H); 7.18 (overlap, d, 1H, J 7.9 Hz); 6.75 (brs, 1H); 6.23 (t, 1H, J 2.1); 6.15 (d, 2H, J 2.1 Hz); 2.84 (m, 2H); 2.31 (m, 2H). $^{13}$C NMR (100 MHz, DMSO-$d_6$) δ 173.5, 158.1, 142.6, 140.9, 140.0, 139.0, 138.9, 129.9, 128.9, 127.3, 127.1, 126.6, 124.1, 107.1, 101.2, 36.3, 28.2. EIMS: m/z Found: M$^{+\cdot}$ 333.1344, $C_{21}H_{16}O_3N$ requires 333.1359. EIMS: m/z 333 (M$^{+\cdot}$, 94%). HPLC purity (40% ACN/$H_2O$, 264 nm): 95.97%.

Example 4

Synthesis of T70

Figure 5:
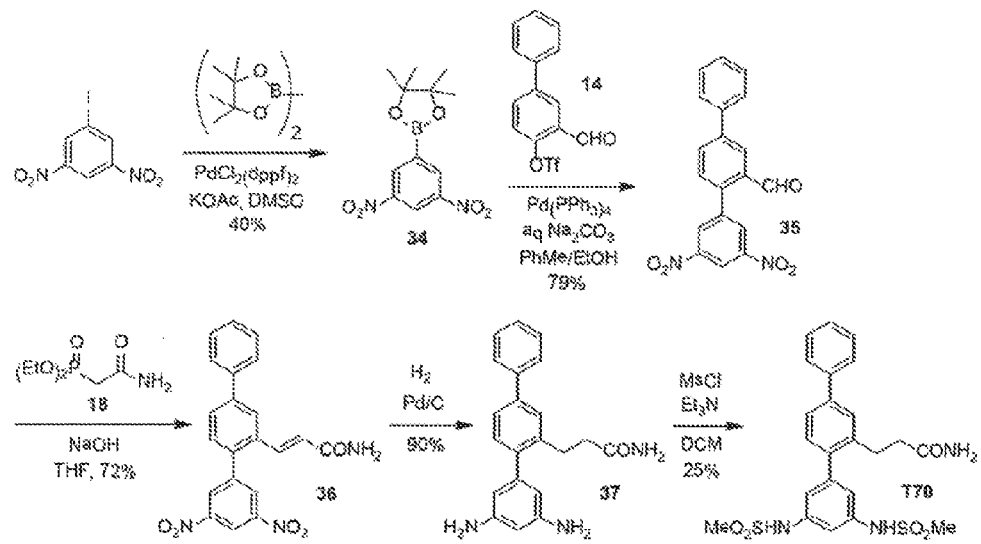
FIG. 5: Synthesis of T70.

The synthetic route used to prepare T70 is shown in FIG. 5. Briefly, 3-formyl-[1,1'-biphenyl]-4-yl trifluoromethanesulfonate (14) was cross-coupled with 3,5-dinitrophenyl pinacol boronic ester (34) [prepared from a reaction between 1-iodo-3,5-dinitrobenzene and bis(pinacolato)diborane] to provide 3,5-dinitroterphenyl (35). A subsequent Horner-Wadsworth-Emmons reaction with diethyl(carbamoylmethyl)phosphonate (18) afforded 3,5-dinitroterphenyl acrylamide (36). Compound 36 was then hydrogenated to give propanamide (37), which was reacted with methanesulfonyl chloride to produce T70.

Production of 2-(3,5-Dinitrophenyl)-4, 4, 5,5-tetramethyl-1, 3,2-dioxaborolane (34)

1-Iodo-3,5-dinitrobenzene (5.00 g, 17.00 mmol), bispinacolatodiboron (4.75 g, 18.7 mmol), potassium acetate (5.00 g, 51.00 mmol) and dichloro[1,1'-bis(diphenylphosphino)ferrocene]palladium (II) dichloromethane adduct (0.35 g, 0.48 mmol) in DMSO (80 mL) was stirred at 70° C. for 17 hours. The reaction mixture was cooled to ambient temperature, diluted with ethyl acetate then washed with saturated sodium bicarbonate solution and brine. The crude material was pre-absorbed onto Celite, then chromatographed (DCVC) eluting with a gradient of ethyl acetate in heptane (0-100% ethyl acetate). Like fractions were combined to give 2-(3,5-dinitrophenyl)-4,4,5,5-tetramethyl-1,3,2-dioxaborolane (34) as a pale yellow solid (2.10 g, 40%); mp 144.0-148.0° C. $^1$H NMR (400 MHz, CDCl$_3$) δ 9.08 (t, 1H, J 2.2 Hz), 8.90 (d, 2H, J 2.2 Hz), 1.37, (s, 12H).

Production of 3,5-Dinitro-[1,1':4',1''-terphenyl]-2'-carbaldehyde (35)

Prepared according to the method of P5; from 3-formyl-[1,1'-biphenyl]-4-yl trifluoromethanesulfonate (14) (1.77 g, 5.36 mmol), 2-(3,5-dinitrophenyl)-4,4,5,5-tetramethyl-1,3, 2-dioxaborolane (34) (1.81 g, 6.16 mmol), tetrakis(triphenylphosphine)palladium(0) (0.44 g, 0.38 mmol) and aqueous sodium carbonate (1M) (11.0 mL, 11.0 mmol) in toluene (36 mL) and ethanol (7 mL). A solid was filtered from the interface during extraction which was found to be the desired product (0.86 g, 46%). The ethyl acetate extract was purified by chromatography (DCVC) eluting with a gradient of dichloromethane in heptane (10-50% DCM) to give a further amount of 3,5-dinitro-[1,1':4',1''-terphenyl]-2'-carbaldehyde (35) as a pale tan solid (0.62 g, 33%) (Total yield: 79%); mp 209-212° C. $^1$H NMR (400 MHz, DMSO-d$_6$) δ 10.04 (s, 1H), 8.90 (s, 1H), 8.74 (s, 2H), 8.33 (s, 1H), 8.14 (d, 1H, J 8.0 Hz), 7.83 (d, 2H, J 7.3 Hz), 7.72 (d, 1H, J 8.0 Hz), 7.56 (m, 2H), 7.47 (m, 1H). $^{13}$C NMR (100 MHz, DMSO-d$_6$) δ 192.0, 147.9, 141.2, 138.2, 138.1, 134.0, 132.3, 131.8, 130.0, 129.3, 128.5 (two signals coincident), 126.9, 117.7 (one signal not observed). EIMS: m/z Found: M$^{+\cdot}$ 348.0731, C$_{19}$H$_{12}$N$_2$O$_5$ requires 348.0741. EIMS: m/z 348 (M$^{+\cdot}$, 100%).

Production of (E)-3-(3,5-Dinitro-[1,1':4',1''-terphenyl]-2'-yl)acrylamide (36)

Prepared according to the method used to generate compound 19; from 3,5-dinitro-[1,1':4',1''-terphenyl]-2'-carbaldehyde (35) (1.75 g, 5.03 mmol), diethyl(carbamoylmethyl)phosphonate (18) (1.09 g, 5.59 mmol) and sodium hydroxide (0.50 g, 12.50 mmol) in THF (70 mL). The crude solid was recrystallised from acetone to give (E)-3-(3,5-dinitro-[1,1':4',1''-terphenyl]-2'-yl)acrylamide (36) as a pale tan solid (1.40 g, 72%); mp 221-223° C. $^1$H NMR (400 MHz, DMSO-d$_6$) δ 8.90 (s, 1H), 8.58 (s, 2H), 8.02 (s, 1H), 7.85 (d, 1H, J 8.0 Hz), 7.80 (d, 2H, J 7.6 Hz), 7.64 (d, 1H, J 8.0 Hz), 7.56-7.43 (m, 4H), 7.32 (d, 1H, $^3$J$_{trans}$ 15.7 Hz), 7.16 (br s, 1H), 6.76 (d, 1H, $^3$J$_{trans}$ 15.7 Hz). $^{13}$C NMR (100 MHz, DMSO-d$_6$) δ 166.1, 148.0, 142.4, 141.3, 138.9, 136.2, 135.9, 133.8, 131.3, 129.7, 129.1, 128.2, 127.8, 126.9, 126.1, 125.3, 117.6. EIMS: m/z Found: M$^{+\cdot}$ 389.1000, C$_{21}$H$_{15}$N$_3$O$_5$ requires 389.1006. EIMS: m/z 389 (M$^{+\cdot}$, 42%), 252 (100).

Production of 3-(3,5-Diamino-[1,1':4',1''-terphenyl]-2'-yl)propanamide (37)

Prepared according to the method used to generate T18; from (E)-3-(3,5-dinitro-[1,1':4',1''-terphenyl]-2'-yl)acrylamide (36) (1.40 g, 3.60 mmol) and 10% palladium on carbon (50% wt water) (0.28 g) in methanol (40 mL). Catalyst was removed by filtration and the filtrate concentrated to dryness to give 3-(3,5-diamino-[1,1':4',1''-terphenyl]-2'-yl)propanamide (37) as a tan solid (1.07 g, 90%); mp 87.4-90.6° C. $^1$H NMR (400 MHz, DMSO-d$_6$) δ 7.68 (m, 2H), 7.65 (m, 1H), 7.49-7.45 (m, 3H), 7.36 (m, 1H), 7.22 (br s, 1H), 7.15 (d, 1H, J 7.9 Hz), 6.76 (m, 1H), 5.83 (m, 1H), 5.75 (m, 2H), 4.79 (br s, 4H), 2.86 (m, 2H), 2.31 (m, 2H). $^{13}$C NMR (100 MHz, DMSO-d$_6$) δ 173.7, 148.9, 142.2, 141.9, 140.2, 139.0, 138.4, 129.9, 128.9, 127.2, 127.0, 126.6, 123.8, 104.0, 98.7, 36.6, 28.4. EIMS: m/z Found: M$^{+\cdot}$ 331.1678, C$_{21}$H$_{21}$N$_3$O requires 331.1679. EIMS: m/z 331 (M$^{+\cdot}$, 67%), 287 (100), 273 (72).

Production of 3-(3,5-Di(methylsulfonamido)-[1,1': 4',1''-terphenyl]-2'-yl)propanamide (T70)

Prepared according to the method used to generate T1; from 3-(3,5-diamino-[1,1':4',1''-terphenyl]-2'-yl)propanamide (37) (0.46 g, 1.38 mmol), methanesulfonyl chloride (2.56 mL, 3.30 mmol) and triethylamine (0.58 mL, 4.14 mmol) in DCM (15 mL). The crude material was purified by chromatography (DCVC) eluting with a gradient of methanol in DCM (0-5% methanol) and then radial chromatography eluting with 3% methanol in DCM to give 3-(3,5-dimethylsulfonamido)-[1,1':4',1''-terphenyl]propanamide (T70) as a beige solid (0.15 g, 22%); nip 227-230° C. $^1$H NMR (400 MHz, DMSO-d$_6$) δ 9.96 (s, 2H), 7.73-7.66 (m, 2H), 7.63 (d, 1H, J 1.9 Hz), 7.55 (dd, 1H, J 1.9, 7.9 Hz), 7.52-7.45 (m, 2H), 7.42-7.36 (m, 1H), 7.26 (d, 1H, J 7.9 Hz), 7.24 (br s, 1H), 7.19-7.15 (m, 1H), 6.91 (d, 2H, J 1.9 Hz), 6.77 (br s, 1H), 3.06 (s, 6H), 2.83 (t, 2H, J 8.0 Hz), 2.32 (t, 2H, J 8.0 Hz). $^{13}$C NMR (50 MHz, DMSO-d$_6$) δ 173.3, 142.6, 139.8, 139.6, 139.5, 139.3, 139.1, 130.1, 128.9, 127.5 (two signals coincident), 126.7, 124.4, 114.8, 108.8, 39.3, 36.3, 28.3. EIMS: m/z Found: M$^{+\cdot}$ 487.1226, C$_{23}$H$_{25}$N$_3$O$_5$$^{32}$S$_2$ requires 487.1230. EIMS: m/z 487 (M$^{+\cdot}$, 4%), 408 (75), 349 (100), 271 (78). HPLC purity (40% ACN/H$_2$O, 264 nm): 94.72%.

Example 5

Synthesis of T48

Figure 6:
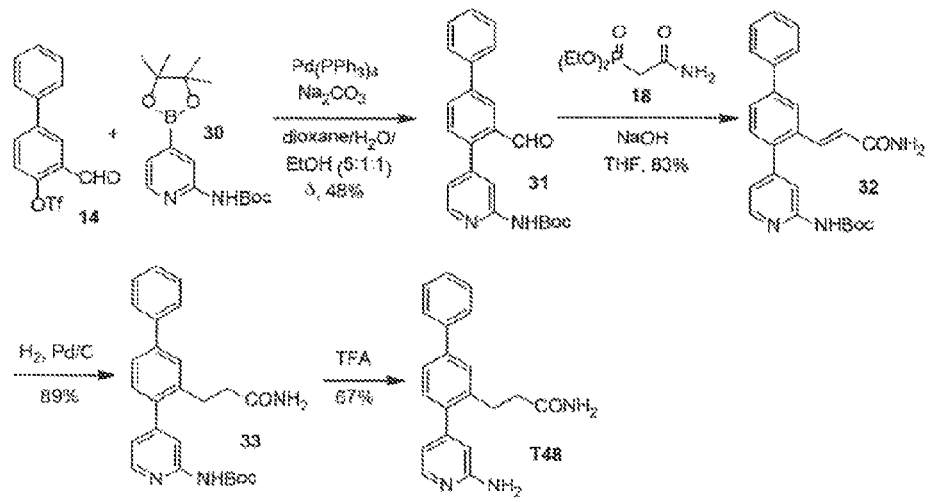
FIG. 6: Synthesis of T48.

The synthetic route used to prepare T48 is shown in FIG. 6. Briefly, 3-formyl-[1,1'-biphenyl]-4-yl trifluoromethanesulfonate (14) was cross-coupled with pyridyl pinacol boronic ester (30—Ihle, N. C.; Krause, A. E. *J. Org. Chem.* 1996, 61, 4810) to produce teraryl (31), which then underwent a Horner-Wadsworth-Emmons reaction with diethyl (carbamoylmethyl)phosphonate (18) to afford teraryl acrylamide (32). Hydrogenation of compound 32 yielded propanamide (33), which was subsequently deprotected to afford T48.

Production of tert-Butyl (4-(4,4,5,5-tetramethyl-1,3,2-dioxaborolan-2-yl)pyridin-2-yl)carbamate (30)

2-Aminopyridine-4-boronic acid pinacol ester (2.0 g, 9.1 mmol) was stirred as a suspension in tert-butanol (30 mL), under an argon atmosphere. The Boc anhydride (2.20 g, 10.0 mmol) in tert-butanol (20 mL) was added slowly, and the reaction stirred at 35° C. for 18 hours. Analysis by $^1$H NMR showed the pinacol ester starting material had been consumed. The reaction mixture was concentrated under reduced pressure, and the crude material stirred in water for 5 minutes. The solid was collected by filtration and dried in vacuo at 50° C., to afford tert-butyl (4-(4,4,5,5-tetramethyl-1,3,2-dioxaborolan-2-yl)pyridin-2-yl)carbamate (31) as a white solid (2.9 g, 98%); mp 172-178.0° C. (Lit. 188-193° C.). $^1$H NMR (200 MHz, DMSO-d$_6$) δ 9.75 (br s, 1H), 8.26 (dd, 1H, J 0.9, 4.8 Hz), 8.08 (m, 1H), 7.18 (dd, 1H, J 0.7, 4.8 Hz), 1.47 (s, 9H), 1.31 (s, 12H).

Production of tert-Butyl (4-(3-formyl-[1,1'-biphenyl]-4-yl)pyridin-2-yl)carbamate (31)

To a solution of tert-butyl (4-(4,4,5,5-tetramethyl-1,3,2-dioxaborolan-2-yl)pyridin-2-yl)carbamate (30) (2.9 g, 8.9 mmol), 3-formylbiphenyl-4-yl trifluoromethanesulfonate (14) (2.7 g, 8.1 mmol) and sodium carbonate (1.7 g, 16.2 mmol) in degassed dioxane/ethanol/H$_2$O mixture (5:1:1, 75 mL) was added tetrakis(triphenylphosphine)palladium(0) (467 mg, 0.40 mmol). The reaction was heated at 110° C. for 2 hours in a sealed tube. Analysis by $^1$H NMR indicated the triflate had been consumed. The reaction was concentrated, then taken up in DCM and poured into water. The layers were separated and the aqueous phase extracted further with DCM (2×). The combined organic extracts were washed with water (×1) and brine then dried and concentrated to approx. 20-30 mL volume. The solution was filtered through a short column of silica eluting with DCM to afford tert-butyl (4-(3-formyl-[1,1'-biphenyl]-4-yl)pyridin-2-yl)carbamate (31) as a yellow solid (1.5 g, 48%); mp 168.8-171.5° C. $^1$H NMR (200 MHz, DMSO-d$_6$) δ 10.00 (overlap s, 1H), 9.98 (overlap, br s, 1H), 8.35 (dd, 1H, J 0.7, 5.1 hz), 8.20 (d, 1H, J 1.9 Hz), 8.10 (dd, 1H, J 2.1, 8.0 Hz), 7.88 (m, 1H), 7.79 (m, 2H), 7.63 (d, 1H, J 8.0 Hz), 7.59-7.40 (m, 3H), 7.16 (dd, 1H, J 1.6, 5.1 Hz), 1.47 (s, 9H). $^{13}$C NMR (50 MHz, DMSO-d$_6$) δ 191.4, 152.8, 152.6, 147.8, 146.8, 141.2, 140.7, 138.4, 133.6, 132.0, 131.2, 129.2, 128.3, 126.8, 126.1, 119.4, 112.8, 79.7, 28.0. EIMS: m/z Found: M$^{+\cdot}$ 374.1611, C$_{23}$H$_{22}$O$_3$N$_2$ requires 374.1625. EIMS: m/z 374 (M$^{+\cdot}$, 7%), 57 (100).

Production of (E)-tert-Butyl (4-(3-(3-amino-3-oxoprop-1-en-1-yl)-[1,1'-biphenyl]-4-yl)pyridin-2-yl)carbamate (32)

Prepared according to the method used to generate compound 19; from tert-butyl (4-(3-formyl-[1,1'-biphenyl]-4-yl)pyridin-2-yl)carbamate (31) (1.44 g, 3.85 mmole), diethyl (carbamoylmnethyl)phosphonate (18) (0.75 g, 3.85 mmole) and sodium hydroxide (0.31 g, 7.70 mmol) in THF (40 mL). (E)-tert-Butyl (4-(3-(3-amino-3-oxoprop-1-en-1-yl)-[1,1'-biphenyl]-4-yl)pyridin-2-yl)carbamate (32) was precipitated from the reaction mixture upon addition of water and diethyl ether as a colourless solid (1.32 g, 83%); mp 179.5-182.2° C. $^1$H NMR (200 MHz, DMSO-d$_6$) δ 9.95 (s, 1H); 8.33 (m, 1H); 7.99 (d, 1H, J 1.6 Hz); 7.82-7.73 (m, 4H); 7.58-7.42 (m, 5H); 7.34 (d, 1H, J 15.8 hz); 7.14 (br s, 1H); 6.99 (dd, 1H, J 1.5, 5.1 Hz); 6.77 (d, 1H, J 15.7 hz); 1.46 (s, 9H). $^{13}$C NMR (50 MHz, DMSO-d$_6$) δ 166.3, 152.7, 149.0, 147.7, 140.6, 139.2, 138.7, 136.4, 133.1, 130.4, 129.0, 128.0, 127.7, 126.8, 124.6, 124.6, 119.2, 112.5, 79.7, 28.0. EIMS: m/z Found: M$^{+\cdot}$ 415.1873, C$_{22}$H$_{25}$O$_3$N$_3$ requires 415.1890. EIMS: n/z 415 (M$^{+\cdot}$, 5%), 315 (58), 297 (64), 271 (100).

Production of tert-Butyl (4-(3-(3-amino-3-oxopropyl)-[1, 1'-biphenyl]-4-yl)pyridin-2-yl)carbamate (33)

Prepared according to the method used to prepare T18; from (E)-tert-butyl (4-(3-(3-amino-3-oxoprop-1-en-1-yl)-[1, 1'-biphenyl]-4-yl)pyridin-2-yl)carbamate (32) (1.17 g, 2.80 mmol) and 10% palladium on carbon (50% wt water) (0.50 g) in methanol (75 mL). The filtrate was concentrated to give tert-butyl (4-(3-(3-amino-3-oxopropyl)-[1,1'-biphenyl]-4-yl)pyridin-2-yl)carbamate (33) as a colourless solid (1.05 g, 89%); mp 161.5-164.5° C. $^1$H NMR (400 MHz, DMSO-d$_6$) δ 9.90 (s, 1H), 8.32-8.29 (m, 1H), 7.78 (s, 1H), 7.73-7.69 (m, 2H), 7.66 (s, 1H), 7.61-7.56 (m, 1H), 7.53-7.47 (m, 2H), 7.43-7.37 (m, 1H), 7.30-7.26 (m, 1H), 7.25 (br s, 1H), 7.09-7.05 (m, 1H), 6.76 (br s, 1H), 2.88-2.81 (m, 2H), 2.36-2.29 (m, 2H), 1.47 (s, 9H). $^{13}$C NMR (50 MHz, DMSO-d$_6$) δ 173.2, 152.8, 152.6, 150.3, 147.6, 140.1, 139.7, 138.9, 138.2, 129.8, 128.9, 127.6, 127.5, 126.7, 124.5, 118.8, 112.4, 79.6, 36.1, 28.04, 28.00. EIMS: m/z Found: M$^{+\cdot}$ 417.2028, C$_{25}$H$_{27}$N$_3$O$_3$ requires 417.2047. EIMS: m/z 417 (M$^{+\cdot}$, 5%), 317 (15), 284 (89), 258 (100).

Production of 3-(4-(2-Aminopyridin-4-yl)-[1, 1'-biphenyl]-3-yl)propanamide (T48)

A mixture of tert-butyl (4-(3-(3-amino-3-oxopropyl)-[1, 1'-biphenyl]-4-yl)pyridin-2-yl)carbamate (33) (0.94 g, 2.26 mmol) and TFA (7.0 mL) in DCM (10 mL) was stirred at ambient temperature for 3 hours. The reaction mixture was partitioned with iced water to and ethyl acetate, then neutralised with sodium hydroxide (~pH 6), then basified to pH 10 with 1M sodium carbonate solution. The crude material was collected by filtration then recrystallised from methanol to give 3-(4-(2-aminopyridin-4-yl)-[1,1'-biphenyl]-3-yl)propanamide (T48) as a colourless solid (0.48 g, 67%); mp 248-249° C. $^1$H NMR (400 MHz, DMSO-d$_6$) δ 7.95 (d, 1H, J 5.2 Hz), 7.73-7.66 (m, 2H), 7.62 (s, 1H), 7.57-7.52 (m, 1H), 7.52-7.45 (m, 2H), 7.42-7.35 (m, 1H), 7.27 (br s, 1H), 7.24-7.20 (m, 1H), 6.78 (br s, 1H), 6.48 (d, 1H, J 5.2 Hz), 6.39 (s, 1H), 5.99 (s, 2H), 2.84 (t, 2H, J 7.9 Hz), 2.33 (t, 2H, J 7.9 Hz). $^{13}$C NMR (100 MHz, DMSO-d$_6$) δ 173.3, 159.9, 149.4, 147.7, 139.8, 139.7, 139.0, 138.9, 129.6, 128.9, 127.5, 127.4, 126.7, 124.4, 112.7, 107.8, 36.2, 28.1. EIMS: m/z Found: M$^{+\cdot}$ 317.1516, C$_{20}$H$_{19}$N$_3$O requires 317.1523. EIMS: m/z 317 (M$^{+\cdot}$, 12%), 273 (53), 258 (100). HPLC purity (35% ACN/0.1% TFA, 291 nm): 98.76%.

Example 6

Synthesis of T3, T11, T12 and T15 from T18

A solution of 3-(3-amino-1,1':4',1''-terphenyl-2'-yl)propanamide (T18—produced in Example 2) (1 equiv.) in dichloromethane (12.5 mL/mmol) was added to a solution of triphosgene (0.3 equiv) in dichloromethane (6.25 mL/mmol). Triethylamine (0.3 mL/mmol) was added and the mixture stirred at room temperature under nitrogen for 30 min. An amine or alcohol (2-5 equiv.) was added and the mixture stirred at room temperature under nitrogen. The neat reaction mixture was purified by flash chromatography (methanol/dichloromethane). The product was suspended in 1:1 dichloromethane/hexanes and isolated by filtration.

The following compounds were prepared by this procedure:

3-{3-[(Methylcarbamoyl)amino]-1, 1':4,1''-terphenyl-2'-yl}propanamide (T3)

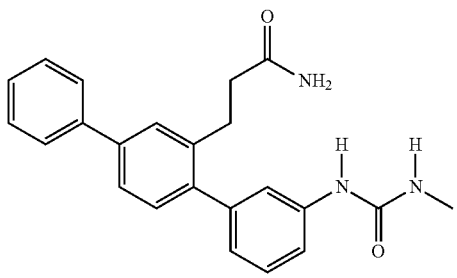 [SMILES: CNC(=O)Nc1cccc(-c2ccc(-c3ccccc3)cc2CCC(N)=O)c1]

White powder (82 mg, 27%). 1H NMR (400 MHz, DMSO-d6) 8.59 (s, 1H), 7.70 (d, J=7.2 Hz, 2H), 7.61 (d, J=1.6 Hz, 1H), 7.43-7.56 (m, 4H), 7.26-7.42 (m 3H), 7.23 (d, J=7.8 Hz, 2H), 6.87 (d, J=7.2 Hz, 1H), 6.72 (br. s., 1H), 6.06 (br. q, J=4.5 Hz, 1H), 2.79-2.87 (m, 2H), 2.64 (d. J=4.7 Hz, 3H), 2.27-2.35 (m, 2H); LCMS [M+H]+=374.2; HPLC (water/ACN+0.1% TFA gradient) 100% at 220 nm.

Methyl [2'-(3-amino-3-oxopropyl)-1, 1':4',1''-terphenyl-3-yl]carbamate (T11)

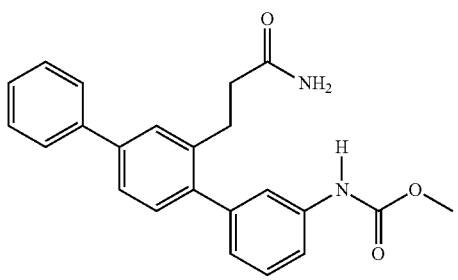 [SMILES: COC(=O)Nc1cccc(-c2ccc(-c3ccccc3)cc2CCC(N)=O)c1]

White powder (131 mg, 55%). 1H NMR (400 MHz, DMSO-d6) 9.74 (s, 1H), 7.70 (d, J=7.4 Hz, 2H), 7.62 (d, J=1.4 Hz, 1H), 7.42-7.58 (m, 5H), 7.32-7.41 (m, 2H), 7.23 (s, 2H), 6.99 (d, J=7.4 Hz, 1H), 6.73 (br. s., 1H), 3.68 (s, 3H), 2.78-2.87 (m, 2H), 2.26-2.35 (m, 2H); LCMS [M+H]+=375.3; HPLC (water/ACN+0.1% TFA gradient) 99.4% at 220 nm.

2-Hydroxyethyl [2'-(3-amino-3-oxopropyl)-1,1':4, 1''-terphenyl-2'-yl]carbamate (T12)

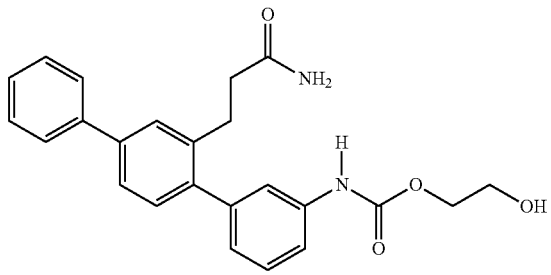 [SMILES: NC(=O)CCc1cc(-c2ccccc2)ccc1-c1cccc(NC(=O)OCCO)c1]

White powder (129 mg, 50%). 1H NMR (400 MHz, DMSO-d6) 9.79 (s, 1H), 7.70 (d, J=7.2 Hz, 2H), 7.62 (d, J=1.6 Hz, 1H), 7.42-7.58 (m, 5H), 7.31-7.41 (m, 2H), 7.15-7.27 (m, 2H), 6.98 (d, J=7.6 Hz, 1H), 6.73 (br. s., 1H), 4.81 (t, J=5.3 Hz, 1H), 4.11 (t, J=5.1 Hz, 2H), 3.63 (q, J=5.3 Hz, 2H), 2.76-2.88 (m, 2H), 2.25-2.37 (m, 2H); LCMS [M+H]+=405.1; HPLC (water/ACN+0.1% TFA gradient) 99.4% at 220 nm.

3-[3-(Carbamoylamino)-1,1':4,1''-terphenyl-2'-yl]propanamide (T15)

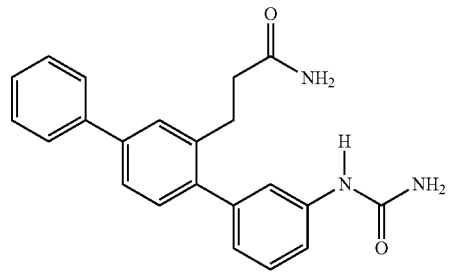 [SMILES: NC(=O)CCc1cc(-c2ccccc2)ccc1-c1cccc(NC(N)=O)c1]

White powder (74 mg, 32%). 1H NMR (400 MHz, DMSO-d6) 8.62 (s, 1H), 7.70 (d, J=7.4 Hz, 2H), 7.61 (d, J=1.6 Hz, 1H), 7.43-7.56 (m, 4H), 7.26-7.42 (m, 3H), 7.18-7.26 (m, 2H), 6.88 (d, J=7.0 Hz, 1H), 6.72 (br. s., 1H), 5.87 (s, 2H), 2.78-2.87 (m, 2H), 2.27-2.36 (m, 2H); LCMS [M+H]+=360.3; HPLC (water/ACN+0.1% TFA gradient) 97.2% at 220 nm.

Example 7

Synthesis of T4 from T18

Ethyl isocyanate (50 μL, 0.63 mmol) was added to a solution of 3-(3-amino-1,1':4',1''-terphenyl-2'-yl)propanamide (155 mg, 0.49 mmol) (T18—produced in Example 2) in dichloromethane (10 mL). The mixture was stirred at room temperature under nitrogen for 3 days. The reaction mixture was evaporated to dryness. The residue was dissolved in a mixture of dichloromethane (10 mL) and methanol (2 mL), adsorbed onto silica gel 60, and purified by flash chromatography (methanol/dichloromethane). The product was suspended in 1:1 dichloromethane/hexanes and isolated by filtration to give 3-{3-[(Ethylcarbamoyl) amino]-1,1':4', 1''-terphenyl-2'-yl}propanamide (T4):

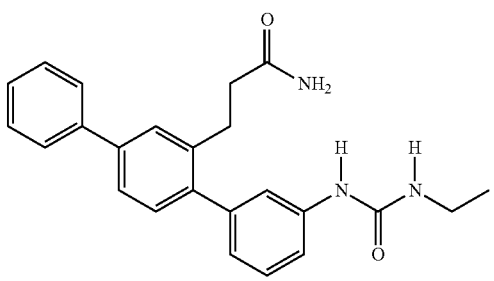 [SMILES: CCNC(=O)Nc1cccc(-c2ccc(-c3ccccc3)cc2CCC(N)=O)c1]

White powder (115 mg, 60%). 1H NMR (400 MHz, DMSO-d6) 8.50 (s, 1H), 7.70 (d, J=7.4 Hz, 2H), 7.61 (d, J=1.6 Hz, 1H), 7.42-7.57 (m, 4H), 7.25-7.42 (m, 3H), 7.18-7.26 (m, 2H), 6.87 (d, J=7.2 Hz, 1H), 6.72 (br. s., 1H), 6.14 (t, J=5.5 Hz, 1H), 3.03-3.18 (m, 2H), 2.77-2.90 (m, 2H), 2.24-2.38 (m, 2H), 1.05 (t, J=7.1 Hz, 3H); LCMS [M+H]+=388.3; HPLC (water/ACN+0.1% TFA gradient) 98.5% at 220 nm.

Example 8

Synthesis of T5 and T6 from T18

3-(3-Amino-1,1':4',1"-terphenyl-2'-yl)propanamide (T18—produced in Example 2) (1 equiv.) and triethylamine (1.3-2.0 equiv.) were dissolved in dichloromethane (18 mL/mmol). A solution of an alkylsulfamoyl chloride (1.3-2.0 equiv.) in dichloromethane (4 mL/mmol) was added drop wise. The mixture was stirred at room temperature under nitrogen for 1 h. The neat reaction mixture was purified by flash chromatography (methanol/dichloromethane). The product was suspended in 1:1 dichloromethane/hexanes to and isolated by filtration.

The following compounds were prepared by this procedure:

3-{3-[(Methylsulfamoyl)amino]-1,1':4,1"-terphenyl-2'-yl}propanamide (T5)

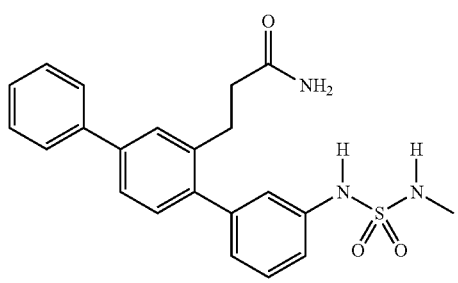 [SMILES: CNS(=O)(=O)Nc1cccc(-c2ccc(-c3ccccc3)cc2CCC(N)=O)c1]

White powder (60 mg, 30%). 1H NMR (400 MHz, DMSO-d6) 9.77 (br. s., 1H), 7.70 (d, J=7.2 Hz, 2H), 7.62 (d, J=1.6 Hz, 1H), 7.54 (dd, J=7.9, 1.7 Hz, 1H), 7.49 (t, J=7.6 Hz, 2H), 7.31-7.42 (m, 3H), 7.22-7.29 (m, 2H), 7.13-7.21 (m, 2H), 6.99 (d, J=7.6 Hz, 1H), 6.78 (br. s., 1H), 2.75-2.88 (m, 2H), 2.48 (obscured by DMSO-d6), 2.27-2.36 (m, 2H); LCMS [M+H]+=410.2; HPLC (water/ACN+0.1% TFA gradient) 97.4% at 220 nm.

3-{3-[(Ethylsulfamoyl)amino]-1,1':4',1"-terphenyl-2'-yl}propanamide (T6)

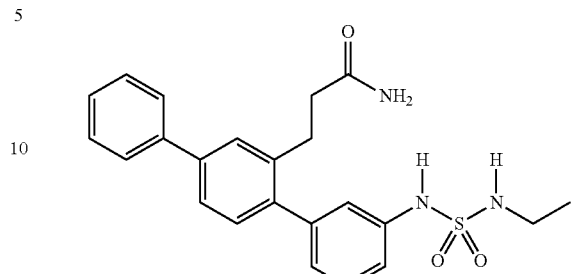

White powder (69 mg, 34%). 1H NMR (400 MHz, DMSO-d6) 9.72 (br. s., 1H), 7.70 (d, 1=7.2 Hz, 2H), 7.62 (d, J=1.6 Hz, 1H), 7.43-7.58 (m, 4H), 7.31-7.42 (m, 2H), 7.20-7.29 (m, 2H), 7.11-7.20 (m, 2H), 6.97 (d, J=7.6 Hz, 1H), 6.77 (br. s., 1H), 2.76-2.97 (m, 4H), 2.26-2.37 (m, 2H), 0.98 (t, J=7.2 Hz, 3H); LCMS [M+H]+=424.3; HPLC (water/ACN+0.1% TFA gradient) 99.6% at 220 nm.

Example 9

Synthesis of T16 from T18

3-(3-Amino-1,1':4',1"-terphenyl-2'-yl)propanamide (T18—produced in Example 2) (181 mg, 0.57 mmol) was dissolved in methanol (3.8 mL) with gentle heating. Potassium acetate (170 mg, 1.73 mmol) was added and the mixture cooled in an ice-water bath. A solution of cyanogen bromide (61 mg, 0.58 mmol) in methanol (1.1 mL) was added drop wise. The mixture was stirred in the ice-water bath under nitrogen for 1 h, then at room temperature under nitrogen overnight. The reaction mixture was evaporated to dryness. The residue was dissolved in 10% methanol/dichloromethane (60 mL). The organic phase washed with water (3×20 mL) and brine (20 mL), dried over anhydrous sodium sulfate, and filtered. The filtrate was evaporated to dryness. The residue was purified by flash chromatography (methanol/dichloromethane). The product was dissolved in ethyl acetate (20 mL) and the organic phase washed with hydrochloric acid (1 M, 3×20 mL) and brine (20 mL), dried over anhydrous sodium sulfate, and filtered. The filtrate was evaporated to dryness. The residue was suspended in 1:1 dichloromethane/hexanes and isolated by filtration. The resultant product was purified by flash chromatography (methanol/dichloromethane). The product was suspended in 1:1 dichloromethane/hexanes and isolated by filtration to give 3-[3-(Cyanoamino)-1,1':4',1"-terphenyl-2'-yl]propanamide (T16):

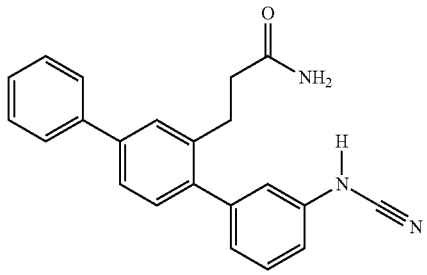 [SMILES: N#CNc1cccc(-c2ccc(-c3ccccc3)cc2CCC(N)=O)c1]

White powder (68 mg, 35%). 1H NMR (400 MHz, DMSO-d6) 10.30 (br. s., 1H), 7.70 (d, J=7.2 Hz, 2H), 7.63 (d, J=1.6 Hz, 1H), 7.55 (dd, J=7.8, 1.8 Hz, 1H), 7.35-7.52 (m, 4H), 7.20-7.30 (m, 2H), 7.04 (d, J=7.6 Hz, 1H), 6.99 (dd, J=8.0, 1.8 Hz, 1H), 6.88 (s, 1H), 6.75 (br. s., 1H), 2.82 (t, J=7.8 Hz, 2H), 2.25-2.35 (m, 2H); LCMS [M+H]+=342.3: HPLC (water/ACN+0.1% TFA gradient) 97.6% at 220 nm.

Example 10

Synthesis of 3-(3-Amino-3-oxopropyl)biphenyl-4-yl trifluoromethanesulfonate

Figure 7:
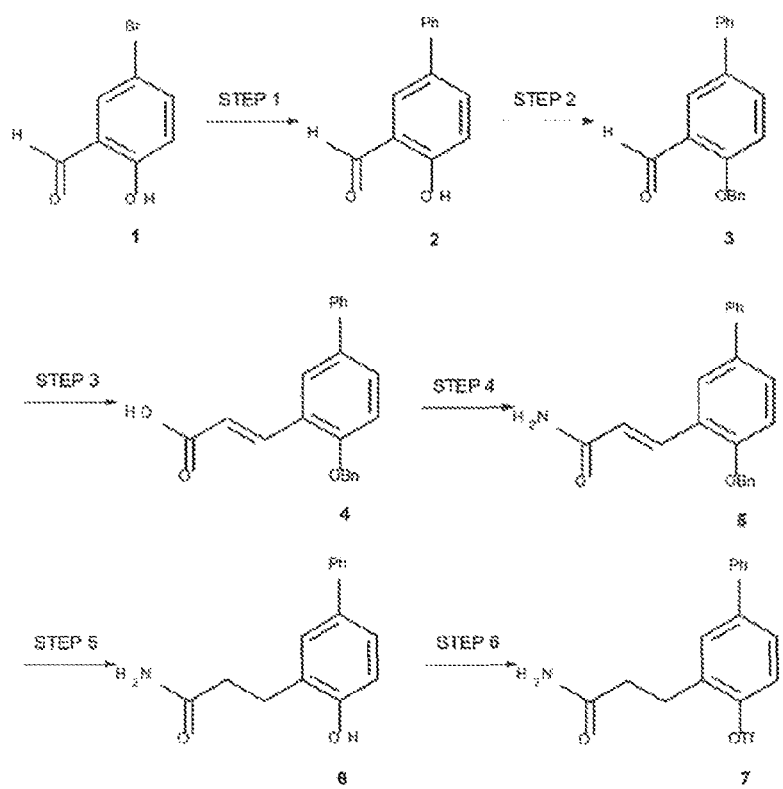
FIG. 7: Synthesis of 3-(3-amino-3-oxopropyl)biphenyl-4-yltrifluoromethanesulfonate.

The synthesis of 3-(3-Amino-3-oxopropyl)biphenyl-4-yl trifluoromethanesulfonate (7) is shown in FIG. 7.

Production of 4-Hydroxybiphenyl-3-carbaldehyde (2)

5-Bromosalicylaldehyde (1) (50.00 g, 0.249 mol), K2CO3 (103.13 g, 0.746 mol), phenylboronic acid (30.33 g, 0.249 mmol), and Pd(OAc)2 (0.28 g, 1.2 mmol) were added to a magnetically stirred 2 L round bottom flask containing freshly degassed H2O (1.5 L, degassed by purging with N2 (4×2.5 L balloons)). The reaction mixture was stirred under N2 overnight and analysed by TLC (2 observed but 1 was still present). The reaction mixture was stirred for an additional 24 h before pouring carefully into HCl (aq., 0.2M, 3 L) over several hours maintaining the pH of the mixture (~pH 2) by addition of small amounts of HCl (aq., 33%). The mixture was then stirred for 1 h with EtOAc (500 mL) and filtered through Celite into a separatory funnel. The organic layer was collected and the aqueous layer extracted with EtOAc (500 mL, washing through the Celite filtrate) and the two organic layers combined, dried over MgSO4 and concentrated to give a yellow solid residue (64 g). The residue was taken up in hot EtOH (200 mL) and H2O (200 mL) added slowly with vigorous stirring and allowed to cool to room temperature over 48 h. The resulting precipitate was collected by vacuum filtration and washed with H2O/EtOH (1:1, 200 mL) and air dried to give the crude biphenyl 2 (41.97 g, containing 25 mol % 1 as an impurity) as a pale yellow solid. The crude biphenyl 2 (39.8 g, containing approx. 0.050 mol of 1), phenylboronic acid (6.02 g, 0.050 mol) and K2CO3 (40.76 g, 0.295 mol) were added to H2O (1.0 L) in a 2 L round bottom flask with magnetic stirring. The reaction mixture was purged with N2 (2×2.5 L balloons, over 15 min) before adding Pd(OAc)2 (223 mg, 1.0 mmol) and slowly heating to reflux for 3 h under N2. Additional phenylboronic acid (1.2 g, 9.84 mmol) was added and stirring continued at reflux for 4 h, then cooled to room temperature and left to stand over the weekend. The mixture was poured into HCl (aq., 3.3 M, 1.5 L) over 1 min and stirred well for 10 min before collecting the solid by vacuum filtration and sucking to dry for 30 min. The solid was transferred to a vacuum desiccator and dried overnight to give 39.7 g of a 12:1 mixture of biphenyl 2 (mass equiv. 36.6 g, 74%) and 1 (equiv. to an 8 mol % impurity). 1H NMR (400 MHz, CDCl3) 7.08 (d, J=8.61 Hz, 1H), 7.32-7.39 (m, 1H), 7.45 (t, J=7.43 Hz, 2H), 7.55 (d, J=7.43 Hz, 2H), 7.72-7.80 (m, 2H), 9.93-10.00 (m, 1H), 11.01 (s, 1H).

Production of 4-(Benzyloxy)biphenyl-3-carbaldehyde (3)

A magnetically stirred mixture of phenol 2 (38.10 g, 0.192 mol), K2CO3 (33.78 g, 0.250 mol) and benzylbromide (29.7 mL, 0.250 mol) in CH3CN (370 mL) in a 500 mL round bottom flask was heated slowly to 70° C. for 3 h and analysed by TLC (silica, 10% EtOAc/hexane, visualised by UV). The TLC showed the reaction was progressing but some phenol 2 remained. The reaction mixture was heated to reflux for 2 h and then analysed by TLC (reaction complete, no phenol 2 observed). The reaction mixture was cooled to room temperature and transferred to a 1 L conical flask and carefully acidified with HCl (aq., 2M, 200 mL, some effervescence observed, continued until pH<2). Water was added (200 mL) and extracted with EtOAc (3×500 mL). The extracts were dried over MgSO4 and concentrated to give a light brown solid. The solid was suspended in hexane (150 mL) and stirred vigorously for 10 min before collecting the product by vacuum filtration and washing with hexane (2×60 mL) to give compound 3 as a light brown powder (44.50 g, 80%). 1H NMR (400 MHz, CDCl3) 5.25 (s, 2H), 7.13 (d, J=9.00 Hz, 1H), 7.29-7.39 (m, 2H), 7.39-7.49 (m, 6H), 7.57 (d, J=7.43 Hz, 2H), 7.77 (dd, J=8.61, 2.35 Hz, 1H), 8.10 (d, J=2.35 Hz, 1H), 10.60 (s, 1H).

Production of (2E)-3-[4-(Benzyloxy)biphenyl-3-yl] prop-2-enoic acid (4)

Piperidine (2.2 mL, 0.022 mol) was added to a magnetically stirred mixture of aldehyde (3) (44.5 g, 0.154 mol) and malonic acid (19.25 g, 0.185 mol) in pyridine (250 mL) and slowly heated to a gentle reflux for 5 h. Effervescence was noticed as the reaction temperature approached 90° C. TLC of the reaction mixture (silica, 10% EtOAc/hexane, visualised by UV) showed only a feint spot corresponding to the starting aldehyde 3 and an intense spot of fluorescent material on the baseline, corresponding to the product (4). The reaction was cooled to room temperature and concentrated on the rotovap (60° C.). EtOAc (200 mL) and HCl (aq., 2M, 200 mL) was added to give a thick slurry of white paste. The solid (compound 4) was collected by vacuum filtration and the biphasic filtrate transferred to a separatory funnel. The organic phase was collected, washed with HCl (aq., 2M, 1×100 mL), H2O (2×200 mL) and brine (1×75 mL), dried over MgSO4 and concentrated to provide additional compound 4 as a pale yellow-brown solid. The two crops of compound 4 were combined and dried in a vacuum desiccator to give compound 4 (48.5 g, 95%). 1H NMR (400 MHz, CDCl3) 5.23 (s, 2H), 6.64 (d, J=16.04 Hz, 1H), 7.03 (d, J=8.61 Hz, 1H), 7.34 (d, J=5.48 Hz, 2H), 7.38-7.49 (m, 6H), 7.55 (d, J=7.43 Hz, 3H), 7.68-7.85 (m, 1H), 8.22 (d, J=16.04 Hz, 1H).

Production of (2E)-3-[4-(Benzyloxy)biphenyl-3-yl] prop-2-enamide (5)

Oxalyl chloride (25 mL, 0.29 mol) was added slowly via a dropping funnel over 30 min to a magnetically stirred mixture of carboxylic acid 4 (48.2 g, 0.146 mol) and DMF (0.8 mL) in CH2Cl2 (500 mL) in a 1 L 3 necked round bottom flask equipped with a dropping funnel, a stopper and an oil bubbler. The temperature of the reaction was maintained by placing the vessel in a water bath for the duration of the addition. Upon addition of approximately ⅔ of the oxalyl chloride, the reaction mixture became homogenous with the disappearance of the suspended solid. The reaction mixture was allowed to stir for an additional 1 h before concentrating the reaction mixture on the rotary evaporator (60° C.) to give the intermediate acid chloride as a yellow solid. The yellow intermediate acid chloride was suspended in a magnetically stirred solution of 1,4-dioxane (200 mL)

and a solution of NH3 (31 mL, 28% in H2O, 0.438 mol) in 1,4-dioxane (200 mL) was added over 15 min. The temperature of the reaction was maintained by placing the vessel in a water bath for the duration of the addition. A thick slurry resulted. The slurry was stirred at room temperature for an additional 30 min before pouring the mixture into a 1 L conical flask and then adding H2O to give a final volume of 1 L. The slurry was stirred for 5 min and the solid collected by vacuum filtration, washing the solid with H2O (2×300 mL). The solid was dried in a vacuum desiccator overnight and then on the rotary evaporator (60° C., approx. 1-5 mmHg) to give the first crop of compound 5 (41.6 g, 86%) as an off white powder. The aqueous filtrates were concentrated to dryness, H2O (200 mL) added and the solid collected by vacuum filtration to give a second crop of compound 5 (8.12 g) as an off white powder. 1H NMR (400 MHz, CDCl3) 5.23 (s, 2H), 6.61-6.67 (m, 1H), 7.04 (d, J=8.61 Hz, 1H), 7.31-7.38 (m, 3H), 7.44 (m, 7H), 7.55 (m, 2H), 7.78 (d, J=1.57 Hz, 1H), 8.22 (d, J=16.04 Hz, 1H).

Production of 3-(4-Hydroxybiphenyl-3-yl)propanamide (6)

Compound 5 (41.55 g, 0.126 mol) was suspended in a magnetically stirred mixture of EtOAc (1 L) and NEt3 (1.5 mL). N2 (3×1 L balloons) was bubbled through the mixture before adding Pd/C (10% w/w, 4.15 g) and placing the flask under vacuum briefly before back filling the atmosphere with H2 from a balloon. The balloon was recharged with fresh H2 and opened to the reaction mixture and stirred for 6 h, recharging the balloon with H2 approximately every 1-2 h (3 times) and then stirred overnight. The balloon was again recharged with H2 and the reaction mixture slowly heated to reflux for 3 h and then cooled to room temperature and stirred under H2 for 4 days. The balloon was again recharged with H2 and the reaction mixture slowly heated to reflux for 3 h before cooling and then bubbling N2 (2×1 L balloons) through the reaction mixture. The reaction mixture was filtered through Celite, washing the Celite pad with EtOAc (2×150 mL) and the filtrate concentrated on the rotary evaporator (60° C.) to give a yellow oil. Et2O was added to the yellow oil and then removed on the rotary evaporator to give a pale yellow powder (crude 6). The TLC (silica, 70% EtOAc/hexane) of the pale yellow powder showed several products. The yellow powder was stirred vigorously in hexane (150 mL) for 30 min and the solid collected by vacuum filtration, washing with hexane (2×30 mL) to give compound 6 (30.22 g, containing approx. 15 mol % unknown impurity) as pale yellow powder. 1H NMR (400 MHz, CDCl3) 2.69-2.75 (m, 2H), 2.94-3.01 (m, 2H), 5.57 (br. s., 2H), 6.99 (d, =8.22 Hz, 1H), 7.29 (d, =2.35 Hz, 2H), 7.33-7.43 (m, 4H), 7.53 (d, J=7.43 Hz, 2H).

Production of 3-(3-Amino-3-oxopropyl)biphenyl-4-yl trifluoromethanesulfonate (7)

1,1,1-Trifluoro-N-phenyl-N-[(trifluoromethyl)sulfonyl]methanesulfonamide (PhNTf2) (42.5 g, 0.119 mol) was added to a solution of 6 (24.0 g, 0.0995 mol) and NEt3 (15.3 mL, 0.109 mol) in CH3CN (480 mL) and the reaction mixture was stirred for 1.5 h. Additional PhN(Tf)2 (2.25 g, 6.30 mmol) and NEt3 (1.5 mL, 10.7 mmol) was added and the reaction mixture stirred for a further 30 min. The reaction showed only a slight trace of remaining 6. The reaction mixture was concentrated on the rotary evaporator (60° C.) to give an orange oil. A small aliquot of the oil was taken up in EtOAc (15 mL) and washed with Na2CO3 (aq., 2M, 2×20 mL) and NaOH (aq., 0.5 M, 2×20 mL), dried over MgSO4 and concentrated to give a crop of crude 7 (422 mg). Subsequent HPLC analysis indicated the desired product was in the organic phase. This first crop of crude 7 was recombined with the orange oil and taken up in EtOAc (300 mL), washed with Na2CO3 (aq., 2M, 2×250 mL), dried over MgSO4 and concentrated on the rotary evaporator (60° C.) to give an orange oil (65 g, 1H NMR showed significant impurities including NEt3). This oil was redissolved in EtOAc (300 mL) and washed with citric acid (aq., 10% w/w, 2×250 mL) and water (2×350 mL), dried over MgSO4 and concentrated on the rotary evaporator (60° C.) to give an orange oil (59 g). This oil was again taken up in EtOAc (300 mL) and washed with NaOH (aq., 0.5 M, 3×200 mL), HCl (2M, 2×200 mL) and H2O (1×300 mL), dried over MgSO4 and concentrated on the rotary evaporator (60° C.) to give an orange oil that solidified upon standing. This solid was suspended in Et2O (150 mL) and stirred vigorously for 30 min, collected by vacuum filtration and washed with Et2O (2×30 mL) to give compound 7 as a white powder (12.3 g, 37%). 1H NMR (400 MHz, CDCl3) 2.60 (t, J=7.63 Hz, 2H), 3.13 (t, J=7.83 Hz, 2H), 5.48 (br. s., 2H), 7.32 (d, J=8.61 Hz, 1H), 7.36-7.42 (m, 1H), 7.45 (t, J=7.43 Hz, 2H), 7.50 (dd, J=8.61, 1.96 Hz, 1H), 7.54 (d, J=7.43 Hz, 2H), 7.59 (d, J=1.96 Hz, 1H).

Example 11

Synthesis of T22 and T23

T22 and T23 were prepared from 3-(3-Amino-3-oxopropyl)biphenyl-4-yl trifluoromethanesulfonate (7—produced in Example 10). A mixture of 7 (1 equiv.), a heterocyclic boronic acid (1.2 equiv.) and potassium carbonate (2 equiv.) was suspended in 1,4-dioxane (4 mL/mmol) and water (5 drops/mmol). Nitrogen was bubbled through the mixture for 15 min. Tetrakis(triphenylphosphine)palladium(0) (0.1 equiv) was added and the mixture heated at 85° C. under nitrogen for 20 h. The mixture was diluted with ethyl acetate and filtered. The residue was washed with ethyl acetate (2×). The combined filtrates were evaporated to dryness and purified by flash chromatography (methanol/dichloromethane). The product was suspended in hexanes (4 mL) and isolated by filtration.

The following compounds were prepared by this procedure:

3-[4-(1H-Indol-4-yl)biphenyl-3-yl]propanamide (T22)

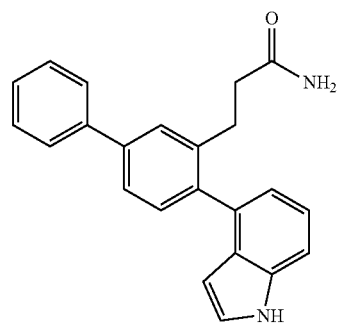 [SMILES: NC(=O)CCc1cc(-c2ccccc2)ccc1-c1cccc2[nH]ccc12]

Pale beige powder (58 mg, 32%). 1H NMR (400 MHz, CDCl3) 8.27 (br. s., 1H), 7.64-7.71 (m, 2H), 7.58-7.63 (m, 1H), 7.54 (dd, J=7.8, 1.8 Hz, 1H), 7.40-7.50 (m, 4H), 7.36 (br. t, 1=7.5 Hz, 1H), 7.28 (d, J=8.2 Hz, 1H), 7.22 (t, J=2.7 Hz, 1H), 7.03-7.09 (m, 1H), 6.27-6.33 (m, 1H), 4.96 (hr. s., 1H), 4.88 (br. s., 1H), 2.99 (br. s., 2H), 2.23 (t, J=7.9 Hz, 2H); LCMS [M+H]+=341.2; HPLC (water/ACN+0.1% TFA gradient) 97.1% at 220 nm 3-[4-(1H-Indol-6-yl)biphenyl-3-yl]propanamide (T23)

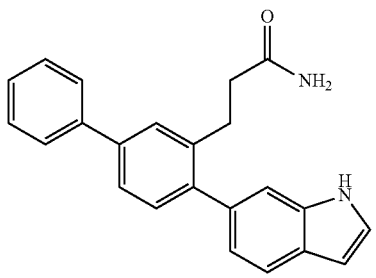 [SMILES: NC(=O)CCc1cc(-c2ccccc2)ccc1-c1ccc2cc[nH]c2c1]

Pale brown powder (13 mg, 7%). 1H NMR (400 MHz, CDCl3) 8.27 (br. s., 1H), 7.69 (d, J=8.0 Hz, 1H), 7.64 (d, J=7.2 Hz, 2H), 7.56 (d, J=1.6 Hz, 1H), 7.47-7.53 (m, 1H), 7.42-7.46 (m, 2H), 7.32-7.41 (m, 3H), 7.12 (dd, J=8.1, 1.3 Hz, 1H), 6.60 (br. s., 1H), 5.06 (br. s., 2H), 3.04-3.16 (m, 2H), 2.29-2.40 (m, 2H); LCMS [M+H]+=341.3; HPLC (water/ACN+0.1% TFA gradient) 99.5% at 220 nm.

Example 12

Synthesis of T29, T38, T63, T64, T65 and T66

T29, T38, T63, T64, T65 and T66 were prepared from 3-(3-Amino-3-oxopropyl) biphenyl-4-yl trifluoromethanesulfonate (7—produced in Example 10). A mixture of 7 (1 equiv.), an aromatic boronic acid or heterocyclic boronic acid pinacol ester (1.1 equiv.), and potassium carbonate (2-3 equiv.) was dissolved in a mixture of 1,4-dioxane (3.1 mL/mmol), ethanol (0.65 mL/mmol) and water (0.65 mL/mmol). Nitrogen was bubbled through the mixture for 10 min. Tetrakis(triphenylphosphine)palladium(0) (0.1 equiv) was added and the mixture heated at 85° C. under nitrogen for 20 h. The mixture was partitioned between ethyl acetate and water. The aqueous phase was extracted with ethyl acetate. The combined ethyl acetate extracts were washed with water and brine, dried over anhydrous sodium sulfate, and filtered. The filtrate was evaporated to dryness and purified by flash chromatography (methanol/dichloromethane). The product was suspended in 1:1 dichloromethane/hexanes and isolated by filtration The following compounds were prepared by this procedure:

3-[4-(2-Oxo-2,3-dihydro-1,3-benzothiazol-5-yl)biphenyl-3-yl]propanamide (T29)

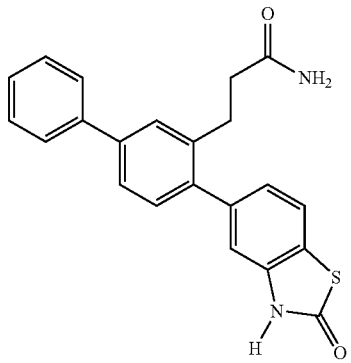 [SMILES: NC(=O)CCc1cc(-c2ccccc2)ccc1-c1ccc2sc(=O)[nH]c2c1]

Light brown powder (39 mg, 11%). 1H NMR (400 MHz, DMSO-d6) 11.96 (br. s., 1H), 7.70 (d, J=7.2 Hz, 2H), 7.60-7.67 (m, 2H), 7.55 (dd, J=7.9, 1.7 Hz, 1H), 7.49 (t, J=7.6 Hz, 2H), 7.35-7.43 (m, 1H), 7.20-7.31 (m, 2H), 7.09-7.16 (m, 1H), 7.05 (d, J=1.2 Hz, 1H), 6.75 (br. s., 1H), 2.84 (t, J=7.8 Hz, 2H), 2.25-2.37 (m, 2H); LCMS [M+H]+=375.1; HPLC (water/ACN+0.1% TFA gradient) 98.6% at 220 nm.

3-[4-(1H-Indazol-6-yl)biphenyl-3-yl]propanamide (T38)

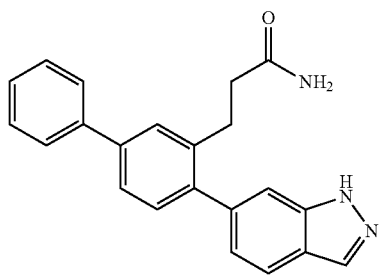 [SMILES: NC(=O)CCc1cc(-c2ccccc2)ccc1-c1ccc2cn[nH]c2c1]

Pale yellow powder (72 mg, 44%). 1H NMR (400 MHz, DMSO-d6) 13.09 (s, 1H), 8.12 (s, 1H), 7.82 (d, J=8.2 Hz, 1H), 7.71 (d, J=7.4 Hz, 2H), 7.65 (d, J=1.4 Hz, 1H), 7.56 (dd, J=8.0, 1.8 Hz, 1H), 7.43-7.53 (m, 3H), 7.35-7.43 (m, 1H), 7.32 (d, J=7.8 Hz, 1H), 7.21 (br. s., 1H), 7.11 (dd, J=8.3, 0.9 Hz, 1H), 6.70 (br. s., 1H), 2.77-2.93 (m, 2H), 2.25-2.38 (m, 2H); LCMS [M+H]+=342.1; HPLC (water/ACN+0.1% TFA gradient) 98.5% at 220 nm.

3-(2-Fluoro-3-hydroxy-1,1':4',1''-terphenyl-2'-yl)propanamide (T63)

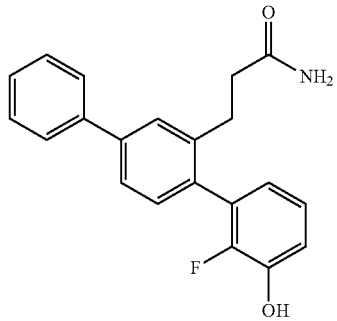 [SMILES: NC(=O)CCc1cc(-c2ccccc2)ccc1-c1cccc(O)c1F]

White powder (87 mg, 53%). 1H NMR (400 MHz, DMSO-d6) 9.92 (br. s., 1H), 7.70 (d, J=7.2 Hz, 2H), 7.64 (d, J=1.6 Hz, 1H), 7.54 (dd, f=7.9, 1.7 Hz, 1H), 7.49 (t, J=7.6 Hz, 2H), 7.35-7.42 (m, 1H), 7.16-7.29 (m, 2H), 7.03-7.10 (m, 1H), 6.94-7.02 (m, 1H), 6.65-6.78 (m, 2H), 2.72 (t, J=7.8 Hz, 2H), 2.28 (t, J=7.9 Hz, 2H); LCMS [M+H]+=336.2; HPLC (water/ACN+0.1% TFA gradient) 99.3% at 220 nm.

3-(4-Fluoro-3-hydroxy-1,1':4',1''-terphenyl-2'-yl)propanamide (T64)

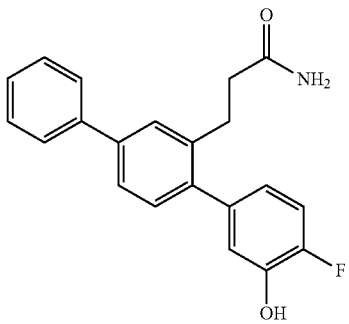 [SMILES: NC(=O)CCc1cc(-c2ccccc2)ccc1-c1ccc(F)c(O)c1]

White powder (98 mg, 61%). 1H NMR (400 MHz, DMSO-d6) 9.95 (br. s., 1H), 7.69 (d, J=7.2 Hz, 2H), 7.60 (d, J=1.6 Hz, 1H), 7.43-7.55 (m, 3H), 7.33-7.42 (m, 1H), 7.12-7.28 (m, 3H), 6.90 (dd, J=8.5, 2.1 Hz, 1H), 6.65-6.80 (m, 2H), 2.76-2.87 (m, 2H), 2.25-2.36 (nm, 2H); LCMS [M+H]+=336.2; HPLC (water/ACN+0.1% TFA gradient) 99.6% at 220 nm.

3-(3-Fluoro-5-hydroxy-1,1':4',1''-terphenyl-2'-yl)propanamide (T65)

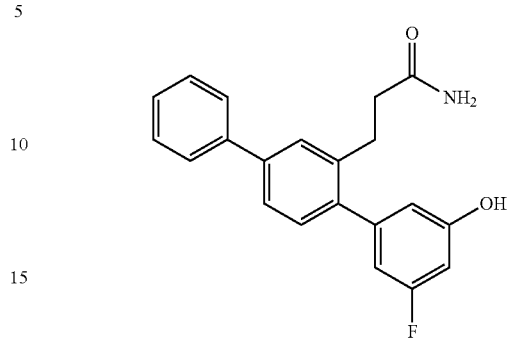

White powder (89 mg, 55%). 1H NMR (400 MHz, DMSO-d6) 10.05 (br. s., 1H), 7.69 (d, J=7.4 Hz, 2H), 7.61 (d, J=1.6 Hz, 1H), 7.44-7.56 (m, 3H), 7.34-7.42 (m, 1H), 7.20-7.31 (m, 2H), 6.76 (br. s., 1H), 6.54-6.64 (m, 3H), 2.83 (t, J=7.8 Hz, 2H), 2.32 (t, J=7.8 Hz, 2H); LCMS [M+H]+=336.2; HPLC (water/ACN+0.1% TFA gradient) 99.6% at 220 nm.

3-(2-Fluoro-5-hydroxy-1,1':4',1''-terphenyl-2'-yl)propanamide (T66)

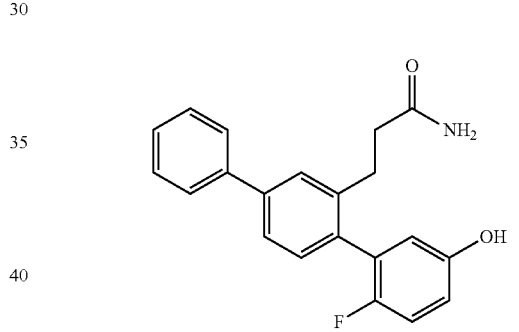

White powder (75 mg, 45%). 1H NMR (400 MHz, DMSO-d6) 9.51 (s, 1H), 7.70 (d, J=7.2 Hz, 2H), 7.63 (d, J=1.4 Hz, 1H), 7.54 (dd, J=7.9, 1.7 Hz, 1H), 7.49 (t, =7.5 Hz, 2H), 7.35-7.42 (m, 1H), 7.19-7.29 (m, 2H), 7.10 (t, J=9.1 Hz, 1H), 6.79 (dt, J=8.6, 3.6 Hz, 1H), 6.74 (br. s., 1H), 6.66 (dd, J=6.3, 2.9 Hz, 1H), 2.68-2.78 (m, 2H), 2.24-2.34 (m, 2H); LCMS [M+H]+=336.2; HPLC (water/ACN+0.1% TFA gradient) 97.6% at 220 nm.

Example 13

Synthesis of 3-[4-(4,4,5,5-Tetramethyl-1,3,2-dioxoborolan-2-yl)biphenyl-3-yl]propanamide 3-[4-(4,4,5,5-Tetramethyl-1,3,2-dioxoborolan-2-yl)biphenyl-3-yl]propanamide (8) was prepared from 3-(3-Amino-3-oxopropyl) biphenyl-4-yl trifluoromethanesulfonate (7—produced in Example 10). A mixture of 7 (1.81 g, 4.84 mmol), bis(pinacolato)diboron (1.35 g, 5.31 mmol), 1,1'-bis(diphenylphosphino)ferrocenepalladium(II) dichloride dichloromethane complex (790 mg, 0.97 mmol) and potassium acetate (1.43 g, 14.5 mmol) were suspended in anhydrous dimethylsulfoxide (31 mL) under nitrogen. The mixture was heated at 85° C. under nitrogen for 4 h. The mixture was diluted with ethyl acetate (90 mL) and eluted through a silica gel column with ethyl acetate. The fractions that contained the major band were washed with water (2×200 mL) and brine (200 mL), dried over anhydrous sodium sulfate, and filtered. The filtrate was evaporated to dryness. The residue was purified by flash chromatography (ethyl acetate/dichloromethane) to give compound 8:

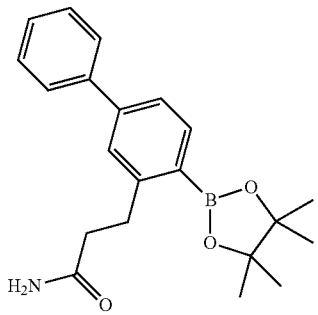 [SMILES: CC1(C)OB(c2ccc(-c3ccccc3)cc2CCC(N)=O)OC1(C)C]

A light brown oil that solidified on standing (1.02 g, 59%). 1H NMR (400 MHz, CDCl3) 7.91 (d, J=8.4 Hz, 1H), 7.60 (d, J=7.2 Hz, 2H), 7.40-7.50 (m, 4H), 7.32-7.39 (m, 1H), 5.82 (br. s., 1H), 5.33 (br. s., 1H), 3.22-3.31 (m, 2H), 2.51-2.59 (m, 2H), 1.38 (s, 12H).

Example 14

Synthesis of T24, T26, T27, T30, T32, T33, T35, T37, T39 and T58

T24, T26, T27, T30, T32, T33, T35, T37, T39 and T58 were prepared from 3-[4-(4,4,5,5-Tetramethyl-1,3,2-dioxoborolan-2-yl)biphenyl-3-yl]propanamide (8—produced in Example 13). A mixture of 8 (1 equiv.), a bromo-aromatic or bromo-heterocycle (1.1 equiv.) and 1,1'-bis(diphenylphosphino)-ferrocenepalladium(II) dichloride dichloromethane complex (0.1 equiv.) was dissolved in anhydrous N,N-dimethylfornamide (10.6 mL/mmol) under nitrogen. A degassed sodium carbonate solution (2 M, 5.3 mL/mmol) was added. The mixture was heated at 80° C. under nitrogen. The mixture was partitioned between ethyl acetate and water. The aqueous phase was extracted with ethyl acetate. The combined ethyl acetate extracts were washed with water (3×) and brine, dried over anhydrous sodium sulfate, and filtered. The filtrate was evaporated to dryness and purified by flash chromatography (methanol/dichloromethane). The product was suspended in 1:1 dichloromethane/hexanes and isolated by filtration The following compounds were prepared by this procedure:

3-[4-(2-Oxo-2,3-dihydro-1H-indol-4-yl)biphenyl-3-yl]propanamide (T24)

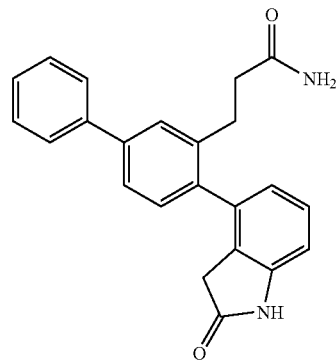 [SMILES: NC(=O)CCc1cc(-c2ccccc2)ccc1-c1cccc2c1CC(=O)N2]

Pale yellow powder (72 mg, 58%). 1H NMR (400 MHz, DMSO-d6) 10.46 (s, 1H), 7.70 (d, J=7.2 Hz, 2H), 7.63 (d, J=1.4 Hz, 1H), 7.43-7.56 (m, 3H), 7.34-7.42 (m, 1H), 7.16-7.30 (m, 3H), 6.83 (t, J=7.3 Hz, 2H), 6.67 (br. s., 1H), 3.26 (br. s., 2H), 2.72 (br. t, J=7.0 Hz, 2H), 2.25 (t, J=7.7 Hz, 2H); LCMS [M+H]+=357.2; HPLC (water/ACN+0.1% TFA gradient) 100.0% at 220 nm.

3-[4-(2-Oxo-2,3-dihydro-1,3-benzoxazol-7-yl)biphenyl-3-yl]propanamide (T26)

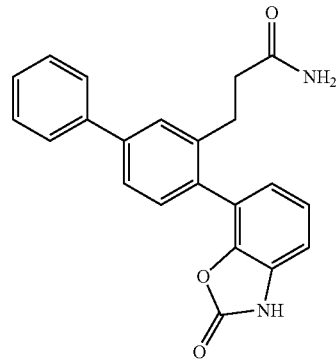 [SMILES: NC(=O)CCc1cc(-c2ccccc2)ccc1-c1cccc2[nH]c(=O)oc12]

Light orange powder (30 mg, 23%). 1H NMR (400 MHz. DMSO-d6) 11.72 (br. s., 1H), 7.70 (d, J=7.4 Hz, 2H), 7.65 (s, 1H), 7.56 (dd, J=7.8, 1.2 Hz, 1H), 7.48 (t, J=7.6 Hz, 2H), 7.34-7.42 (m, 1H), 7.31 (d, J=7.8 Hz, 1H), 7.15-7.26 (m, 2H), 7.10 (d, J=7.0 Hz, 1H), 7.02 (d, J=7.4 Hz, 1H), 6.69 (br. s., 1H), 2.75 (t, J=8.0 Hz, 21H), 2.26 (t, J=8.0 Hz, 2H); LCMS [M+H]+=359.1; HPLC (water/ACN+0.1% TFA gradient) 98.9% at 220 nm.

3-[4-(2-Oxo-2,3-dihydro-1,3-benzoxazol-5-yl)biphenyl-3-yl]propanamide (T27)

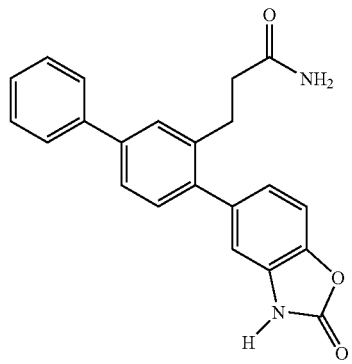 [SMILES: NC(=O)CCc1cc(-c2ccccc2)ccc1-c1ccc2oc(=O)[nH]c2c1]

Pale orange powder (49 mg, 28%). 1H NMR (400 MHz, DMSO-d6) 11.69 (br. s., 1H), 7.70 (d, J=7.4 Hz, 2H), 7.62 (d, J=1.6 Hz, 1H), 7.45-7.57 (m, 3H), 7.31-7.43 (m, 2H), 7.17-7.30 (m, 2H), 7.00-7.09 (m, 2H), 6.72 (br. s., 1H), 2.83 (t, J=7.8 Hz, 2H), 2.25-2.35 (m, 2H); LCMS [M+H]+=359.2; HPLC (water/ACN+0.1% TFA gradient) 97.0% at 220 nm.

3-[4-(2-Oxo-2,3-dihydro-1H-benzimidazol-4-yl)biphenyl-3-yl]propanamide (T30)

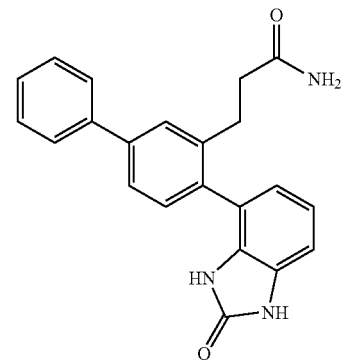 [SMILES: NC(=O)CCc1cc(-c2ccccc2)ccc1-c1cccc2[nH]c(=O)[nH]c12]

Light beige powder (110 mg, 63%). 1H NMR (400 MHz, DMSO-d6) 10.69 (s, 1H), 10.48 (s, 1H), 7.71 (d, J=7.4 Hz, 2H), 7.63 (d, J=1.6 Hz, 1H), 7.55 (dd, J=7.8, 1.8 Hz, 1H), 7.50 (t, J=7.6 Hz, 2H), 7.35-7.43 (m, 1H), 7.19-7.30 (m, 2H), 6.97-7.05 (m, 1H), 6.91-6.97 (m, 1H), 6.78-6.82 (m, 1H), 6.75 (br. s., 1H), 2.60-2.86 (m, 2H), 2.29 (br. s., 2H); LCMS [M+H]+=358.2; HPLC (water/ACN+0.1% TFA gradient) 96.4% at 220 nm.

3-[4-(2-Oxo-1,2,3,4-tetrahydroquinolin-7-yl)biphenyl-3-yl]propanamide (T32)

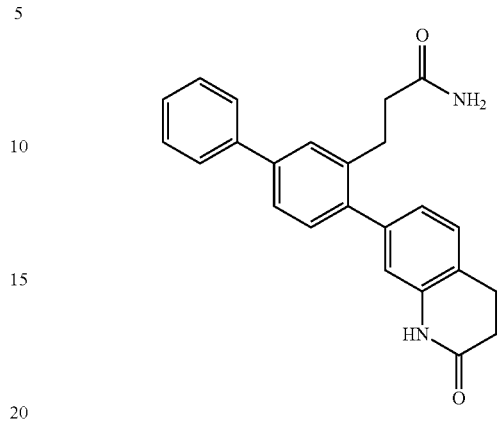

Pale beige powder (118 mg, 66% yield). 1H NMR (400 MHz, DMSO-d6) 10.13 (s, 1H), 7.69 (d, J=7.4 Hz, 2H), 7.61 (d, J=1.6 Hz, 1H), 7.44-7.56 (m, 3H), 7.34-7.41 (m, 1H), to 7.18-7.28 (m, 3H), 6.90 (dd, J=7.5, 1.5 Hz, 1H), 6.82 (d, J=1.2 Hz, 1H), 6.74 (br. s., 1H), 2.94 (t, J=7.5 Hz, 2H), 2.77-2.87 (m, 2H), 2.53 (obscured by DMSO-d6), 2.28-2.37 (m, 2H); LCMS [M+H]+=371.2; HPLC (water/ACN+0.1% TFA gradient) 97.9% at 220 nm.

3-{4-[2-(Trifluoromethyl)-1H-benzimidazol-4-yl]biphenyl-3-yl}propanamide (T33)

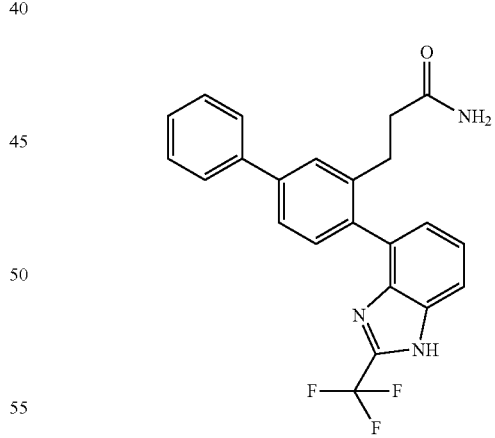

White powder (107 mg, 53%). 1H NMR (400 MHz, DMSO-d6) 13.81-14.10 (m, 1H), 7.08-7.88 (m, 12H), 6.59-6.81 (m, 1H), 2.71 (br. t, J=7.3 Hz, 2H), 2.28 (m, 2H), Spectrum was split into two species due to hydrogen exchange on the benzimidazole moiety; LCMS [M+H]++=410.2; HPLC (water/ACN+0.1% TFA gradient) 100% at 220 nm.

3-[4-(1H-Benzimidazol-4-yl)biphenyl-3-yl]propanamide (T35)

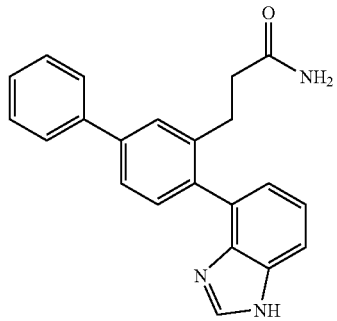 [SMILES: NC(=O)CCc1cc(-c2ccccc2)ccc1-c1cccc2[nH]cnc12]

Light brown powder (54 mg, 32%). 1H NMR (400 MHz, DMSO-d6) 12.32-12.57 (m, 1H), 8.16 (d, J=13.3 Hz, 1H), 7.03-7.79 (m, 12H), 6.54-6.75 (m, 1H), 2.67-2.81 (m, 2H), 2.20-2.33 (m, 2H), Spectrum was split into two species due to hydrogen exchange on the benzimidazole moiety; LCMS [M+H]+=342.2; HPLC (water/ACN+0.1% TFA gradient) 96.9% at 220 nm.

3-[4-(1H-Indazol-4-yl)biphenyl-3-yl]propanamide (T37)

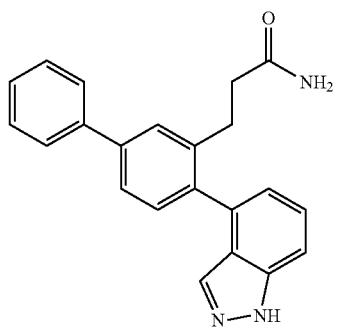 [SMILES: NC(=O)CCc1cc(-c2ccccc2)ccc1-c1cccc2[nH]ncc12]

Pale brown powder (69 mg, 42%). 1H NMR (400 MHz, DMSO-d6) 13.20 (s, 1H), 7.68-7.79 (m, 4H), 7.54-7.63 (m, 2H), 7.50 (t, J=7.6 Hz, 2H), 7.32-7.47 (m, 3H), 7.17 (br. s., 1H), 7.03 (d, J=6.8 Hz, 1H), 6.67 (br. s., 1H), 2.77 (t, J=7.8 Hz, 2H), 2.21-2.29 (m, 2H); LCMS [M+H]+=342.2; HPLC (water/ACN+0.1% TFA gradient) 99.7% at 220 nm.

3-[4-(1H-Benzotriazol-4-yl)biphenyl-3-yl]propanamide (T39)

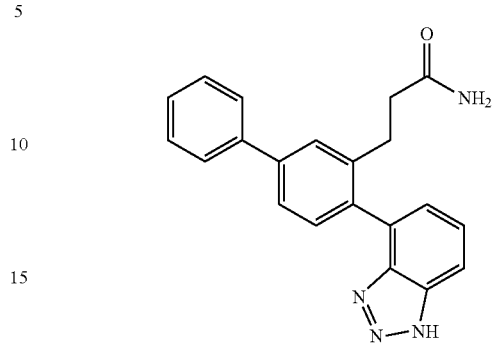

Pale yellow powder (10 mg, 6%). 1H NMR (400 MHz, DMSO-d6) 15.79 (br. s., 1H), 7.81-8.05 (m, 1H), 7.68-7.79 (m, 3H), 7.62 (d, J=7.8 Hz, 1H), 7.52 (t, J=7.7 Hz, 3H), 7.29-7.45 (m, 3H), 7.21 (br. s., 1H), 6.71 (br. s., 1H), 2.68-2.80 (m, 2H), 2.27 (t, J=7.8 Hz, 2H); LCMS [M+H]+=343.2; HPLC (water/ACN+0.1% TFA gradient) 98.2% at 220 nm.

3-(2,4-Difluoro-3-hydroxy-1,1':4',1"-terphenyl-2'-yl)propanamide (T58)

After the first ethyl acetate/water extraction, the aqueous layer was adjusted to pH 6 by the addition of 1M hydrochloric acid and workup continued per the general procedure. Obtained as a pale brown powder (106 mg, 62%). 1H NMR (400 MHz, DMSO-d6) 10.24 (br. s., 1H), 7.70 (d, J=7.4 Hz, 2H), 7.64 (d, J=1.4 Hz, 1H), 7.55 (dd, J=7.9, 1.7 Hz, 1H), 7.49 (t, J=7.6 Hz, 2H), 7.35-7.43 (m, 1H), 7.17-7.27 (m, 2H), 7.11 (t, J=9.2 Hz, 1H), 6.65-6.81 (m, 2H), 2.71 (t, J=7.7 Hz, 2H), 2.28 (t, J=7.9 Hz, 2H); LCMS [M+H]+=354.3; HPLC (water/ACN+0.1% TFA gradient) 99.5% at 220 nm.

Example 15

Synthesis of 5-Iodo-2-methylbenzene-1,3-diol for use in the production of T67

A mixture of 4-chloro-3,5-dimethoxyaniline (3.0 g, 16.0 mmol), palladium(II)acetate (180 mg, 0.80 mmol), 2-dicyclohexylphosphino-2,4,6-triisopropylbiphenyl (XPhos) (381 mg, 0.80 mmol), potassium carbonate (6.73 g, 48.7 mmol) and methylboronic acid (1.15 g, 19.2 mmol) in water (100 mL) and dioxane (100 mL) was heated to 100° C. (oil bath temperature) under nitrogen for 18 h. The reaction was not complete and heated to reflux for an additional 3 h, cooled to room temperature, diluted with water (200 mL) and extracted with ethyl acetate (3×150 mL), dried over magnesium sulfate, concentrated and purified by flash chromatography (ethyl acetate/hexanes) to give 3,5-dimethoxy-4-methylaniline (720 mg, 27%). 1H NMR (400 MHz, CDCl3) 5.93 (s, 2H), 3.77 (s, 6H), 3.58 (bs, 2H), 1.98 (s, 3H). Sodium nitrite (340 mg, 4.93 mmol) was added to a mixture of 3,5-dimethoxy-4-methylaniline (720 mg, 4.31 mmol) in sulfuric acid (1.1 mL) and water (13 mL) at 0° C. and stirred for 30 min. The ensuing mixture was added to a preheated mixture of sodium iodide (2.58 g, 17.2 mmol) and iodine (555 mg, 2.19 mmol) in sulfuric acid (1.1 mL) and water (13 mL) at 80° C., and the mixture heated to reflux for 30 min. The reaction mixture was cooled to room temperature and diluted with a solution of sodium sulfite (20% w/w, 100 mL) and water (100 mL), and extracted with ethyl acetate (3×100 mL). The organics were combined, dried over magnesium sulfate, concentrated and purified by flash chromatography (ethyl acetate/hexanes) to give 5-iodo-1,3-dimethoxy-2-methylbenzene as a white powder (388 mg, 32%). 1H NMR (400 MHz, CDCl3) 6.84 (s, 2H), 3.79 (s, 6H), 2.02 (s, 3H). 5-Iodo-1,3-dimethoxy-2-methylbenzene (388 mg, 1.39 mmol) in dichloromethane (8 mL) was cooled to 0° C. before adding neat boron tribromide (0.8 mL, 8 mmol) slowly over 1 min under nitrogen. The reaction mixture was allowed to warm to room temperature slowly over 3 h and stirred for 18 h. The reaction mixture was slowly and cautiously poured onto ice water (100 mL) and extracted with ethyl acetate (3×60 mL) and the combined organics washed with brine (1×50 mL), dried over magnesium sulfate, concentrated and purified by flash chromatography (ethyl acetate/hexanes) to give 5-iodo-2-methylbenzene-1,3-diol as a white powder (260 mg, 74%). 1H NMR (400 MHz, d6-DMSO) 9.44 (s, 2H), 6.63 (s, 2H), 1.87 (s, 3H).

Example 16

Synthesis of 5-Bromo-2-fluorobenzene-1,3-diol for use in the production of T68

A mixture of Oxone (1.44 g) in water (2 mL) was added to a solution of 5-bromo-2-fluoro-1,3-phenylenediboronic acid, pinacol ester (500 mg, 1.17 mmol) in acetone (1.5 mL) over 1 min and stirred at room temperature for 15 min. Additional Oxone (0.512 g) and acetone (1 mL) was added and stirred for a further 20 min. Sodium bisulfite solution (10% w/w, 10 mL) was added followed by water (10 mL) and extracted with dichloromethane (3×20 mL), dried over magnesium sulphate and purified by flash chromatography (ethyl acetate/hexanes) to give 5-bromo-2-fluorobenzene-1,3-diol as a white powder (159 mg, 66%). 1H NMR (400 MHz, CDCl3) 6.73 (d, J=6.8 Hz, 2H), 5.29 (bs, 2H).

Example 17

Synthesis of 2-Chloro-5-iodobenzene-1,3-diol for use in the production of T69

2-Chloro-5-iodobenzene-1,3-diol was synthesised in 3 steps from 3,5-dimethoxyaniline according to WO 2011/027106 A1, with a modification to the first step to prepare 4-chloro-3,5-dimethoxyaniline in which the reagent N chlorosuccinimide was added portion wise as a suspension in acetic acid (50 mL) to a solution of 3,5-dimethoxyaniline (10.01 g, 65.35 mmol) in acetic acid (50 mL) at 0° C. and warmed to room temperature after 30 min.

Example 18

Synthesis of T67, T68 and T69

T67, T68 and T69 were prepared from 3-[4-(4,4,5,5-Tetramethyl-1,3,2-dioxoborolan-2-yl)biphenyl-3-yl]propanamide (8—produced in Example 13). A mixture of 8 (1 equiv.), a substituted benzene-1,3-diol (produced in examples 15-17) (1.1 equiv.), Pd(dppf)Cl2.CH2Cl2 (0.1 equiv.) and sodium carbonate (2M, 5 mL/mmol) in N,N-dimethylformamide (10 mL/mmol) was bubbled through with nitrogen for 5 min before being heated to 80° C. under nitrogen for 18 h. The reaction mixture was cooled to room temperature and partitioned between 1M hydrochloric acid and ethyl acetate. The combined organics were washed with brine, dried over magnesium sulfate, concentrated and purified by flash chromatography (ethyl acetate/hexanes).

The following compounds were prepared by this procedure:

3-(3,5-Dihydroxy-4-methyl-1,1':4',1''-terphenyl-2'-yl)propanamide (T67)

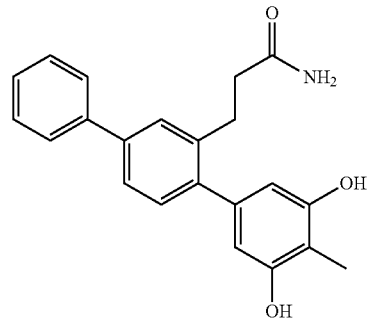 [SMILES: Cc1c(O)cc(-c2ccc(-c3ccccc3)cc2CCC(N)=O)cc1O]

White powder (121 mg, 59%). 1H NMR (400 MHz, DMSO-d6) 9.17 (s, 2H), 7.68 (d, J=7.43 Hz, 2H), 7.58 (br. s, 1H), 7.48 (t, J=7.80 Hz, 3H), 7.37 (s, 1H), 7.23 (br. s., 1H), 7.17 (d, J=7.83 Hz, 1H), 6.76 (br. s, 1H), 6.25 (s, 2H), 3.33 (s, 3H), 2.85 (t, 1=7.83 Hz, 2H), 2.30 (t, J=7.83 Hz, 2H). LCMS [M+H]+=348. HPLC (water/ACN+0.1% TFA gradient) 100% at 220 nm.

3-(4-Fluor-3,5-dihydroxy-1,1':4',1''-terphenyl-2'-yl)propanamide (T68)

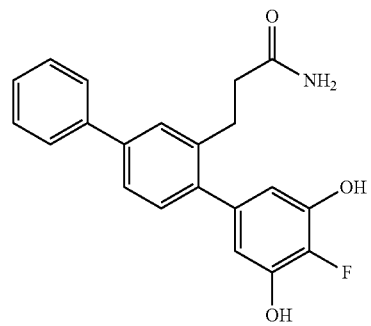 [SMILES: NC(=O)CCc1cc(-c2ccccc2)ccc1-c1cc(O)c(F)c(O)c1]

Pale yellow solid (82 mg, 41%). 1HNMR (400 MHz, DMSO-d6): 9.70 (br. s, 2H), 7.68 (d, J=7.43 Hz, 2H), 7.58 (s, 1H), 7.43-7.53 (m, 3H), 7.32-7.42 (m, 1H), 7.25 (br. s, 1H), 7.18 (d. J=7.83 Hz, 1H), 6.75 (br. s, 1H), 6.33 (d, J=7.43 Hz, 2H), 2.83 (t, J=7.80 Hz, 2H), 2.30 (t, J=8.20 Hz, 2H). LCMS [M+H]+=352. HPLC (water/ACN+0.1% TFA gradient) 96.1% at 220 nm.

3-(4-Chloro-3,5-dihydroxy-1,1':4',1''-terphenyl-2'-yl) propanamide (T69)

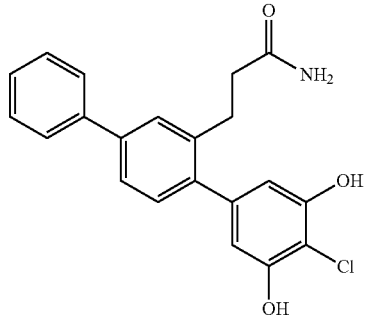 [SMILES: NC(=O)CCc1cc(-c2ccccc2)ccc1-c1cc(O)c(Cl)c(O)c1]

White powder (26 mg, 12%). 1H NMR (400 MHz, DMSO-d6) 9.93-10.12 (m, 2H), 7.69 (d, J=7.43 Hz, 2H), 7.59 (s, 1H), 7.43-7.54 (m, 3H), 7.34-7.42 (m, 1H), 7.25 (br. s., 1H), 7.19 (d, J=7.83 Hz, 1H), 6.76 (br. s., 1H), 6.38 (s, 2H), 2.84 (t, J=7.40 Hz, 2H), 2.30 (t, J=8.20 Hz, 2H). LCMS [M+H]+=368. HPLC (water/ACN+0.1% TFA gradient) 100% at 254 nm.

Example 19

Synthesis of T25

Figure 8:
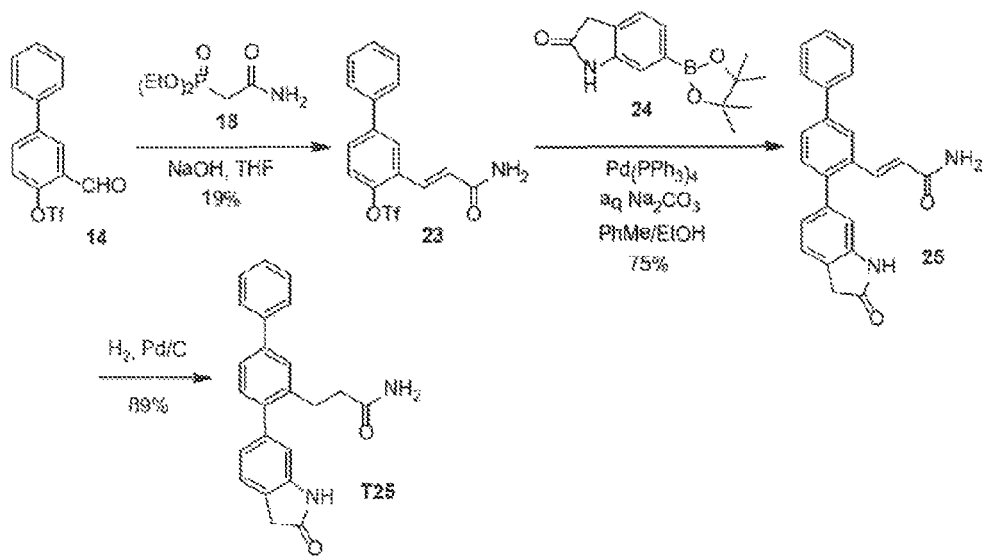
FIG. 8: Synthesis of T25.

The synthetic route used to prepare T25 is shown in FIG. 8. Briefly, 3-formylbiphenyl-4-yl trifluoromethanesulfonate (14) was subjected to a Horner-Wadsworth-Emmons reaction with diethyl(carbamoylmethyl)phosphonate (18) to afford biphenyl acrylamide (23), which cross-coupled with indolone pinacol boronic ester (24) to produce indolone acrylamide (25). Subsequent hydrogenation of compound 25 yielded T25.

Figure 9:
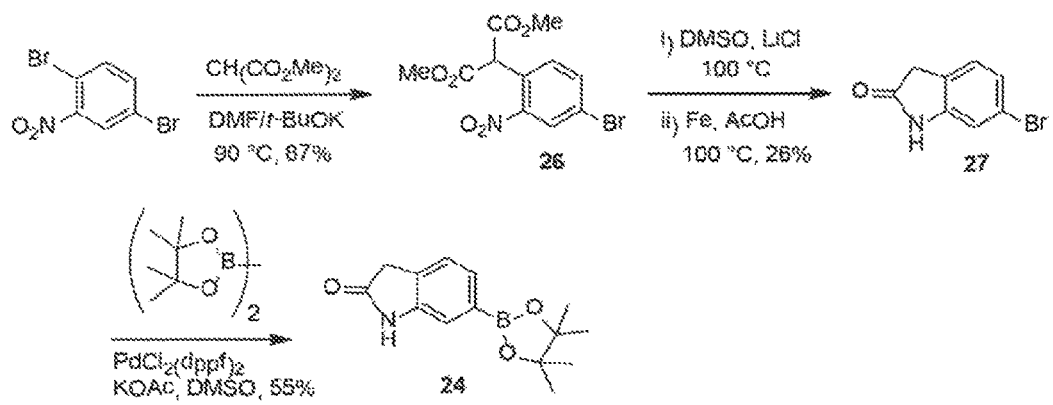
FIG. 9: Synthesis of indolone pinacol boronic ester.

To synthesise T25, the requisite indolone pinacol boronic ester (24) was needed. Thus, 1,4-dibromo-2-nitrobenzene was alkylated with dimethyl malonate to give aryl malonate (26), which was decarboxylated and cyclised to form bromoindolone (27); this was in turn reacted with bis(pinacolato)diborane to form indolone pinacol boronic ester (24) (FIG. 9).

Production of Dimethyl 2-(4-bromo-2-nitrophenyl)malonate (26)

To a mixture of potassium tert-butoxide (21.6 g, 193.00 mmol) in DMF (75 mL) was added dimethyl malonate (22.40 mL, 196.00 mmol). The reaction was exothermic and a solid precipitated out. The reaction mixture was heated to 90° C. for 10 minutes, then cooled to ambient temperature. 2,5-Dibromonitrobenzene (25.50 g, 91 mmol) was added as a solid. The reaction mixture turned purple and was stirred at 90° C. for 2 hours. After cooling to ambient temperature, it was poured onto ice cold 5% hydrochloric acid solution and transferred to a separating funnel. The crude material was extracted out with ethyl acetate (2×). The combined ethyl acetate extracts were washed with water and brine to give a bright yellow oil. The crude oil was pre-absorbed onto Celite, then chromatographed (DCVC) eluting with a gradient of ethyl acetate in heptane (0-10%/ethyl acetate). Like fractions were combined and were recrystallised from DCM and heptane to give dimethyl 2-(4-bromo-2-nitrophenyl) malonate (26) as pale yellow needles (26.78 g, 87%); mp 85.8-87.1° C. $^1$H NMR (400 MHz, CDCl$_3$) δ 8.18 (d, 1H, J 2.1 Hz), 7.75 (dd, 1H, J 2.1, 8.4 Hz), 7.40 (d, 1H, J 8.4 Hz), 5.26 (s, 1H), 3.78 (s, 6H).

Production of 6-Bromoindolin-2-one (27)

Lithium chloride (6.36 g, 156.0 mmol) was added to a solution of dimethyl 2-(4-bromo-2-nitrophenyl)malonate (26) (26.0 g, 78.30 mmol) in dimethylsulfoxide (100 mL) and was heated at 100° C. for 20 hours. Once cooled to ambient temperature the reaction mixture was partitioned between ethyl acetate and brine. The layers were separated, then washed with brine again and concentrated. The dark tan oil was dissolved in acetic acid (100 mL) and iron powder (17.50 g, 313.0 mmol) was added (exotherm). The reaction was then heated at 110° C. for 1 hour. The acetic acid was removed by rotary evaporation and the residue dissolved in ethyl acetate and the iron powder was removed by filtering through Celite. The filtrate was washed with 1M hydrochloric acid and water, then filtered through phase separation paper (IPS). The crude material was pre-absorbed onto Celite, then chromatographed (DCVC) eluting with chloroform. Fractions containing the desired material were combined, pre-absorbed onto Celite and chromatographed (DCVC) again eluting with a gradient of ethyl acetate in heptane (20-80% ethyl acetate). Clean fractions were combined and recrystallised from DCM and methanol to give 6-bromoindolin-2-one (27) as yellow needles (4.32 g, 26%); mp 208-214° C. $^1$H NMR (400 MHz, CDCl$_3$) δ 10.47 (br s, 1H), 7.14 (d, 1H, J 7.9 Hz), 7.09 (dd, 1H, J 1.8, 7.9 Hz), 6.94 (d, 1H, J 1.8 Hz), 3.44 (s, 2H).

Production of 6-(44, 4,5,5-tetramethyl-1,3,2-dioxaborolan-2-yl)indolin-2-one (24)

6-Bromoindolin-2-one (27) (2.00 g, 9.40 mmol), bispinacolatodiboron (6.00 g, 23.60 mmol), potassium acetate (2.76 g, 28.2 mmol) and dichloro[1,1'-bis(diphenylphosphino)ferrocene]palladium (11) dichloromethane adduct (0.40 g, 0.55 mmol) in DMSO (30 mL) were stirred at 90° C. for 18 hours. The reaction mixture was cooled to ambient temperature, then partitioned between water and ethyl acetate. The layers were separated and the aqueous layer extracted again with ethyl acetate (2×). The combined organic layers were washed with water and brine and concentrated to give a purple solid. The crude material was pre-absorbed onto Celite and chromatographed (DCVC) eluting with a gradient of ethyl acetate in heptane (0-50% ethyl acetate). Like fractions were combined and recrystallised from DCM and PE to give 6-(4,4,5,5-tetramethyl-1,3,2-dioxaborolan-2yl) indolin-2-one (24) as a colourless solid in 2 crops (1.33 g, 55%); mp 178.5-181.4° C. $^1$H NMR (200 MHz, CDCl$_3$) δ 8.61 (br s, 1H), 7.46 (d, 1H, J 7.4 Hz), 7.30 (s, 1H), 7.21 (d, 1H, J 7.4 Hz), 3.53 (s, 2H), 1.32 (s, 12H).

Production of (E)-3-(3-Amino-3-oxoprop-1-en-1-yl)-[1,1'-biphenyl]-4-yl trifluoromethanesulfonate (23)

3-Formylbiphenyl-4-yltrifluoromethanesulfonate (14) (3.80 g, 11.50 mmol) and diethyl (2-amino-2-oxoethyl)

phosphonate (18) (2.25 g, 11.50 mmol) were dissolved in dry THF (100 mL), and added slowly to a vigorously stirred suspension of powdered sodium hydroxide (0.92 g, 23.00 mmol). Following stirring for 1 h at rt, the reaction mixture was partitioned between brine and ethyl acetate. A yellow by-product was removed by flitration and the layers separated. The organic layer was concentrated and then purified by chromatography (DCVC) eluting with a gradient of ethyl acetate in heptane (0-20% ethyl acetate), and then recrystallised from DCM and PE to give (E)-3-(3-amino-3-oxoprop-1-en-1-yl)-[1,1'-biphenyl]-4-yl trifluoromethanesulfonate (23) as a beige solid (0.82 g, 19%); mp 130.6-132.3° C. $^1$H NMR (400 MHz, DMSO-$d_6$) δ 8.09-8.04 (m, 1H), 7.88-7.82 (m, 1H), 7.79-7.73 (m, 2H), 7.65-7.41 (m, 6H), 7.33 (br s, 1H), 6.93 (d, 1H, $^3J_{trans}$ 16 Hz). $^{13}$C NMR (100 MHz, DMSO-$d_6$) δ 165.6, 146.4, 141.1, 138.0, 130.0, 129.5, 129.1, 128.6, 128.4, 127.7, 127.1, 126.4, 122.8, 118.1 (q, J 321 Hz). EIMS: m/z Found: $M^{+\cdot}$ 371.0420, $C_{16}H_{12}F_3NO_4{}^{32}S$ requires 371.0434. EIMS: m/z 371 ($M^{+\cdot}$, 62%), 195 (100), 167 (100).

Production of (E)-3-(4-(2-Oxindolin-6-yl)-[1,1'-biphenyl]-3-yl)acrylamide (25)

Prepared according to the method used to generate P5; from (E)-3-(3-amino-3-oxoprop-1-en-1-yl)-[1,1'-biphenyl]-4-yl trifluoromethanesulfonate (23) (0.50 g, 1.35 mmol), 6-(4,4,5,5-tetramethyl-1,3,2-dioxaborolan-2yl)indolin-2-one (24) (0.43 g, 1.68 mmol), tetrakis(triphenylphosphine) palladium(0) (0.100 g, 0.09 mmol) and aqueous sodium carbonate (1M) (3.0 mL, 3.00 mmol) in toluene (10 mL) and ethanol (2 mL). The crude material was collected by filtration from the aqueous work-up, then purified by trituration in DCM and methanol to give (E)-3-(4-(2-oxindolin-6-yl)-[1,1'-biphenyl]-3-yl)acrylamide (25) as pale lemon needles (0.36 g, 75%); mp 263-267° C. (December). $^1$H NMR (400 MHz, DMSO-$d_6$) δ 10.47 (s, 1H), 7.95 (s, 1H), 7.80-7.70 (m, 3H), 7.57-7.37 (m, 5H), 7.46 (br s, 1H), 7.32 (d, 1H, J 7.6 Hz), 7.12 (br s, 1H), 6.89 (d, 1H, J 7.6 Hz), 6.80-6.72 (m, 2H), 3.55 (s, 2H). $^{13}$C NMR (100 MHz, DMSO-$d_6$) δ 177.4, 166.5, 143.9, 141.1, 139.6, 139.4, 138.8, 137.4, 133.1, 130.9, 129.0, 127.8, 127.6, 126.8, 125.3, 124.4, 124.3, 123.7, 122.6, 110.1, 35.6. EIMS: m/z Found: $M^{+\cdot}$ 354.1356, $C_{23}H_{18}N_2O_2$ requires 354.1363. EIMS: m/z 354 ($M^{+\cdot}$, 13%), 310 (100), 309 (43).

Production of 3-(4-(2-Oxoindolin-6-yl)-[1,1'-biphenyl]-3-yl)propanamide (T25)

Prepared according to the method used to generate T18; from (E)-3-(4-(2-oxindolin-6-yl)-[1,1'-biphenyl]-3-yl)acrylamide (25) (0.11 g, 0.30 mmol) and 10% palladium on carbon (50% wt water) in methanol (30 mL). The filtrate was concentrated to give 3-(4-(2-oxoindolin-6-yl)-[1,1'-biphenyl]-3-yl)propanamide (T25) as a pale yellow solid (0.96 g, 89%); mp 219-222° C. $^1$H NMR (400 MHz, DMSO-$d_6$) δ 10.44 (s, 1H), 7.74-7.65 (m, 2H), 7.65-7.58 (m, 1H), 7.56-7.43 (m, 3H), 7.42-7.34 (m, 1H), 7.31-7.19 (m, 3H), 6.94-6.87 (m, 1H), 6.80-6.71 (m, 2H), 3.53 (s, 2H), 2.84 (t, 2H, J 7.9 Hz), 2.31 (t, 2H, J 7.9 Hz). $^{13}$C NMR (50 MHz, DMSO-$d_6$) δ 176.5, 173.4, 143.8, 140.6, 140.2, 140.0, 139.2, 139.1, 130.3, 128.9, 127.4, 127.3, 126.7, 124.6, 124.2 (two signals coincident), 121.9, 109.7, 36.2, 35.6, 28.2. EIMS: m/z Found: $M^{+\cdot}$ 356.1531, $C_{23}H_{20}N_2O_2N$ requires 356.1531. EIMS: m/z 356 ($M^{+\cdot}$, 100%), 297 (70). HPLC purity (35% ACN/0.1% TFA, 256 nm): 97.57%.

Example 20

Synthesis of T31

Figure 10:
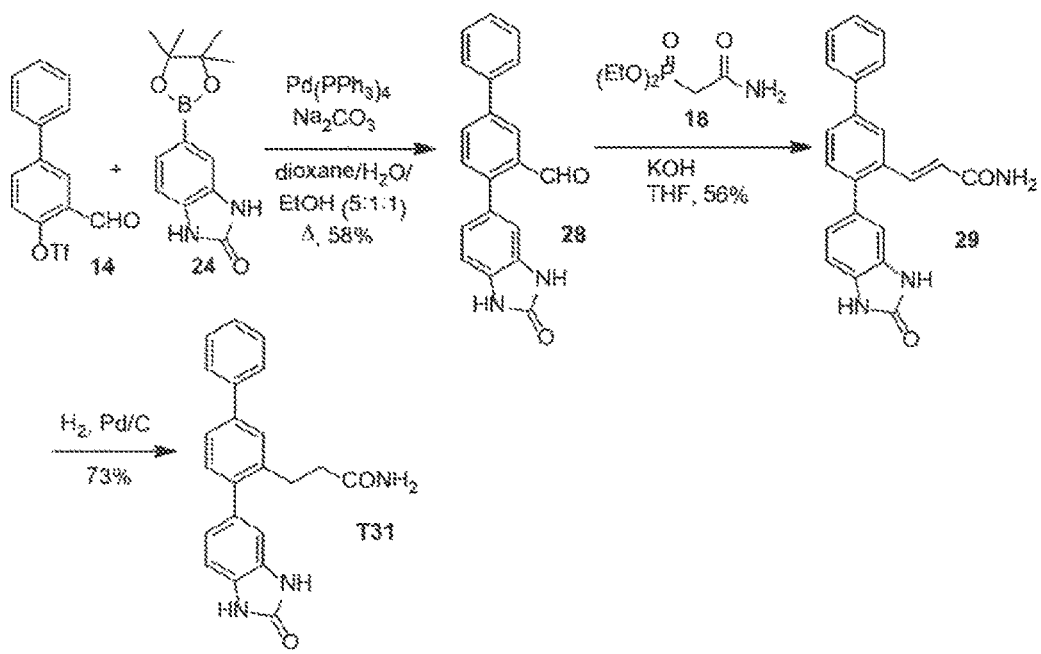
FIG. 10: Synthesis of T31.

The synthetic route used to prepare T31 is shown in FIG. 10. Briefly, 3-formylbiphenyl-4-yl trifluoromethanesulfonate (14) was cross-coupled with benzimidazolone pinacol boronic ester (24) to produce benzimidazolone (28), which then underwent a Horner-Wadsworth-Emmons reaction with diethyl(carbamoylmethyl)phosphonate (18) to afford benzimidazolone acrylamide (29). Subsequent hydrogenation of compound 29 yielded T31.

Production of 4-(2-Oxo-2,3-dihydro-1H-benzo[d]imidazol-5-yl)-[1,1'-biphenyl]-3-carbaldehyde (28)

To a suspension of 2-oxo-2,3-dihydro-1H-benzoimidazole-5-boronic acid pinacol ester (24) (574 mg, 2.2 mmol), 3-formylbiphenyl-4-yl trifluoromethanesulfonate (14) (663 mg, 2.0 mmol) and sodium carbonate (426 mg, 4.0 mmol) in degassed dioxane/ethanol/H$_2$O (5:1:1, 20 mL) was added tetrakis(triphenylphosphine)palladium(0) (116 mg, 0.1 mmol). The reaction was heated at 110° C. for 2 h in a sealed tube. Analysis by TLC (1:2 DCM; PE) indicated the triflate had been consumed. The reaction was concentrated to dryness, then taken up in equal volumes of DCM and water and stirred vigorously for 20 minutes, ensuring all lumps were broken up and a fine precipitate was achieved. The solid was collected by filtration through hardened ashless paper (540) on a Buchner funnel, and washed thoroughly with DCM and water. The solid was dried in vacuo at 40° C. to afford 4-(2-oxo-2,3-dihydro-1H-benzo[d]imidazol-5-yl)-[1,1'-biphenyl]-3-carbaldehyde (28) (365 mg, 58%) as a pale yellow solid. $^1$H NMR (200 MHz, DMSO-$d_6$) δ 10.82 (brs, 2H), 9.95 (s, 1H), 8.15-7.96 (m, 2H), 7.76 (m, 2H), 7.68-7.36 (m, 4H), 7.12-6.95 (m, 3H). $^{13}$C NMR (50 MHz, DMSO-$d_6$) δ 192.1, 155.4, 144.6, 139.1, 138.7, 133.7, 131.8, 131.7, 130.1, 130.0, 129.2, 128.0, 126.7, 125.1, 122.9, 109.7, 108.4 (one signal not observed). EIMS: m/z Found: $M^{+\cdot}$ 314.1050, $C_{20}H_{14}O_2N_2$ requires 314.1055. EIMS: m/z 314 ($M^{+\cdot}$, 100%).

Production of (E/Z)-3-(4-(2-Oxo-2,3-dihydro-1H-benzo[d]imidazol-5-yl)-[1,1'-biphenyl]-3-yl)acrylamide (29)

4-(2-Oxo-2,3-dihydro-1H-benzo[d]imidazol-5-yl)-[1,1'-biphenyl]-3-carbaldehyde (28) (350 mg, 1.1 mmol) and diethyl (carbamoylmethyl)phosphonate (18) (217 mg, 1.1 mmol) were dissolved in dry THF (15 mL), and added slowly to a vigorously stirred suspension of powdered KOH (125 mg, 2.2 mmol) in THF (10 mL). The reaction was stirred at it for 1 h under an argon atmosphere. Analysis by TLC (1:99 methanol:DCM) indicated the carbaldehyde had been consumed. The THF was removed under reduced pressure, and the residue taken up in equal volumes of DCM and water and stirred vigorously for 30 minutes; ensuring all lumps were broken up and a fine precipitate achieved. The solid was collected by filtration through hardened ashless paper (540) on a Buchner funnel, and washed thoroughly with DCM and water. The solid was dried in vacuo at 40° C. to afford (E/Z)-3-(4-(2-oxo-2,3-dihydro-1H-benzo[d]imidazol-5-yl)-[1,1'-biphenyl]-3-yl)acrylamide (29) (247 mg, 56%) as a yellow/brown solid. $^1$H NMR (200 MHz, DMSO-$d_6$) δ 10.74 (brs, 1H), 10.70 (brs, 1H), 7.93 (d, 1H, J 1.8), 7.80-7.67 (m, 3H), 7.58-7.34 (m, 6H), 7.14-6.98 (m, 2H), 6.94-6.83 (m, 2H), 6.74 (d, 1H, J 15.8 Hz). $^{13}$C NMR (100

MHz, DMSO-$d_6$) δ 166.6, 155.4, 141.5, 139.5, 139.1, 137.8, 133.1, 131.7, 131.2, 129.8, 129.3, 129.0, 127.7, 127.5, 126.7, 124.4, 123.4, 122.4, 109.5, 108.3. EIMS: m/z Found: $M^{+\cdot}$ 355.1315, $C_{22}H_{17}O_2F_3$ requires 355.1315. EIMS: m/z 355 ($M^{+\cdot}$, 31%).

Production of 3-(4-(2-Oxo-2,3-dihydro-1H-benzo[d]imidazol-5-yl)-[1,1'-biphenyl]-3-yl)propanamide (T31)

(E/Z)-3-(4-(2-Oxo-2,3-dihydro-1H-benzo[d]imidazol-5-yl)-[1,1'-biphenyl]-3-yl)acrylamide (29) (240 mg, 0.7 mmol) and 10% palladium on carbon (50% wt in $H_2O$, 100 mg) in methanol (20 mL) were stirred at rt under a hydrogen atmosphere at 50 psi for 2 h. The reaction mixture was gravity filtered through GF paper washing thoroughly with methanol, then concentrated. Purified by preparative HPLC (55% methanol/$H_2O$, 70 mL/min, 280 nm, 300×40 mm Deltaprep $C_{18}$ column) to afford 3-(4-(2-oxo-2,3-dihydro-1H-benzo[d]imidazol-5-yl)-[1,1'-biphenyl]-3-yl)propanamide (T31) (177 mg, 73%) as a pink solid; mp 250-251° C. $^1$H NMR (400 MHz, DMSO-$d_6$) δ 10.67 (d, 2H, J 7.8 Hz), 7.69 (m, 2H), 7.60 (d, 1H, J 1.9 Hz), 7.53-7.45 (m, 3H), 7.37 (m, 1H), 7.28-7.21 (m, 2H), 6.99 (d, 1H, J 7.8 Hz), 6.90 (dd, 1H, J 1.6, 7.9 Hz), 6.89-6.86 (m, 1H), 6.74 (brs, 1H), 2.84 (m, 2H), 2.30 (m, 2H). $^{13}$C NMR (100 MHz, DMSO-$d_6$) δ 173.4, 155.4, 140.9, 140.0, 139.3, 138.8, 133.1, 130.6, 129.7, 128.9, 128.8, 127.3, 127.2, 126.6, 124.1, 121.3, 109.0, 108.1, 36.1, 28.3. EIMS: m/z Found: $M^{+\cdot}$ 357.1469, $C_{22}H_{16}N_3O_2$ requires 357.1472. EIMS: m/z 357 ($M^{+\cdot}$, 30%). HPLC purity (40% ACN/$H_2O$, 282 nm): 94.51%.

Example 21

In Vitro Screening

The xCELLigence SP system (Roche) was used to measure changes in cellular impedance (cell index) following the treatment of A10 embryonic vascular smooth muscle cells (ATCC, CRL-1476) with test compound. This in vitro assay was correlated with blood pressure data obtained in the animal model described below in Example 22, so that it can be used for faster screening of larger number of compounds. In this in vitro cell based experimental system a negative impedance profile correlates with blood pressure reduction in rats—a decrease in impedance is associated with vasodilatation and an increase in impedance is associated with vasoconstriction (Stallaert W, Dorn J F, van der Westhuizen E, Audet M & Bouvier M. Impedance responses reveal β-adrenergic signaling pluridensitometry and allow classification of ligands with distinct signalling profiles PLoS ONE 2012; 7(1):e29420, doi:10.1371/journal.pone.0029420).

Briefly, 50 μl of cell culture medium (DMEM low glucose supplemented with 10% fetal bovine serum at 37° C.) was added to each well of an E-Plate 96 (Roche), and the background impedance in each well was measured. 50 μl of A-10 cell suspension (10,000 cells/well) was then added to the appropriate wells of the E-Plate 96. Cell index was monitored for each well of the E-Plate 96 in RTCA SP Station within the cell culture incubator. After overnight incubation for 16-20 hours at 5% $CO_2$ and 95% humidity, 100 μl of test compound solution (test compounds were prepared in DMSO and diluted with cell culture medium to a final DMSO concentration of 0.25%) was added to the appropriate wells of the E-Plate 96 and cell index values were measured immediately following compound treatment every 20 seconds for 3 hours. Cell index value is baseline-corrected by subtracting the cell index of vehicle-treated cells and normalized by dividing by the cell index at the time point immediately before compound addition. Baseline normalized cell index as a function of time is plotted using Roche RTCA software.

Figure 11:
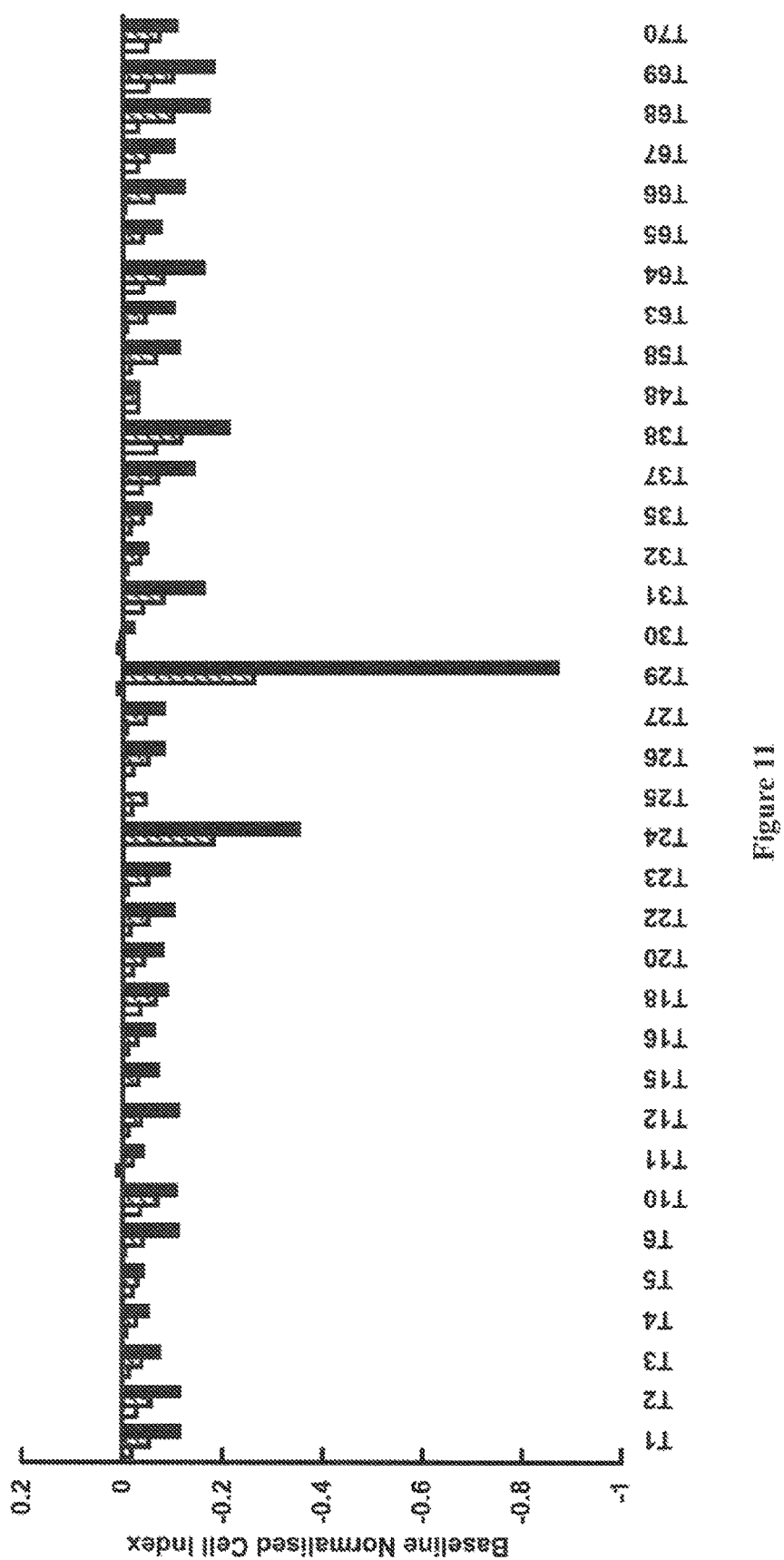
FIG. 11: Baseline normalised cell index for various compounds at three concentrations, 62.5 µM (open bars), 125 µM (hatched bars) and 250 µM (solid bars), on rat A10 vascular smooth muscle cells as determined using the xCELLigence RTCA instrument.

Compounds may achieve reductions in blood pressure by interaction with vascular smooth muscle cells causing these cells to relax resulting in vasodilatation and a reduction in blood pressure. These are termed direct vasodilators. A negative impedance response for A10 vascular smooth muscle cells indicates that a test compound is a direct vasodilator (FIG. 11).

The xCELLigence SP system (Roche) was also used to measure changes in cellular impedance (cell index) following the treatment of bovine aortic endothelial cells (European Collection of Cell Cultures) with test compound. The method employed is the same for the A10 embryonic vascular smooth muscle cells described above but with the cell culture medium supplemented with 15% fetal bovine serum instead of 10%.

Figure 12:
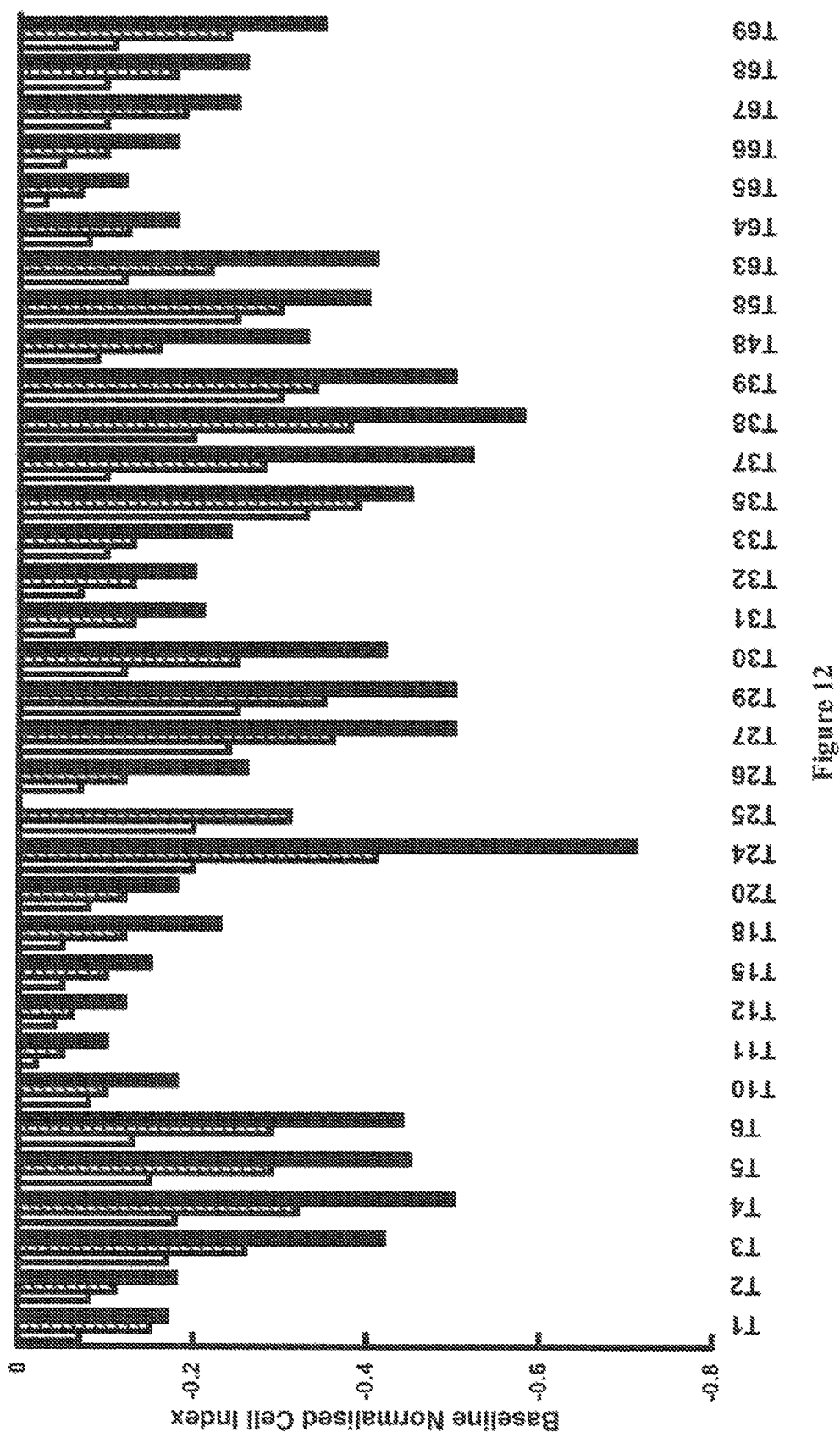
FIG. 12: Baseline normalised cell index for various compounds at three concentrations, 62.5 µM (open bars), 125 µM (hatched bars) and 250 µM (solid bars), on bovine aortic endothelial cells as determined using the xCELLigence RTCA instrument.

Compounds may interact with vascular endothelial cells causing the release of substances such as nitric oxide and endothelium-derived hyperpolarising factor, which in turn act on the vascular smooth muscle cells causing vasodilatation and lowering blood pressure. Such compounds are termed indirect vasodilators. A negative impedance response for bovine aortic endothelial cells indicates that a test compound is an indirect vasodilator (FIG. 12).

Example 22

In Vivo Screening

Oral Studies

Fourteen week old SHR (on a 2.2% salt diet; Glen Forrest Stockfeeders) were randomly assigned to zero time control, test compound treatment (100 or 500 pmol/kg/min) in the drinking solution or control drinking solution (5% ethanol in deionised distilled water (n=5 each group). The rats assigned to zero time control group were anaesthetised and had their heart and kidneys harvested while rats assigned to control and test compound treatment were weighed twice weekly and had their drinking solution intake monitored to allow adjustment of the test compound concentration in the drinking solution to maintain a constant dose over the 4-week study period. Blood pressure was measured twice weekly by tail cuff plethysmography (PowerLab, ADInstruments, Castle Hill, NSW, Australia).

After 4 weeks rats were anaesthetised, and their hearts and kidneys harvested for quantitation of fibrosis.

Fibrosis Quantitation

To quantitate tissue fibrosis tissue slices ≤3 mm thick were fixed in 10% buffered formalin for 24 hours, processed and embedded in paraffin. Three micron transverse sections were stained using Masson's trichrome stain. A minimum of 20 random fields at magnification ×20 from transverse sections (5 at each of 2 levels) were digitized and the degree of fibrosis determined as a percent of field area of each digitized image using Image-Pro Plus V.7 (Media Cybernetics, Bethesda, Md., USA) then averaged to determine the level of fibrosis for tissue for each rat.

Results

Figure 13:
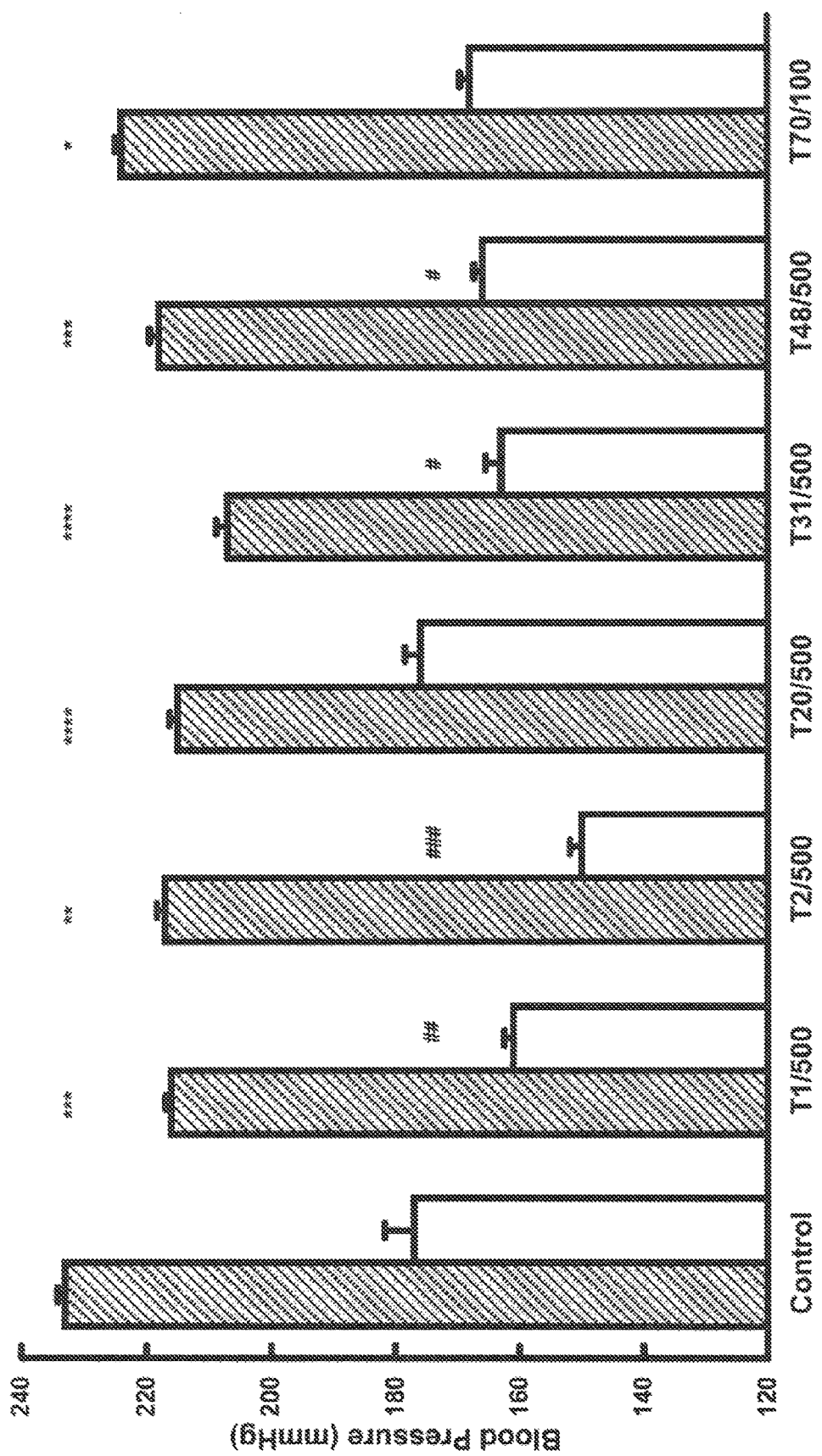
FIG. 13: Systolic (hatched bars) and diastolic (open bars) blood pressures in controls and treated spontaneous hypertensive rats (SHR) on a 2.2% salt diet after 4 weeks therapy. T1, T2, T20, T31 and T48 were administered at 500 pmol/kg/min in the drinking solution (5% ethanol) for 4 weeks, T70 was administered at 100 pmol/kg/min in the drinking solution. * $p<0.05$,  $p<0.01$, * $p<0.005$ and **** $p<0.0005$ treated systolic vs control systolic; #$p<0.05$, ##$p<0.025$ and ###$p<0.005$ diastolic treated vs diastolic control.

Mean systolic blood pressure results observed for animals on 2.2% salt diet after 4 weeks treatment with 100 or 500 pmol/kg/min T1, T2, T20, T31, T48 or T70 orally showed decreased blood pressure compared to controls (FIG. 13).

Mean diastolic blood pressure was also decreased compared to controls for T1, T2, T31 and T70.

Figure 14:
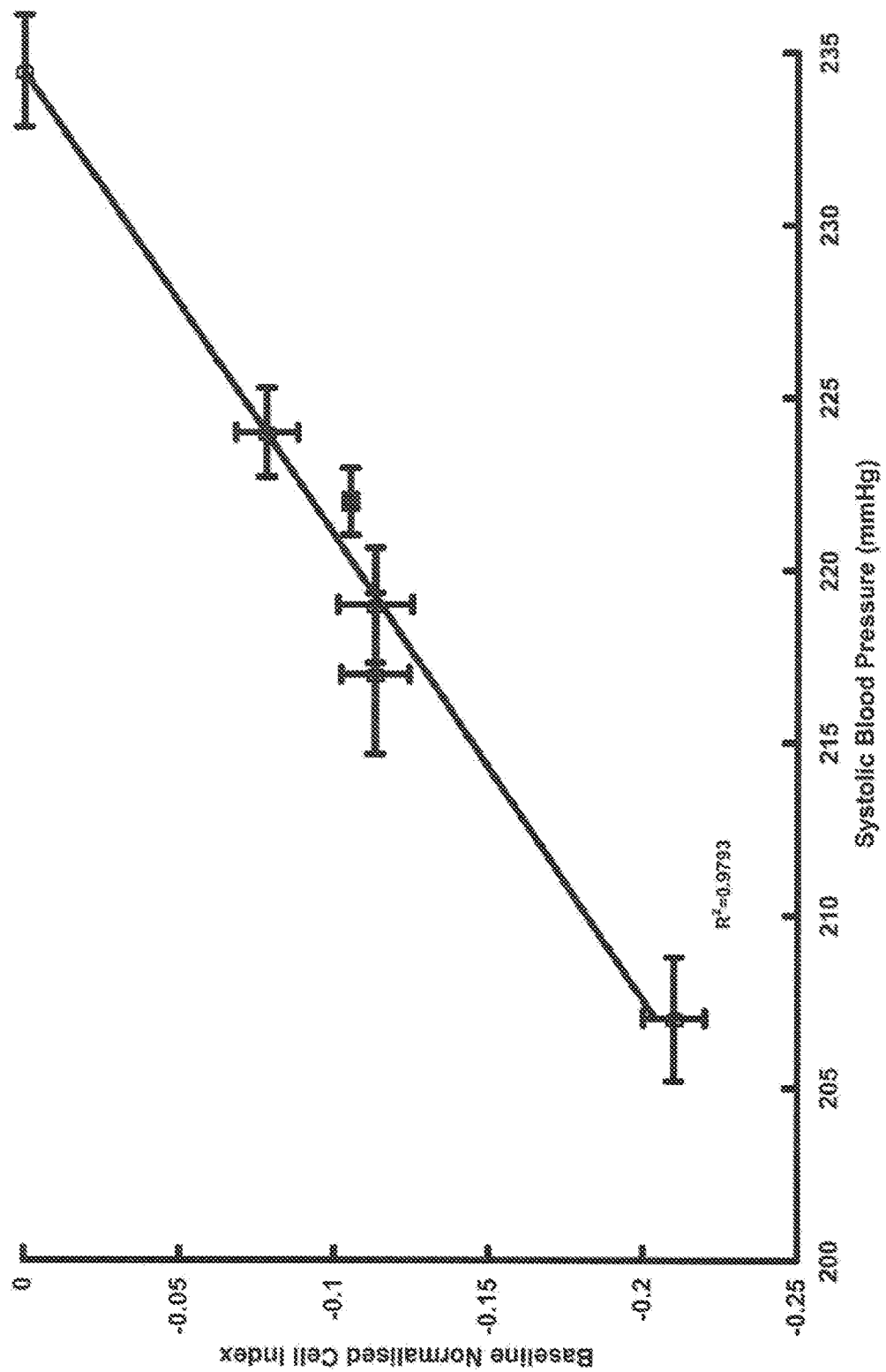
FIG. 14: Relationship between baseline normalised cell index for A10 vascular smooth muscle cells and systolic blood pressure for various compounds.
Figure 15:
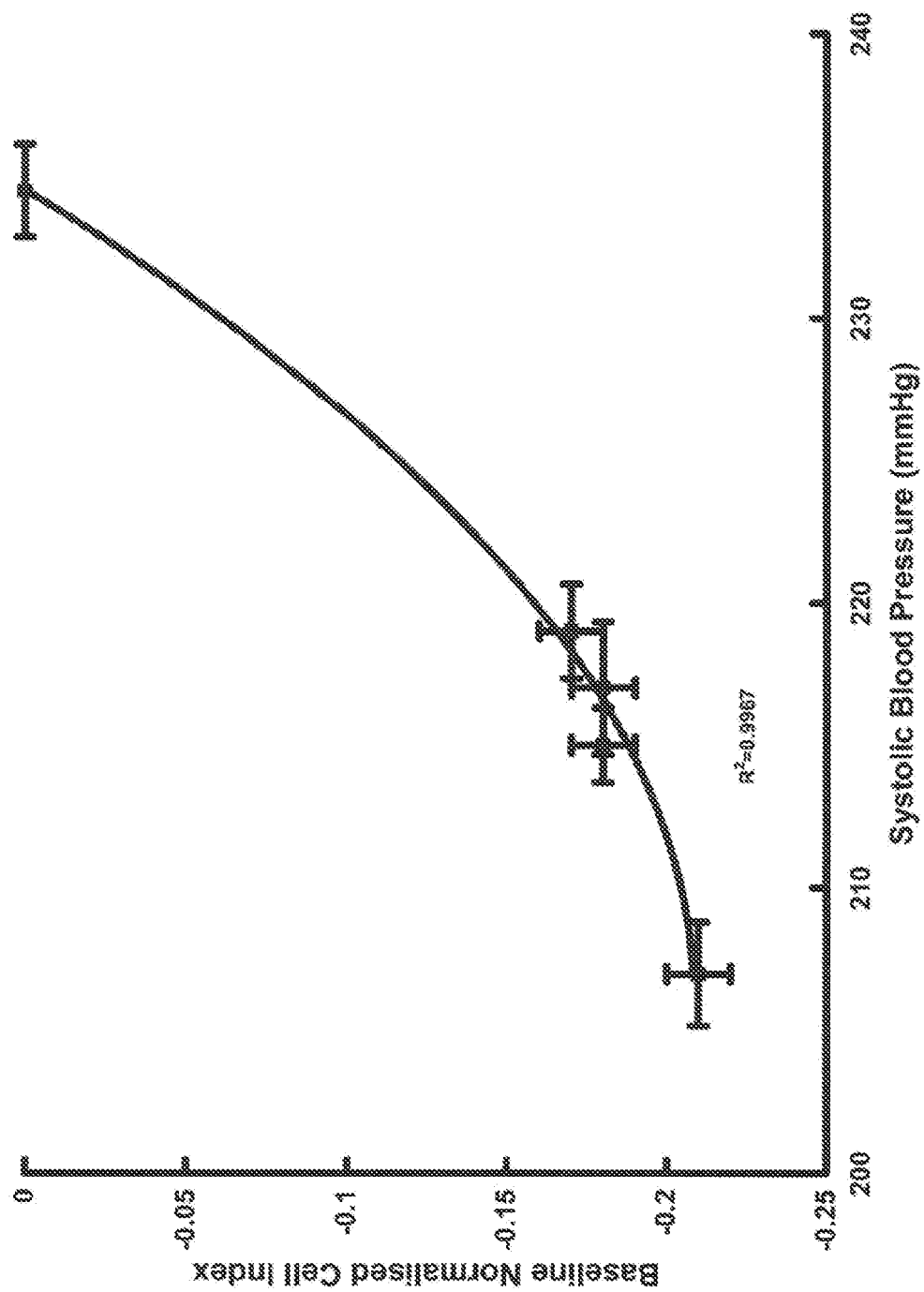
FIG. 15: Relationship between baseline normalised cell index for bovine aortic endothelial cells and systolic blood pressure for various compounds.

The mean systolic blood pressure results for T1, T2, T20, T31, T48 and T70 were compared to the baseline normalised cell indexes of the compounds on A10 vascular smooth muscle cells (FIG. 14) and the bovine aortic endothelial cells (FIG. 15) and showed a correlation between the in vivo and in vitro results.

Figure 16:
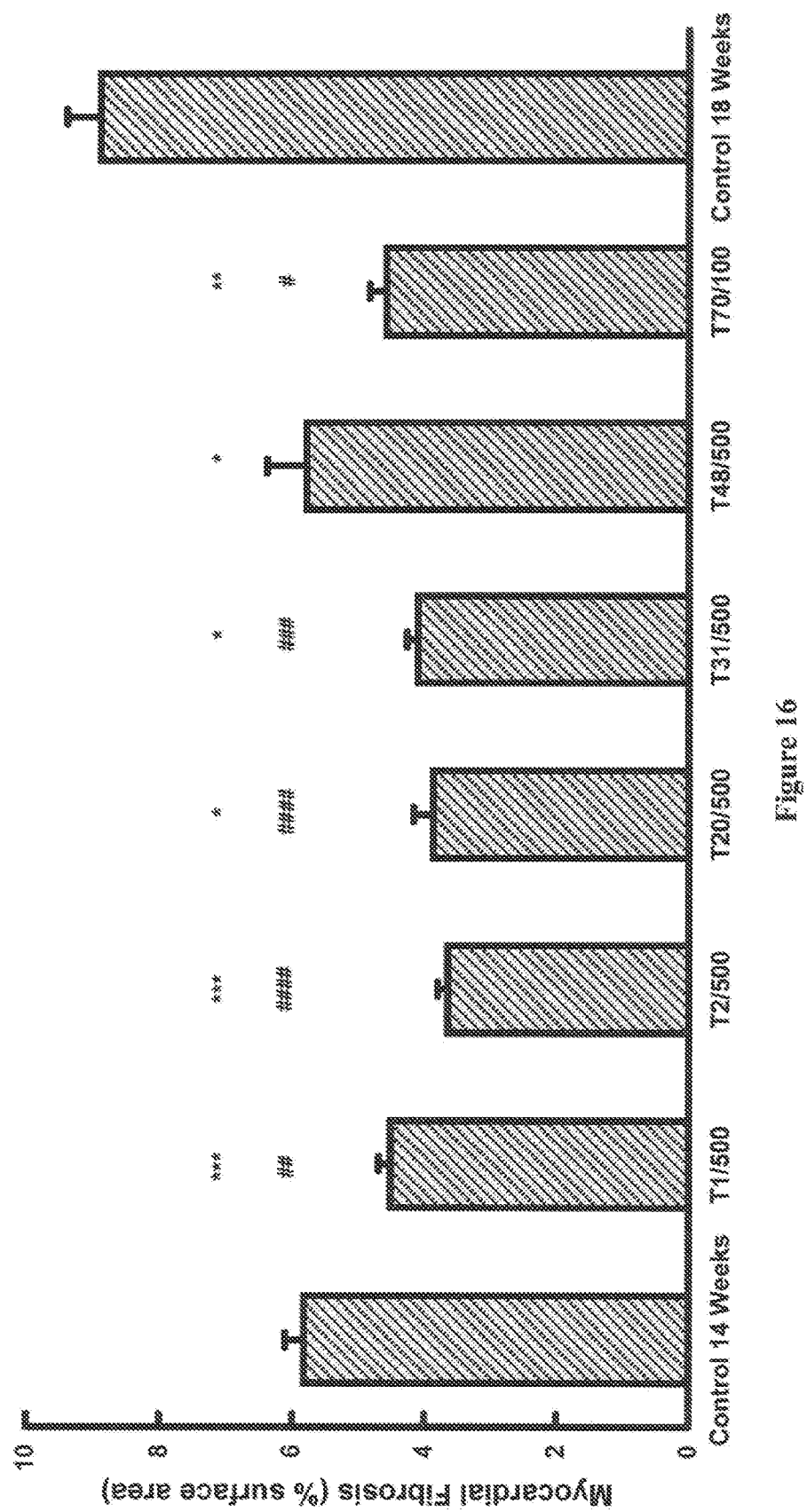
FIG. 16: Myocardial fibrosis quantitated by computerised histomorphometry on Masson's trichrome stained histological sections in SHR on a 2.2% salt diet at 14 weeks and after 4 weeks treatment with drug in the drinking solution or vehicle control. * $p<0.005$,  $p<0.001$ and * $p<0.0005$ vs 18 week vehicle treated control. #$p<0.05$, ##$p<0.01$, ###$p<0.005$ and ####$p<0.0005$ vs 14 week control. The latter comparison indicates the ability to reverse existing pathology.

Fibrosis in the heart after 4 weeks treatment with 500 pmol/kg/min T1, T2, T20, T31, T48 or T70 orally in 18 week old SHR on 2.2% salt diet is decreased compared to controls (FIG. 16).

Figure 17:
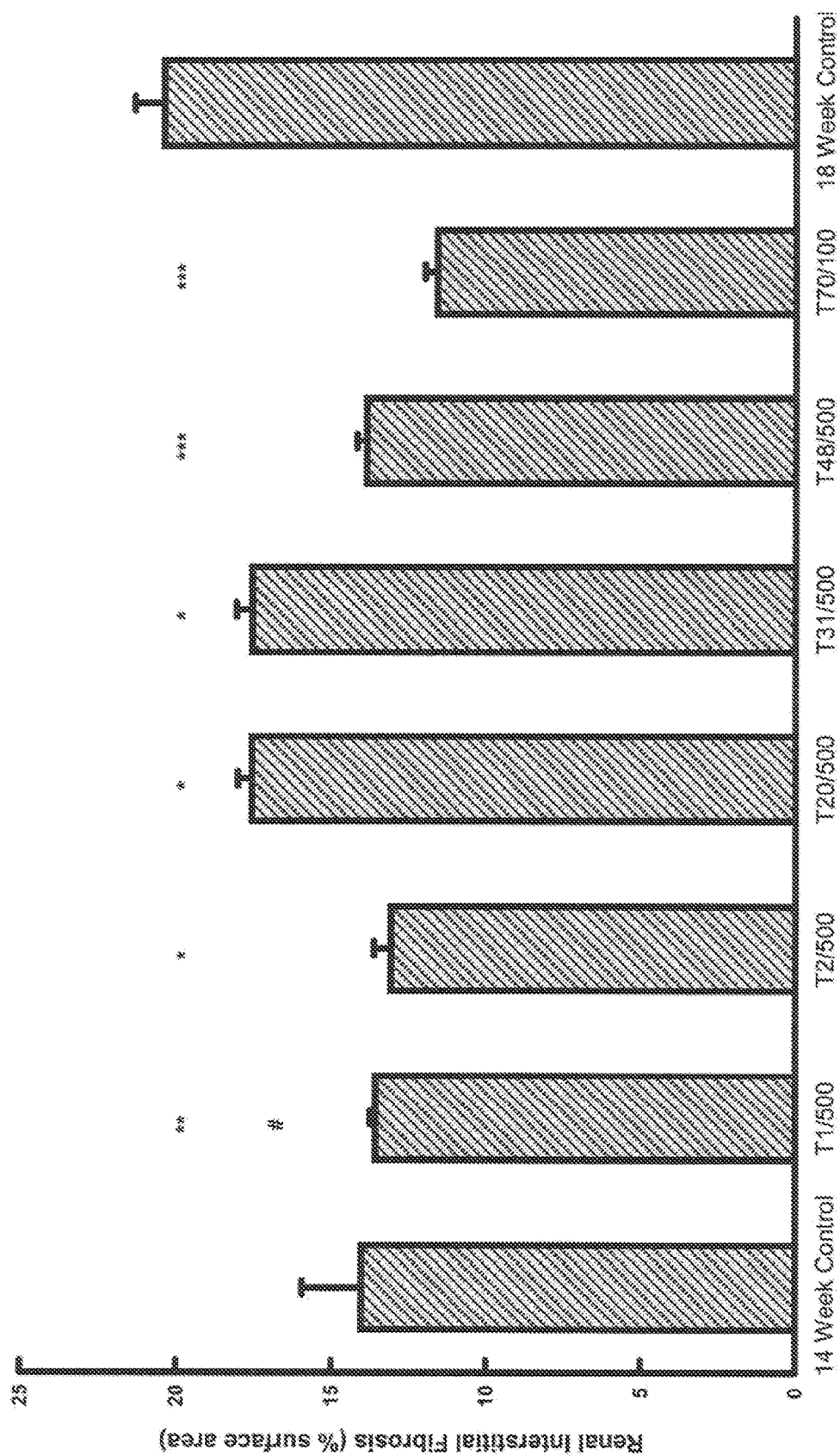
FIG. 17: Interstitial fibrosis in the kidney quantitated by computerised histomorphometry on Masson's trichrome stained histological sections in SHR on a 2.2% salt diet at 14 weeks and after 4 weeks treatment with drug in the drinking solution or vehicle control. * $p<0.005$,  $p<0.001$ and * $p<0.0005$ vs 18 week vehicle treated control. #$p<0.05$ vs 14 week control. The latter comparison indicates the ability to reverse existing pathology.

Fibrosis in the kidney after 4 weeks treatment with 500 pmol/kg/min T1, T2, T20, T31, T48 or T70 orally in 18 week old SHR on 2.2% salt diet is decreased compared to controls (FIG. 17).

Figure 18:
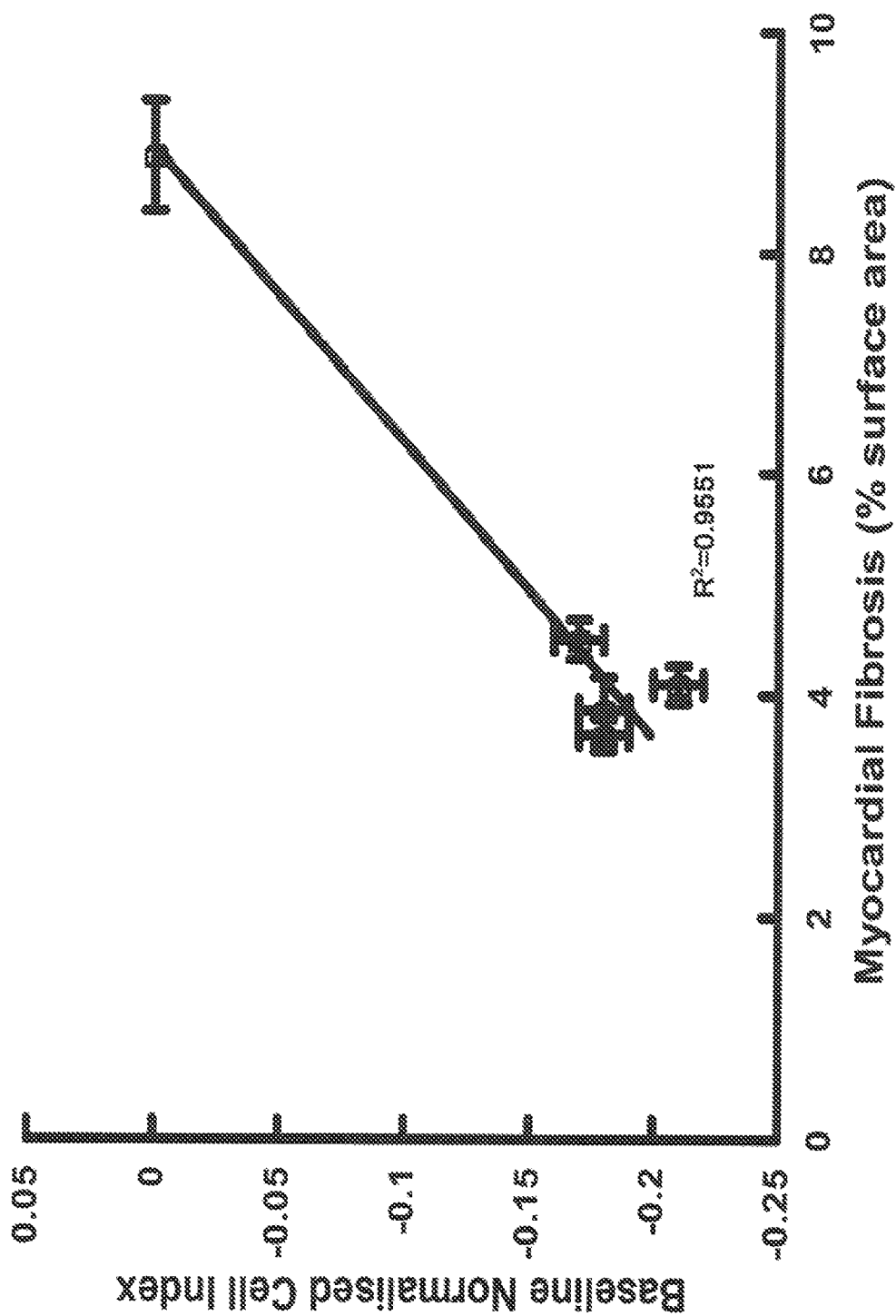
FIG. 18: Relationship between baseline normalised cell index for bovine aortic endothelial cells and myocardial fibrosis for various compounds.
Figure 19:
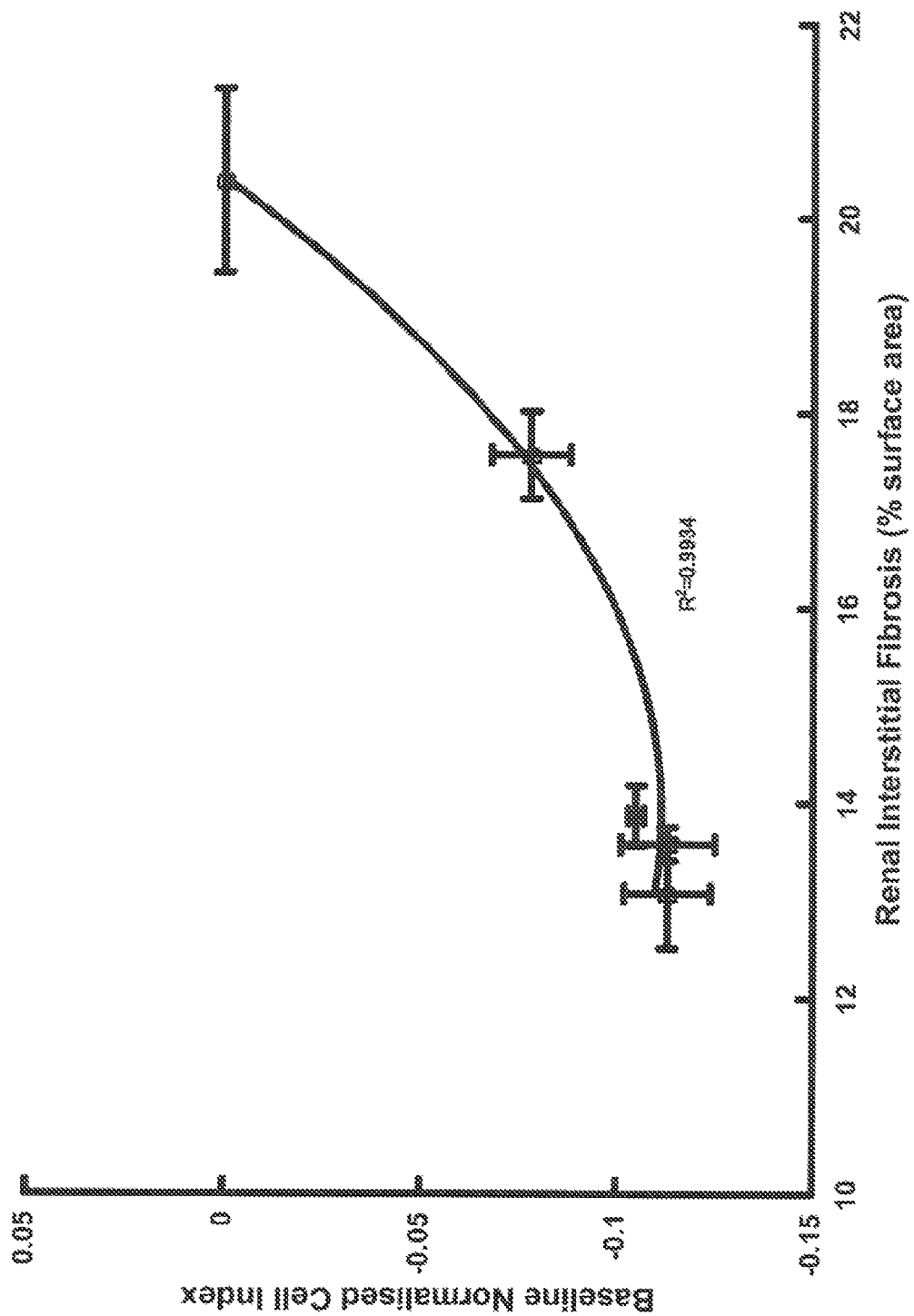
FIG. 19: Relationship between baseline normalised cell index for bovine aortic endothelial cells and renal interstitial fibrosis for various compounds.

The baseline normalised cell indexes of T1, T2, T20, T31, T48 and T70 on bovine aortic endothelial cells were compared with the myocardial fibrosis results (FIG. 18) and kidney fibrosis results (FIG. 19) for the compounds and showed a correlation between the in vivo and in vitro results.

Figure 20:
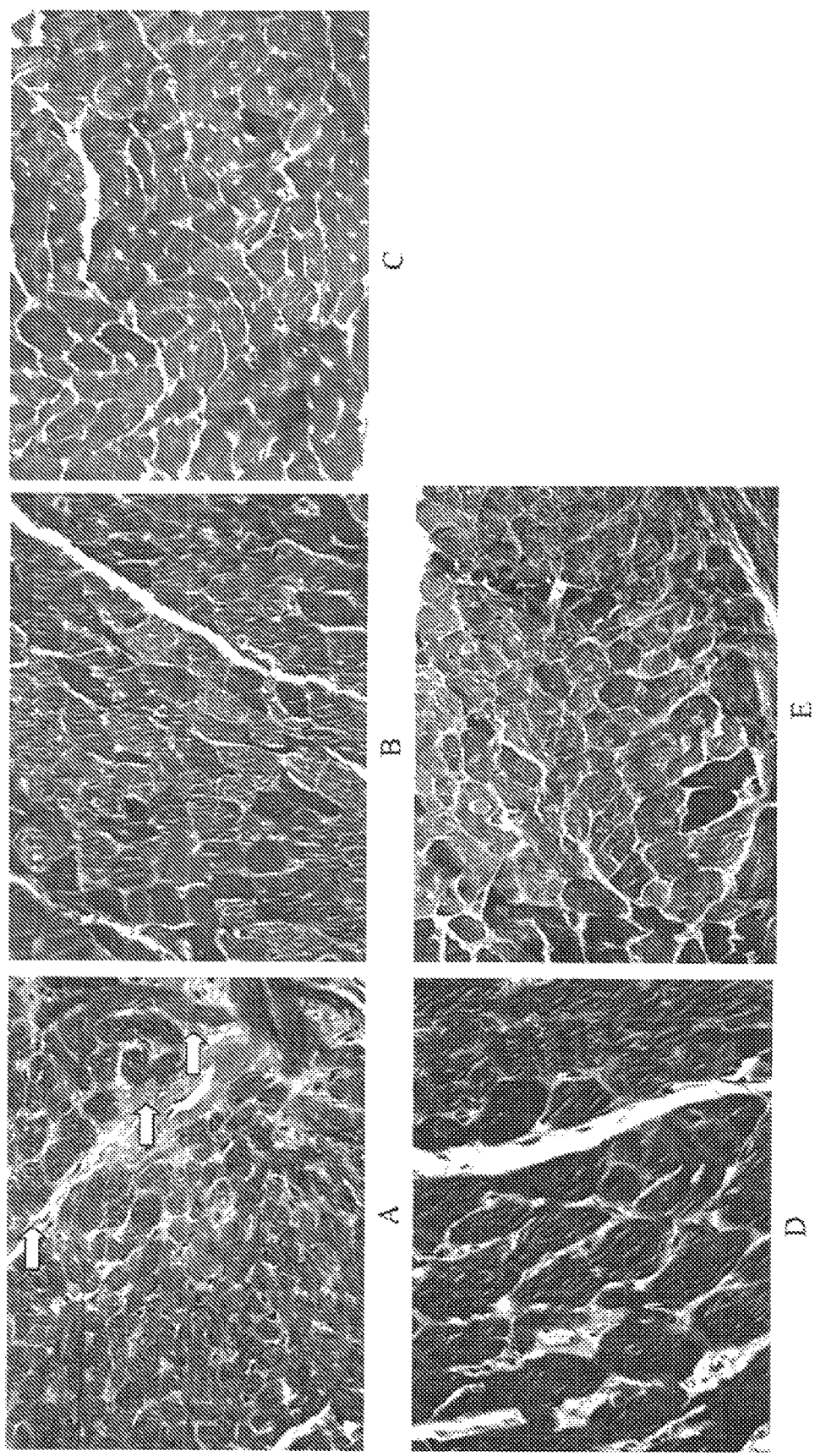
FIG. 20: Micrographs of heart for control rats (A) and rats treated for four weeks with 500 pmol/kg/min of T1 (B), T2 (C), T20 (D) or T31 (E).

Histological sections from the hearts (FIG. 20) of control rats (A) or rats treated for four weeks with 500 pmol/kg/min T1 (B), T2 (C), T20 (D) or T31 (e) on 2.2% salt diet showed that the control has extensive fibrosis (see arrows) appearing as a band of light grey in the right lower quarter extending diagonally up and out surrounding the large blood vessel as well as numerous muscle fibres with smaller amounts present throughout the micrograph (muscle fibres appear as discrete darker grey areas). In the sections from T1, T2, T20 and T31 treated rats no discrete areas of fibrosis are present, muscle fibres appear in cross section as varying shades of dark grey.

Histological sections from the kidneys (FIG. 21) of control rats (A) or rats treated for four weeks with 500 pmol/kg/min T1 (B), T2 (C), T20 (D) or T31 (e) on 2.2% salt diet showed that the control has extensive fibrosis appearing as thick lighter grey bands completely surrounding all tubules while in the centre 2 tubules have been obliterated (arrows). In the sections from T1, T2, T20 and T31 treated rats the fibrosis has been reduced to thin bands incompletely surrounding some but not all tubules.

The claims defining the invention are as follows:

1. A compound of the formula

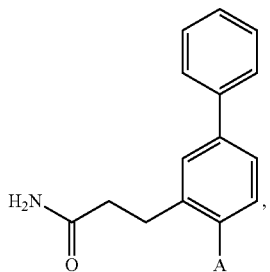

wherein:
A is selected from the group consisting of:

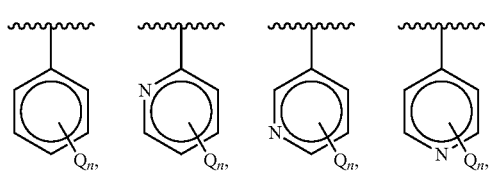

-continued

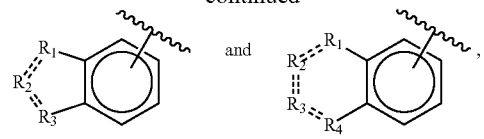

Q is independently selected from halo, alkyl, hydroxy, amino and substituted amino;

n is 0, 1, 2, 3, 4 or 5;

$R_1$, $R_3$ and $R_4$ are independently C, CH, $CH_2$, O, N, NH or S, and $R_2$ is C, CH, $CH_2$, N, NH, C—$CF_3$, CH—$CF_3$ or C=O, or a stereoisomer or pharmaceutically acceptable salt thereof, wherein when n is 1, Q cannot be hydroxy.

2. The compound, or a stereoisomer or pharmaceutically acceptable salt thereof, according to claim 1 wherein Q is halo selected from the group consisting of F, Cl, Br and I.

3. The compound, or a stereoisomer or pharmaceutically acceptable salt thereof, according to claim 1, wherein Q is substituted amino of the formula —NHW and wherein:

W is selected from —CN, —$SO_2(X)_aY$ and —$CO(X)_aY$, a is 0 or 1,

X is selected from —NH— and —O—, and

Y is selected from —H, —$CH_3$, —$CH_2CH_3$, —$CH_2OH$ and —$CH_2CH_2OH$.

4. The compound, or a stereoisomer or pharmaceutically acceptable salt thereof, according to claim 1, wherein Q is substituted amino selected from the group consisting of —$NHSO_2CH_3$, —NHCOH, —$NHCONHCH_3$, —$NHCONHCH_2CH_3$, —$NHSO_2NHCH_3$, —$NHSO_2NHCH_2CH_3$, —$NHCOCH_3$, —N HCOOCH_3, —$NHCOOCH_2CH_2OH$, —$NHCONH_2$ and —NHCN.

5. The compound, or a stereoisomer or pharmaceutically acceptable salt thereof, according to claim 1 wherein Q is alkyl selected from the group consisting of methyl, ethyl, propyl, butyl and pentyl.

6. The compound, or a stereoisomer or pharmaceutically acceptable salt thereof, according to claim 1 wherein A is selected from:

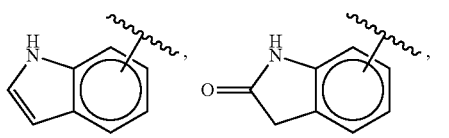

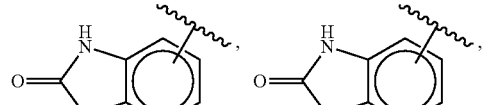

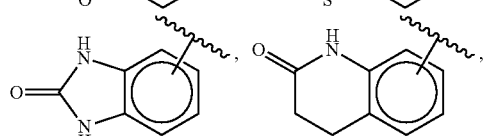

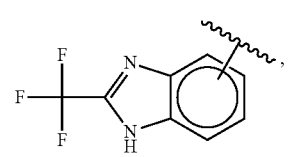

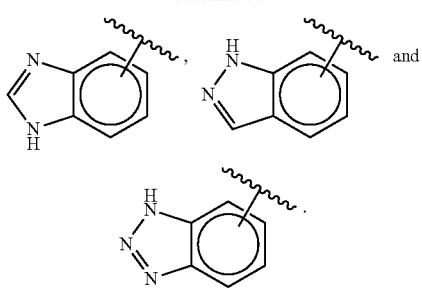
7. The compound, or a stereoisomer or pharmaceutically acceptable salt thereof, according to claim 1, wherein the compound is selected from the group consisting of:
(T1)
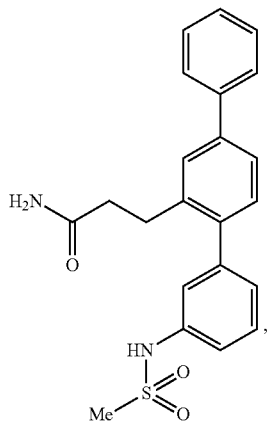
(T2)
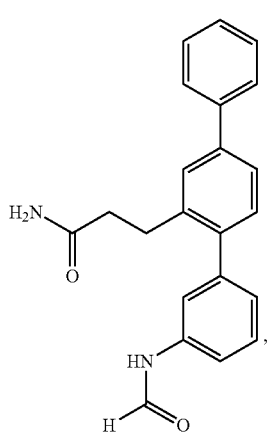
(T3)
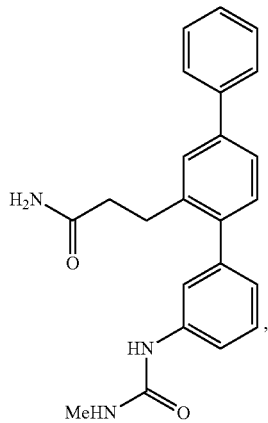
(T4)
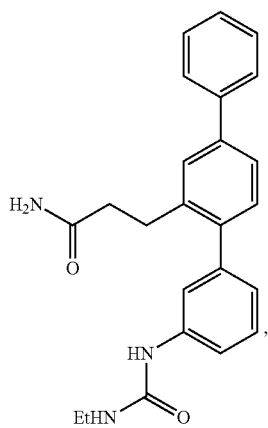
(T5)
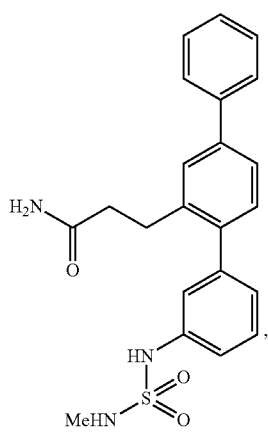

-continued
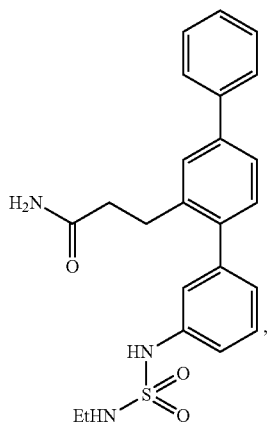 (T6)
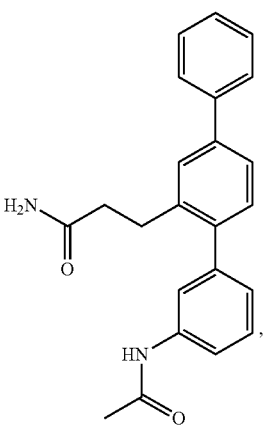 (T10)
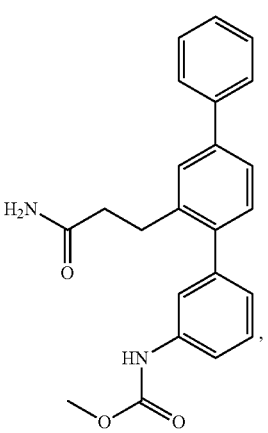 (T11)
-continued
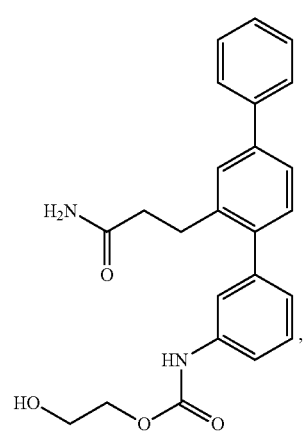 (T12)
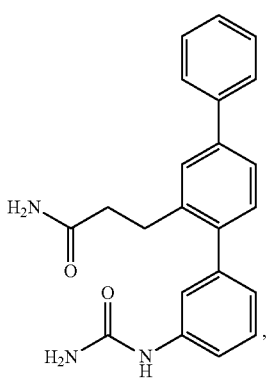 (T15)
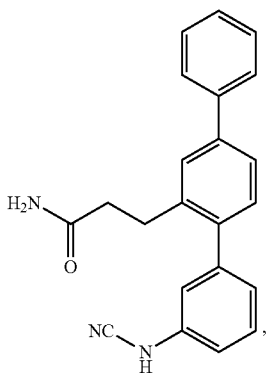 (T16)
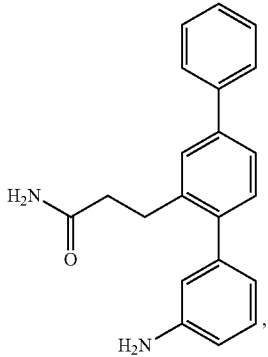 (T18)

77
-continued
(T20)
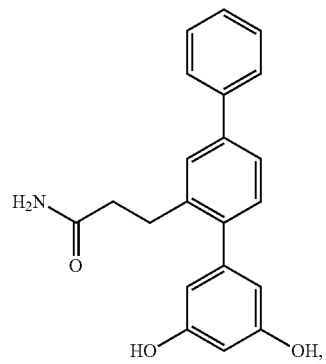
(T22)
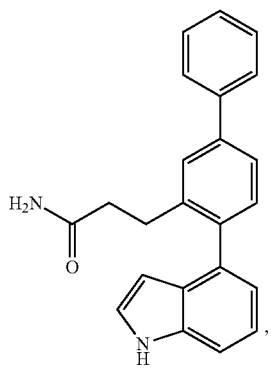
(T23)
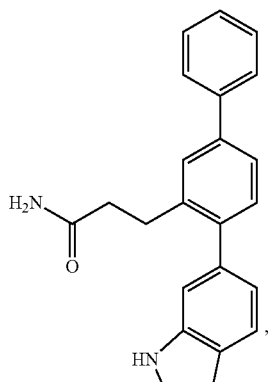
(T24)
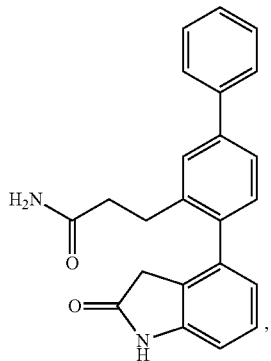
78
-continued
(T25)
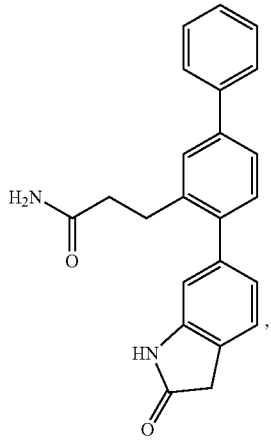
(T26)
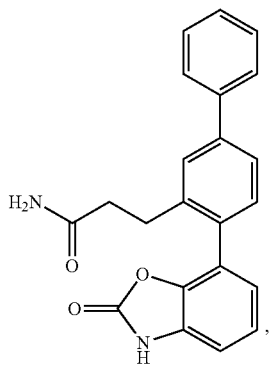
(T27)
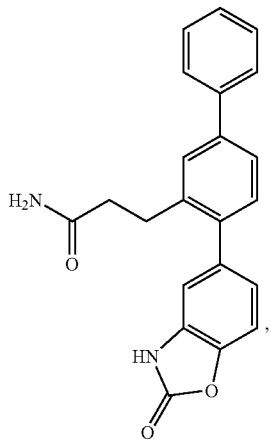

(T29) 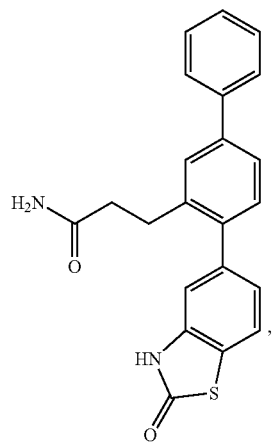
(T30) 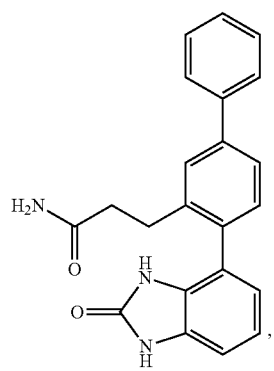
(T31) 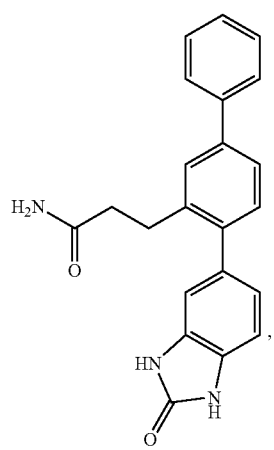
(T32) 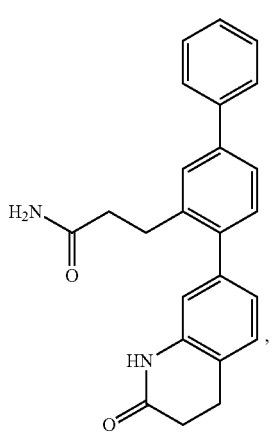
(T33) 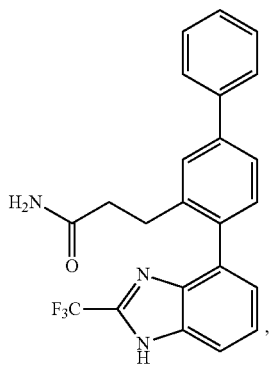
(T35) 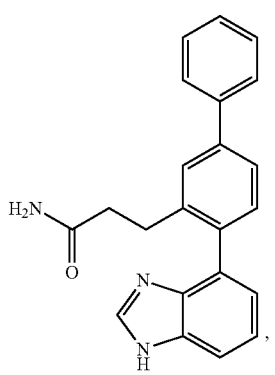
(T37) 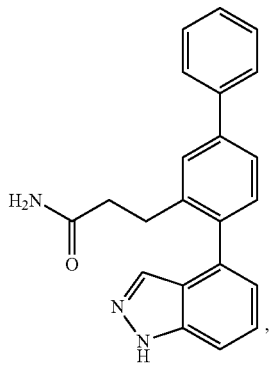

(T38) 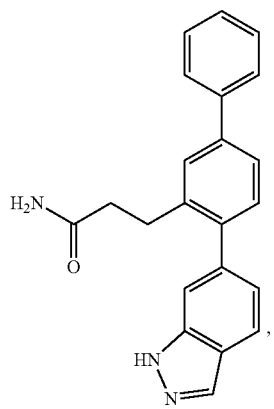
(T39) 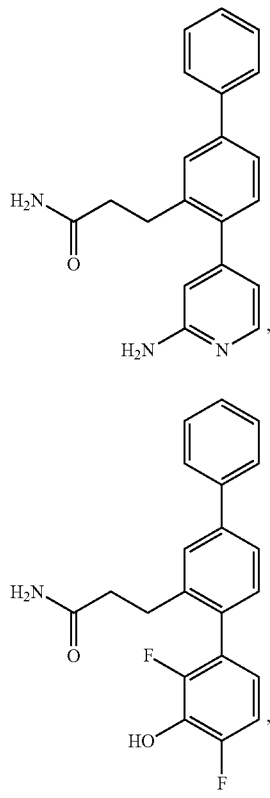
(T48)
(T58)
(T63) 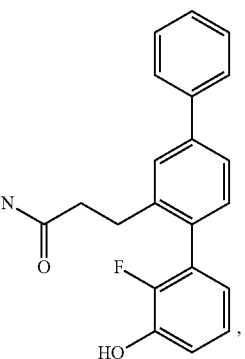
(T64)
(T65)
(T66)
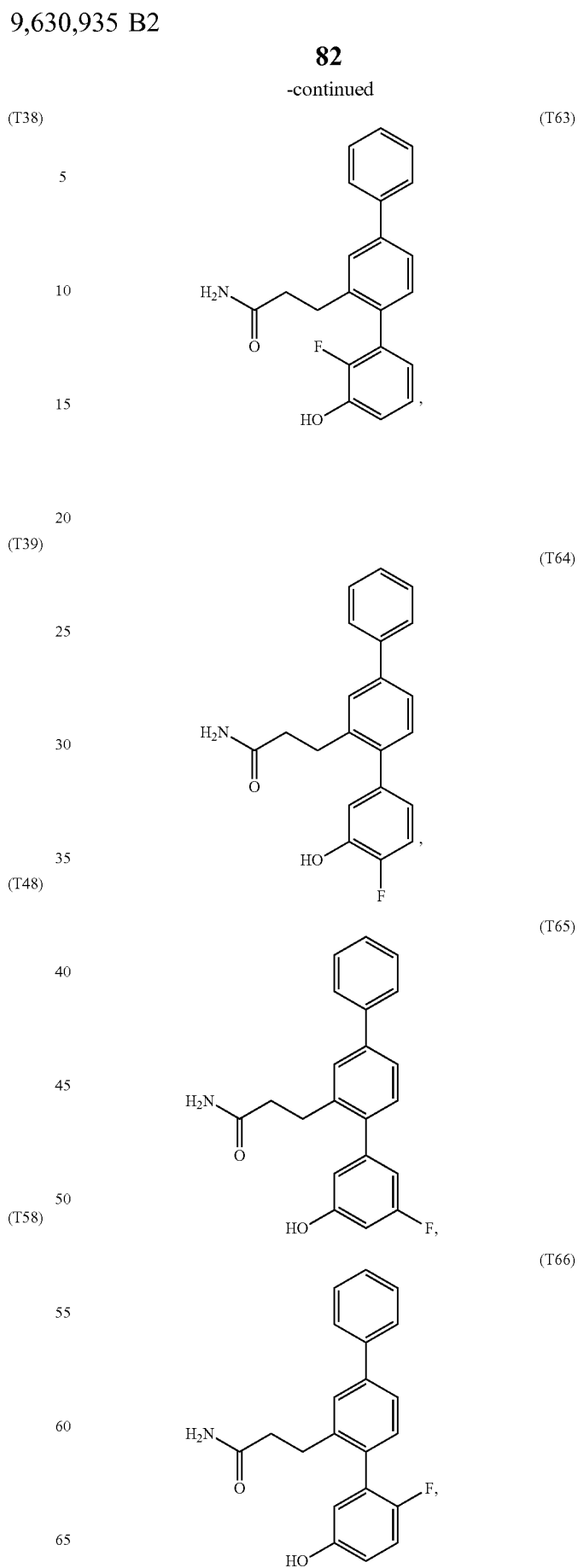

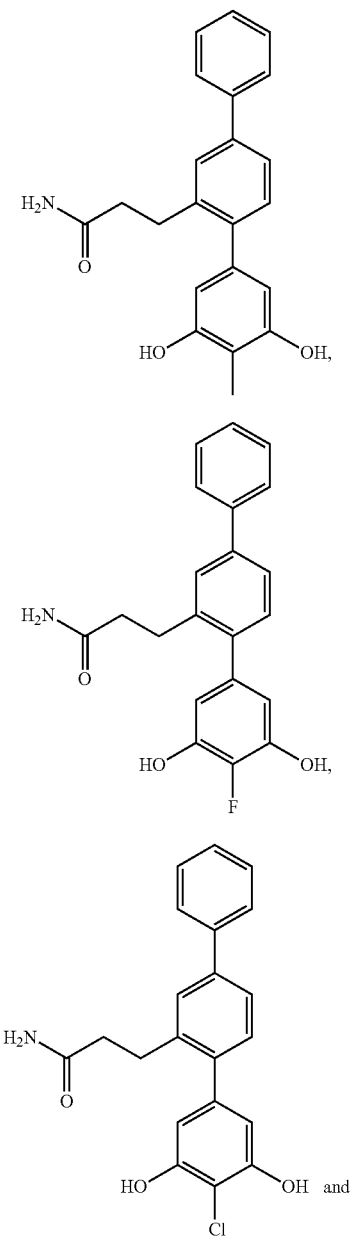

(T67)

(T68)

(T69)

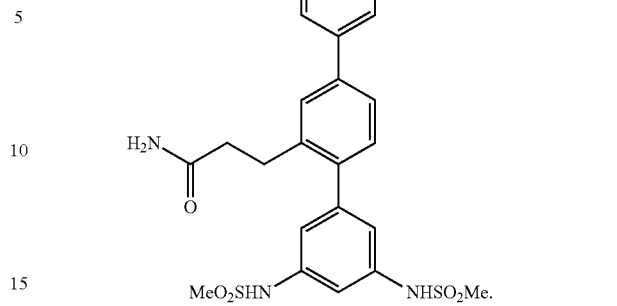

(T70)

8. A pharmaceutical composition comprising a compound, or a stereoisomer or pharmaceutically acceptable salt thereof, according to claim 1 and a pharmaceutically-acceptable excipient.

9. A method for the therapeutic treatment of hypertension or prehypertension in a subject comprising administering to the subject a compound, or a stereoisomer or pharmaceutically acceptable salt thereof, according to claim 1.

10. A method for the therapeutic treatment of fibrosis in a subject comprising administering to the subject a compound, or a stereoisomer or pharmaceutically acceptable salt thereof, according to claim 1.

11. The method according to claim 10 wherein the fibrosis is myocardial fibrosis or kidney fibrosis.

12. The method according to claim 10 wherein the fibrosis is myocardial fibrosis and kidney fibrosis.

13. A method for the therapeutic treatment of hypertension and fibrosis in a subject comprising administering to the subject a compound, or a stereoisomer or pharmaceutically acceptable salt thereof, according to claim 1.

14. The method according to claim 13 wherein the fibrosis is myocardial fibrosis or kidney fibrosis.

15. The method according to claim 13 wherein the fibrosis is myocardial fibrosis and kidney fibrosis.

16. A method for the treatment of prehypertension and fibrosis in a subject comprising administering to the subject a compound, or a stereoisomer or pharmaceutically acceptable salt thereof, according to claim 1.

17. The method according to claim 16 wherein the fibrosis is myocardial fibrosis or kidney fibrosis.

18. The method according to claim 16 wherein the fibrosis is myocardial fibrosis and kidney fibrosis.

* * * * *